United States Patent
Johnson et al.

(10) Patent No.: US 9,580,464 B2
(45) Date of Patent: Feb. 28, 2017

(54) ANTI-INFLAMMATORY PROTEINS AND PEPTIDES AND METHODS OF PREPARATION AND USE THEREOF

(71) Applicant: ManukaMed Limited, Masterton (NZ)

(72) Inventors: Keryn Johnson, Lower Hutt (NZ); Cynthia Sun, Lower Hutt (NZ); Ulrike Hubl, Lower Hutt (NZ); Jaganmohan Billakanti, Lower Hutt (NZ)

(73) Assignee: MANUKAMED HOLDINGS LIMITED PARTNERSHIP, Masterton (NZ)

( * ) Notice: Subject to any disclaimer, the term of this patent is extended or adjusted under 35 U.S.C. 154(b) by 0 days.

(21) Appl. No.: 14/410,227

(22) PCT Filed: Jun. 24, 2013

(86) PCT No.: PCT/NZ2013/000110
§ 371 (c)(1),
(2) Date: Dec. 22, 2014

(87) PCT Pub. No.: WO2013/191569
PCT Pub. Date: Dec. 27, 2013

(65) Prior Publication Data
US 2015/0337019 A1 Nov. 26, 2015

(30) Foreign Application Priority Data
Jun. 22, 2012 (NZ) ........................ 600847

(51) Int. Cl.
| | | |
|---|---|---|
| A61K 38/00 | (2006.01) | |
| A61K 38/04 | (2006.01) | |
| A61K 38/06 | (2006.01) | |
| A61K 38/08 | (2006.01) | |
| A61K 38/10 | (2006.01) | |
| A61L 15/32 | (2006.01) | |
| A61L 15/44 | (2006.01) | |
| C07K 5/08 | (2006.01) | |
| C07K 5/10 | (2006.01) | |
| C07K 7/00 | (2006.01) | |
| C07K 5/117 | (2006.01) | |
| C07K 14/81 | (2006.01) | |
| C07K 14/435 | (2006.01) | |
| C07K 5/087 | (2006.01) | |
| C07K 5/09 | (2006.01) | |
| C07K 5/11 | (2006.01) | |
| C07K 5/103 | (2006.01) | |
| C07K 5/083 | (2006.01) | |

(52) U.S. Cl.
CPC ............ *C07K 5/1024* (2013.01); *A61L 15/32* (2013.01); *A61L 15/44* (2013.01); *C07K 5/0808* (2013.01); *C07K 5/0812* (2013.01); *C07K 5/0815* (2013.01); *C07K 5/1013* (2013.01); *C07K 5/1019* (2013.01); *C07K 14/43572* (2013.01); *C07K 14/8139* (2013.01); *A61K 38/00* (2013.01); *A61L 2300/25* (2013.01); *A61L 2300/252* (2013.01); *A61L 2300/41* (2013.01)

(58) Field of Classification Search
CPC ........ A61K 38/00; A61K 38/04; A61K 38/06; A61K 38/08; A61K 38/10; A61L 15/32; A61L 15/44; A61L 2300/25; A61L 2300/252; A61L 2300/41; C07K 14/43572; C07K 14/8139; C07K 5/0808; C07K 5/0812; C07K 5/0815; C07K 5/1013; C07K 5/1019; C07K 5/1024; C07K 5/08; C07K 5/10; C07K 7/00
USPC .......................... 514/20.2; 530/328, 329, 331
See application file for complete search history.

(56) References Cited

U.S. PATENT DOCUMENTS

| | | |
|---|---|---|
| 7,230,079 B2 | 6/2007 | Okamoto et al. |
| 9,180,219 B2 | 11/2015 | Watson |
| 2006/0159834 A1 | 7/2006 | Shibuya et al. |
| 2008/0292715 A1 | 11/2008 | Snow et al. |
| 2010/0233285 A1 | 9/2010 | Stuart et al. |
| 2011/0287059 A1 | 11/2011 | Stephens et al. |
| 2012/0269879 A1 | 10/2012 | Watson |
| 2013/0171262 A1 | 7/2013 | Stuart et al. |
| 2014/0127283 A1 | 5/2014 | Watson |
| 2014/0154803 A1 | 6/2014 | Bean et al. |
| 2016/0101210 A1 | 4/2016 | Watson |
| 2016/0158403 A1 | 6/2016 | Watson |

FOREIGN PATENT DOCUMENTS

| | | |
|---|---|---|
| CN | 1980577 A | 6/2007 |
| JP | 2008-137968 A | 6/2008 |
| WO | 2010044042 A1 | 4/2010 |
| WO | 2010-082846 A1 | 7/2010 |
| WO | 2010/136182 A1 | 12/2010 |
| WO | 2012-087160 A2 | 6/2012 |

OTHER PUBLICATIONS

U.S. Appl. No. 12/996,146, filed Apr. 6, 2011, Denis Eric Watson.
U.S. Appl. No. 14/025,407, filed Sep. 12, 2013, Denis Eric Watson.
U.S. Appl. No. 14/807,577, filed Jul. 23, 2015, Denis Eric Watson.
U.S. Appl. No. 12/519,002, filed Dec. 11, 2009, Mark Shane Stuart.
U.S. Appl. No. 13/679,283, filed Nov. 16, 2012, Mark Shane Stuart.

(Continued)

*Primary Examiner* — Julie Ha
(74) *Attorney, Agent, or Firm* — Nelson Mullins Riley & Scarborough LLP; Jane E. Remillard, Esq.; Cynthia L. Kanik

(57) ABSTRACT

Anti-inflammatory proteins/peptides are described, as well as their uses, methods of preparation, and methods of their detection. Specifically described are major royal jelly proteins modified by methylglyoxal and fragments thereof from a *Leptospermum* derived honey and royal jelly.

8 Claims, 16 Drawing Sheets

(56) References Cited

OTHER PUBLICATIONS

U.S. Appl. No. 14/410,227, filed Feb. 4, 2014, Amanda Bean.
U.S. Appl. No. 12/996,146, Mar. 13, 2013.
U.S. Appl. No. 14/025,407, Jul. 6, 2015.
U.S. Appl. No. 14/025,407, Nov. 6, 2014.
U.S. Appl. No. 14/025,407, Mar. 18, 2015.
U.S. Appl. No. 12/519,002, Jun. 21, 2012.
U.S. Appl. No. 12/519,002, Mar. 28, 2012.
U.S. Appl. No. 13/679,283, Sep. 17, 2015.
U.S. Appl. No. 13/679,283, Mar. 11, 2015.
U.S. Appl. No. 13/679,283, Jul. 17, 2014.
Adams, C.J. et al., "Isolation of HPLC and characterization of the bioactive fraction of New Zealand manuka (Leptospermum scoparium) honey," Carbohydrate Research, vol. 343(4), pp. 651-659 (2008).
Ahmed N. et al., "Peptidyl fluoromethyl ketones as inhibitors of cathepsin B Implication for treatment of rheumatoid arthritis," Biochem Pharmacol. Sep. 20 25, vol. 44(6), pp. 1201-1207 (1992).
Allen, K. et al., "A survey of the antibacterial activity of some New Zealand honeys. Journal of Pharmacy and Pharmacology," vol. 43(12), pp. 817-822 (1991).
Bilikova, Katarina et al., "Towards functional proteomics of minority component of honeybee royal jelly: the effect of post-translational modifications on the antimicrobial activity of apalbumin2," Proteomics, vol. 9(8), pp. 2131-2138 (2009).
Fan, X. et al., "Methylglyoxal-bovine serum albumin stimulates tumor necrosis factor alpha secretion in RAW 264.7 cells through activation of mitogen-activating protein kinase, nuclear factor kappaB and intracellular reactive oxygen species formation," Archives of Biochemistry and Biophysics, vol. 409(2), pp. 274-286 (2003).
GenBank Accession No. NP_001011579, Major Royal Jelly Protein 1 Precursor [Apis mellifera], 2 page (2013).
International Preliminary Report on Patentability, PCT/NZ2013/000110, dated Dec. 23, 2014, pp. 1-12.
International Search Report and Written Opinion, PCT/NZ2013/000110, dated Sep. 4, 2013, pp. 1-6.
Kim, J. et al.,"Methylglyoxal induces cellular damage by increasing argpyrimidine accumulation and oxidative DNA damage in human lens epithelial cells," Biochem Biophys Res Commun., vol. 391(1), pp. 346-351 (2010).
Kimura Y, et al., "Structural features of N-glycans linked to royal jelly glycoproteins: structures of high-mannose type, hybrid type, and biantennary type glycans," Biosci. Biotechnol. Biochem., vol. 64(10), pp. 2109-2120 (2000).
Kohno, K. et al, "Royal jelly inhibits the production of pro inflammatory cytokines by activated macrophages," Biosci. Biotechnol. Biochem., vol. 68(1), pp. 138-145 (2004).
Leong, A. et al., "Indigenous New Zealand honeys exhibit multiple anti-inflammatory activities," Innate Immunity, vol. 18, pp. 459-466 (2011).
Lerrer, B. et al., "Honey and royal jelly, like human milk, abrogate lectin-dependent infection preceding Pseudomonas aeruginosa adhesion," ISME Journal, vol. 1, pp. 149-155 (2007).
Majtan, J. et al "Methylglyoxal—A Potential Risk Factor of Manuka Honey in Healing of Diabetic Ulcers," Evidence-Based Complementary and Alternative Medicine, vol. 2011, Article ID 295494, 5 pages (2010).
Majtan, J. et al., "The immunostimulatory effect of the recombinant apalbumin 1-major honeybee royal jelly protein-on TNF alpha release," Int. Immunopharmacol., vol. 6(2), pp. 269-278 (2005).
Mavric, E. et al., "Identification and quantification of methylglyoxal as the dominant antibacterial constituent of Manuka (Leptospermum scoparium) honeys from New Zealand," Mol Nutr Food Res, vol. 52, pp. 483-489 (2008).
O'Neil, J. et al., "Inactivation of cathepsin B by oxidized LDL involves complex formation induced by binding of putative reactive sites exposed at low pH to thiols on the enzyme," Free Radical Biology & Medicine, vol. 23(2), pp. 215-225 (1997).
Prakash, A. et al., "Effect of Different Doses of Manuka Honey in Experimentally Induced Inflammatory Bowel Disease in Rats," Phytotherapy Research, vol. 22, pp. 1511-1519 (2008).
Rossano R., et al.,"What Are the Proteolytic Enzymes of Honey and What They Do Tell Us? A Fingerprint Analysis by 2-D Zymography of Unifloral Honeys," PLoS ONE, vol. 7(11), 17 pages (2012).
Simuth, J. et al., "Immunochemical approach to detection of adulteration in honey: physiologically active royal jelly protein stimulating TNF-alpha release is a regular component of honey," Journal of Agricultural and Food Chemistry, vol. 52(8), pp. 2154-2158 (2004).
Yamawaki, H. et al. "Methylglyoxal mediates vascular inflammation via JNK and p38 in human endothelial cells," Am J Physiol Cell Physiol, vol. 295, pp. C1510-C1517 (2008).
U.S. Appl. No. 13/997,031, filed Feb. 4, 2014, Amanda Bean.
U.S. Appl. No. 14/904,027, filed Jan. 8, 2016, Denis Eric Watson.
U.S. Appl. No. 13/997,031, Jul. 28, 2016.
U.S. Appl. No. 13/997,031, Jun. 7, 2016.
U.S. Appl. No. 13/997,031, Oct. 16, 2015.
U.S. Appl. No. 13/997,031, Apr. 22, 2015.
U.S. Appl. No. 14/904,027, Sep. 15, 2016.
Brudzynski, K. et al., "Storage-induced Chemical Changes in Actice Components of Honey de-regulate its anitbaterial activity," Food Chemistry, vol. 126: 1155-1163 (2011).
Fontana, R. et al., "Jelleines: a family of antimicrobial peptides from the royal jelly of honeybees (Apis mellifera)," Peptides, vol. 25 (6): 919-928 (2004).
Greifenhagen, U. et al., "Sensitive and site-specific identification of carboxymethylated and carboxyethylated peptides in tryptic digests of proteins and human plasma", Journal of Proteome Research, vol. 14 (2): 768-777 (2015).
Gruber, P. et al., "Chemoselective synthesis of peptides containing major advanced glycation end-products of lysine and arginine," Journal of Peptide Research, vol. 66 (3):111-124 (2005).
Majtan, J. et al., "Methylglyoxal-induced modifications of significant honeybee proteinous components in manuka honey: Possible therapeutic implications," Fitoterapia, vol. 83 (4):671-677 (2012).
Petrova, K. et al., "Characterization of the deoxyguanosine-lysine cross-link of methylglyoxal," Chemical Research in Toxicology, vol. 27(6):1019-1029 (2014).
Xue, J. et al., "Advanced glycation end product recognition by the receptor for AGEs," Structure, Current Biology, LTD., Philadlephia, PA, US, vol. 19 (5): 722-732 (2011).

|  | 10 | 20 | 30 | 40 | 50 | 60 |
|---|---|---|---|---|---|---|
|  | MTRLFMLVCL | GIVCQGTTGN | ILRGESLNKS | LPILHEWKFF | DYDFGSDERR | QDAILSGEYD |

|  | 70 | 80 | 90 | 100 | 110 | 120 |
|---|---|---|---|---|---|---|
|  | YKNNYPSDID | QWHDKIFVTM | LRYNGVPSSL | NVISKKVGDG | GPLLQPYPDW | SFAKYDDCSG |

|  | 130 | 140 | 150 | 160 | 170 | 180 |
|---|---|---|---|---|---|---|
|  | IVSASKLAID | KCDRLWVLDS | GLVNNTQPMC | SPKLLTFDLT | TSQLLKQVEI | PHDVAVNATT |

|  | 190 | 200 | 210 | 220 | 230 | 240 |
|---|---|---|---|---|---|---|
|  | GKGRLSSLAV | QSLDCNTNSD | TMVYIADEKG | EGLIVYHNSD | DSFHRLTSNT | FDYDPKFTKM |

|  | 250 | 260 | 270 | 280 | 290 | 300 |
|---|---|---|---|---|---|---|
|  | TIDGESYTAQ | DGISGMALSP | MTNNLYYSPV | ASTSLYYVNT | EQFRTSDYQQ | NDIHYEGVQN |

|  | 310 | 320 | 330 | 340 | 350 | 360 |
|---|---|---|---|---|---|---|
|  | ILDTQSSAKV | VSKSGVLFFG | LVGDSALGCW | NEHRTLERHN | IRTVAQSDET | LQMIASMKIK |

|  | 370 | 380 | 390 | 400 | 410 | 420 |
|---|---|---|---|---|---|---|
|  | EALPHVPIFD | RYINREYILV | LSNKMQKMVN | NDFNFDDVNF | RIMNANVNEL | ILNTRCENPD |

|  | 430 |  |  |
|---|---|---|---|
| NDRTPFKISI | HL | SEQ ID NO: 1 |  |

FIGURE 10

PFKISIHL (SEQ ID NO: 18)

Ac-PFKISIHL-OH (SEQ ID NO: 19)
Ac-KISIHL-OH (SEQ ID NO: 20)
Ac-KISI-OH (SEQ ID NO: 21)
Ac-PFKI-OH (SEQ ID NO: 22)

NQKNNNQNDN (SEQ ID NO: 23)

Ac-NQKNNNQNDN-OH (SEQ ID NO: 24)
Ac-NQKNNNQN-OH (SEQ ID NO: 25)
Ac-NQKNNN-OH (SEQ ID NO: 26)
Ac-NQKN-OH (SEQ ID NO: 27)
Ac-KN-OH (SEQ ID NO: 28)

HHSSKLH (SEQ ID NO: 29)

Ac-HSSKLH-OH (SEQ ID NO: 30)
Ac-SKLH-OH (SEQ ID NO: 31)
Ac-SK-OH (SEQ ID NO: 32)
Ac-HSSK-OH (SEQ ID NO: 33)
Ac-SSKS-OH (SEQ ID NO: 34)

HSSKSNNRHNNND (SEQ ID NO: 35)

Ac-SSKSNNRHNNND-OH (SEQ ID NO: 36)
Ac-SSKSNNRHNN-OH (SEQ ID NO: 37)
Ac-SSKSNNRH-OH (SEQ ID NO: 38)
Ac-SSKSNN-OH (SEQ ID NO: 39)
Ac-SSKS-OH (SEQ ID NO: 40)
Ac-KS-OH (SEQ ID NO: 41)

QNKHNN (SEQ ID NO: 42)

Ac-QNKHNN-OH (SEQ ID NO: 43)
Ac-KHNN-OH (SEQ ID NO: 44)
Ac-KH-OH (SEQ ID NO: 45)
Ac-QNKH-OH (SEQ ID NO: 46)

Ac-LVK-OH (SEQ ID NO: 48)
Ac-LVK-NH2 (SEQ ID NO: 49)
Ac-LIR-OH (SEQ ID NO: 51)
Ac-LIR-NH2 (SEQ ID NO: 52)

Ac-LLK-OH (SEQ ID NO: 56)
Ac-LLK-NH2 (SEQ ID NO: 57)
Ac-KI-OH (SEQ ID NO: 58)

SEQUENCE LISTING

<160> NUMBER OF SEQ ID NOS: 145

<210> SEQ ID NO 1
<211> LENGTH: 432
<212> TYPE: PRT
<213> ORGANISM: Apis mellifera

<400> SEQUENCE: 1

```
Met Thr Arg Leu Phe Met Leu Val Cys Leu Gly Ile Val Cys Gln Gly
1               5                   10                  15

Thr Thr Gly Asn Ile Leu Arg Gly Glu Ser Leu Asn Lys Ser Leu Pro
            20                  25                  30

Ile Leu His Glu Trp Lys Phe Phe Asp Tyr Asp Phe Gly Ser Asp Glu
        35                  40                  45

Arg Arg Gln Asp Ala Ile Leu Ser Gly Tyr Asp Tyr Lys Asn Asn
    50                  55                  60

Tyr Pro Ser Asp Ile Asp Gln Trp His Asp Lys Ile Phe Val Thr Met
65                  70                  75                  80

Leu Arg Tyr Asn Gly Val Pro Ser Ser Leu Asn Val Ile Ser Lys Lys
                85                  90                  95

Val Gly Asp Gly Gly Pro Leu Leu Gln Pro Tyr Pro Asp Trp Ser Phe
            100                 105                 110

Ala Lys Tyr Asp Asp Cys Ser Gly Ile Val Ser Ala Ser Lys Leu Ala
        115                 120                 125

Ile Asp Lys Cys Asp Arg Leu Trp Val Leu Asp Ser Gly Leu Val Asn
    130                 135                 140

Asn Thr Gln Pro Met Cys Ser Pro Lys Leu Leu Thr Phe Asp Leu Thr
145                 150                 155                 160

Thr Ser Gln Leu Leu Lys Gln Val Glu Ile Pro His Asp Val Ala Val
                165                 170                 175

Asn Ala Thr Thr Gly Lys Gly Arg Leu Ser Ser Leu Ala Val Gln Ser
            180                 185                 190

Leu Asp Cys Asn Thr Asn Ser Asp Thr Met Val Tyr Ile Ala Asp Glu
        195                 200                 205

Lys Gly Glu Gly Leu Ile Val Tyr His Asn Ser Asp Asp Ser Phe His
    210                 215                 220

Arg Leu Thr Ser Asn Thr Phe Asp Tyr Asp Pro Lys Phe Thr Lys Met
225                 230                 235                 240

Thr Ile Asp Gly Glu Ser Tyr Thr Ala Gln Asp Gly Ile Ser Gly Met
                245                 250                 255

Ala Leu Ser Pro Met Thr Asn Asn Leu Tyr Tyr Ser Pro Val Ala Ser
            260                 265                 270

Thr Ser Leu Tyr Tyr Val Asn Thr Glu Gln Phe Arg Thr Ser Asp Tyr
        275                 280                 285

Gln Gln Asn Asp Ile His Tyr Glu Gly Val Gln Asn Ile Leu Asp Thr
    290                 295                 300

Gln Ser Ser Ala Lys Val Val Ser Lys Ser Gly Val Leu Phe Phe Gly
305                 310                 315                 320

Leu Val Gly Asp Ser Ala Leu Gly Cys Trp Asn Glu His Arg Thr Leu
                325                 330                 335

Glu Arg His Asn Ile Arg Thr Val Ala Gln Ser Asp Glu Thr Leu Gln
            340                 345                 350

Met Ile Ala Ser Met Lys Ile Lys Glu Ala Leu Pro His Val Pro Ile
        355                 360                 365
```

```
Phe Asp Arg Tyr Ile Asn Arg Glu Tyr Ile Leu Val Leu Ser Asn Lys
    370                 375                 380

Met Gln Lys Met Val Asn Asn Asp Phe Asn Phe Asp Asp Val Asn Phe
385                 390                 395                 400

Arg Ile Met Asn Ala Asn Val Asn Glu Leu Ile Leu Asn Thr Arg Cys
                405                 410                 415

Glu Asn Pro Asp Asn Asp Arg Thr Pro Phe Lys Ile Ser Ile His Leu
                420                 425                 430

<210> SEQ ID NO 2
<211> LENGTH: 452
<212> TYPE: PRT
<213> ORGANISM: Apis mellifera

<400> SEQUENCE: 2

Met Thr Arg Trp Leu Phe Met Val Ala Cys Leu Gly Ile Ala Cys Gln
1               5                   10                  15

Gly Ala Ile Val Arg Glu Asn Ser Pro Arg Asn Leu Glu Lys Ser Leu
            20                  25                  30

Asn Val Ile His Glu Trp Lys Tyr Phe Asp Tyr Asp Phe Gly Ser Glu
        35                  40                  45

Glu Arg Arg Gln Ala Ala Ile Gln Ser Gly Glu Tyr Asp His Thr Lys
50                  55                  60

Asn Tyr Pro Phe Asp Val Asp Gln Trp Arg Asp Lys Thr Phe Val Thr
65                  70                  75                  80

Ile Leu Arg Tyr Asp Gly Val Pro Ser Thr Leu Asn Val Ile Ser Gly
                85                  90                  95

Lys Thr Gly Lys Gly Gly Arg Leu Leu Lys Pro Tyr Pro Asp Trp Ser
            100                 105                 110

Phe Ala Glu Phe Lys Asp Cys Ser Lys Ile Val Ser Ala Phe Lys Ile
        115                 120                 125

Ala Ile Asp Lys Phe Asp Arg Leu Trp Val Leu Asp Ser Gly Leu Val
    130                 135                 140

Asn Arg Thr Val Pro Val Cys Ala Pro Lys Leu His Val Phe Asp Leu
145                 150                 155                 160

Lys Thr Ser Asn His Leu Lys Gln Ile Glu Ile Pro His Asp Ile Ala
                165                 170                 175

Val Asn Ala Thr Thr Gly Lys Gly Gly Leu Val Ser Leu Ala Val Gln
            180                 185                 190

Ala Ile Asp Leu Ala Asn Thr Leu Val Tyr Met Ala Asp His Lys Gly
        195                 200                 205

Asp Ala Leu Ile Val Tyr Gln Asn Ala Asp Asp Ser Phe His Arg Leu
    210                 215                 220

Thr Ser Asn Thr Phe Asp Tyr Asp Pro Arg Tyr Ala Lys Met Thr Ile
225                 230                 235                 240

Asp Gly Glu Ser Phe Thr Leu Lys Asn Gly Ile Cys Gly Met Ala Leu
                245                 250                 255

Ser Pro Val Thr Asn Asn Leu Tyr Tyr Ser Pro Leu Ala Ser His Gly
            260                 265                 270

Leu Tyr Tyr Val Asn Thr Ala Pro Phe Met Lys Ser Gln Phe Gly Glu
        275                 280                 285

Asn Asn Val Gln Tyr Gln Gly Ser Glu Asp Ile Leu Asn Thr Gln Ser
    290                 295                 300

Leu Ala Lys Ala Val Ser Lys Asn Gly Val Leu Phe Val Gly Leu Val
305                 310                 315                 320
```

```
Gly Asn Ser Ala Val Gly Cys Trp Asn Glu His Gln Ser Leu Gln Arg
            325                 330                 335

Gln Asn Leu Glu Met Val Ala Gln Asn Asp Arg Thr Leu Gln Met Ile
            340                 345                 350

Ala Gly Met Lys Ile Lys Glu Glu Leu Pro His Phe Val Gly Ser Asn
            355                 360                 365

Lys Pro Val Lys Asp Glu Tyr Met Leu Val Leu Ser Asn Arg Met Gln
            370                 375                 380

Lys Ile Val Asn Asp Asp Phe Asn Phe Asp Asp Val Asn Phe Arg Ile
385                 390                 395                 400

Leu Gly Ala Asn Val Lys Glu Leu Ile Arg Asn Thr His Cys Val Asn
            405                 410                 415

Asn Asn Gln Asn Asp Asn Ile Gln Asn Thr Asn Asn Gln Asn Asp Asn
            420                 425                 430

Asn Gln Lys Asn Asn Lys Lys Asn Ala Asn Asn Gln Lys Asn Asn Asn
            435                 440                 445

Gln Asn Asp Asn
    450

<210> SEQ ID NO 3
<211> LENGTH: 544
<212> TYPE: PRT
<213> ORGANISM: Apis mellifera

<400> SEQUENCE: 3

Met Thr Lys Trp Leu Leu Val Val Cys Leu Gly Ile Ala Cys Gln
1               5                   10                  15

Asp Val Thr Ser Ala Ala Val Asn His Gln Arg Lys Ser Ala Asn Asn
            20                  25                  30

Leu Ala His Ser Met Lys Val Ile Tyr Glu Trp Lys His Ile Asp Phe
            35                  40                  45

Asp Phe Gly Ser Asp Glu Arg Arg Asp Ala Ala Ile Lys Ser Gly Glu
        50                  55                  60

Phe Asp His Thr Lys Asn Tyr Pro Phe Asp Val Asp Arg Trp Arg Asp
65                  70                  75                  80

Lys Thr Phe Val Thr Ile Glu Arg Asn Asn Gly Val Pro Ser Ser Leu
                85                  90                  95

Asn Val Val Thr Asn Lys Lys Gly Lys Gly Pro Leu Leu Arg Pro
            100                 105                 110

Tyr Pro Asp Trp Ser Phe Ala Lys Tyr Glu Asp Cys Ser Gly Ile Val
            115                 120                 125

Ser Ala Phe Lys Ile Ala Val Asp Lys Phe Asp Arg Leu Trp Val Leu
        130                 135                 140

Asp Ser Gly Leu Val Asn Asn Asn Gln Pro Met Cys Ser Pro Lys Leu
145                 150                 155                 160

Leu Thr Phe Asp Leu Lys Thr Ser Lys Leu Val Lys Gln Val Glu Ile
                165                 170                 175

Pro His Asn Ile Ala Val Asn Ala Thr Thr Gly Met Gly Glu Leu Val
            180                 185                 190

Ser Leu Ala Val Gln Ala Ile Asp Arg Thr Asn Thr Met Val Tyr Ile
            195                 200                 205

Ala Asp Glu Lys Gly Glu Gly Leu Ile Met Tyr Gln Asn Ser Asp Asp
        210                 215                 220

Ser Phe His Arg Leu Thr Ser Asn Thr Phe Asp Tyr Asp Pro Arg Tyr
```

```
                225                 230                 235                 240
Thr Lys Leu Thr Val Ala Gly Glu Ser Phe Thr Val Lys Asn Gly Ile
                245                 250                 255
Tyr Gly Ile Ala Leu Ser Pro Val Thr Asn Asn Leu Tyr Tyr Ser Pro
                260                 265                 270
Leu Leu Ser His Gly Leu Tyr Tyr Val Asp Thr Glu Gln Phe Ser Asn
                275                 280                 285
Pro Gln Tyr Glu Glu Asn Asn Val Gln Tyr Glu Gly Ser Gln Asp Ile
                290                 295                 300
Leu Asn Thr Gln Ser Phe Gly Lys Val Ser Lys Asn Gly Val Leu
305                 310                 315                 320
Phe Leu Gly Leu Val Gly Asn Ser Gly Ile Ala Cys Val Asn Glu His
                325                 330                 335
Gln Val Leu Gln Arg Glu Ser Phe Asp Val Val Ala Gln Asn Glu Glu
                340                 345                 350
Thr Leu Gln Met Ile Val Ser Met Lys Ile Met Glu Asn Leu Pro Gln
                355                 360                 365
Ser Gly Arg Ile Asn Asp Pro Glu Gly Asn Glu Tyr Met Leu Ala Leu
                370                 375                 380
Ser Asn Arg Met Gln Lys Ile Ile Asn Asn Asp Phe Asn Phe Asn Asp
385                 390                 395                 400
Val Asn Phe Arg Ile Leu Gly Ala Asn Val Asp Asp Leu Met Arg Asn
                405                 410                 415
Thr Arg Cys Gly Arg Tyr His Asn Gln Asn Ala Gly Asn Gln Asn Ala
                420                 425                 430
Asp Asn Gln Asn Ala Asp Asn Gln Asn Ala Asn Asn Gln Asn Ala Asp
                435                 440                 445
Asn Gln Asn Ala Asn Lys Gln Asn Gly Asn Arg Gln Asn Asp Asn Arg
                450                 455                 460
Gln Asn Asp Asn Lys Gln Asn Gly Asn Arg Gln Asn Asp Asn Lys Gln
465                 470                 475                 480
Asn Gly Asn Arg Gln Asn Asp Asn Lys Gln Asn Gly Asn Arg Gln Asn
                485                 490                 495
Gly Asn Lys Gln Asn Asp Asn Lys Gln Asn Gly Asn Arg Gln Asn Asp
                500                 505                 510
Asn Lys Arg Asn Gly Asn Arg Gln Asn Asp Asn Gln Asn Asn Gln Asn
                515                 520                 525
Asp Asn Asn Arg Asn Asp Asn Gln Val His His Ser Ser Lys Leu His
530                 535                 540

<210> SEQ ID NO 4
<211> LENGTH: 464
<212> TYPE: PRT
<213> ORGANISM: Apis mellifera

<400> SEQUENCE: 4

Met Thr Lys Trp Leu Leu Leu Met Val Cys Leu Gly Ile Ala Cys Gln
1               5                   10                  15
Asn Ile Arg Gly Gly Val Val Arg Glu Asn Ser Ser Gly Lys Asn Leu
                20                  25                  30
Thr Asn Thr Leu Asn Val Ile His Lys Trp Lys Tyr Leu Asp Tyr Asp
                35                  40                  45
Phe Asp Asn Asp Glu Arg Arg Gln Ala Ala Ile Gln Ser Gly Glu Tyr
                50                  55                  60
```

Asp Arg Thr Lys Asn Tyr Pro Leu Asp Val Asp Gln Trp His Asn Lys
65                  70                  75                  80

Thr Phe Leu Ala Val Ile Arg Tyr Asn Gly Val Pro Ser Ser Leu Asn
            85                  90                  95

Val Val Ser Asp Lys Thr Gly Asn Gly Gly Arg Leu Leu Gln Pro Tyr
        100                 105                 110

Pro Asp Trp Ser Phe Ala Lys Tyr Glu Asp Cys Ser Gly Ile Val Ser
    115                 120                 125

Ala His Lys Ile Ala Ile Asp Glu Tyr Glu Arg Leu Trp Val Leu Asp
130                 135                 140

Ser Gly Leu Val Asn Asn Thr Gln Pro Met Cys Ser Pro Lys Leu Phe
145                 150                 155                 160

Ala Phe Asp Leu Asn Thr Ser Gln Leu Leu Lys Gln Val Glu Ile Pro
                165                 170                 175

His Asp Val Ala Thr Thr Gly Lys Gly Glu Leu Val Ser Leu Thr Val
            180                 185                 190

Gln Ala Met Asp Ser Thr Asn Thr Met Val Tyr Met Val Asp Asn Lys
        195                 200                 205

Asn Thr Leu Ile Ile Tyr Gln Asn Ala Asp Asp Ser Phe His Arg Leu
    210                 215                 220

Ser Ser His Thr Leu Asn His Asn Ser Asp Lys Met Ser Asp Gln Gln
225                 230                 235                 240

Glu Asn Leu Thr Leu Lys Glu Val Asp Asn Lys Val Tyr Gly Met Ala
                245                 250                 255

Leu Ser Pro Val Thr His Asn Leu Tyr Tyr Asn Ser Pro Ser Ser Glu
            260                 265                 270

Asn Leu Tyr Tyr Val Asn Thr Glu Ser Leu Met Lys Ser Glu Asn Gln
        275                 280                 285

Gly Asn Asp Val Gln Tyr Glu Arg Val Gln Asp Val Phe Asp Ser Gln
    290                 295                 300

Leu Thr Val Lys Ala Val Ser Lys Asn Gly Val Leu Leu Phe Gly Leu
305                 310                 315                 320

Ala Asn Asn Thr Leu Ser Cys Trp Asn Glu His Gln Ser Leu Asp Arg
                325                 330                 335

Gln Asn Ile Asp Val Val Ala Arg Asn Glu Asp Thr Leu Gln Met Val
            340                 345                 350

Val Ser Met Lys Ile Lys Gln Asn Val Pro Gln Ser Gly Arg Val Asn
        355                 360                 365

Asn Thr Gln Arg Asn Glu Tyr Leu Leu Ala Leu Ser Asp Arg Asn Gln
    370                 375                 380

Asn Val Leu Asn Asn Asp Leu Asn Leu Glu His Val Asn Phe Gln Ile
385                 390                 395                 400

Leu Gly Ala Asn Val Asn Asp Leu Ile Arg Asn Ser Arg Cys Ala Asn
                405                 410                 415

Phe Asp Asn Gln Asp Asn Asn His Tyr Asn His Asn His Asn Gln Ala
            420                 425                 430

Arg His Ser Ser Lys Ser Asp Asn Gln Asn Asn Asn Gln His Asn Asp
        435                 440                 445

Gln Ala His His Ser Ser Lys Ser Asn Asn Arg His Asn Asn Asn Asp
    450                 455                 460

<210> SEQ ID NO 5
<211> LENGTH: 598
<212> TYPE: PRT

-continued

<213> ORGANISM: Apis mellifera

<400> SEQUENCE: 5

```
Met Thr Thr Trp Leu Leu Val Val Cys Leu Gly Ile Ala Cys Gln
1               5                   10                  15

Gly Ile Thr Ser Val Thr Val Arg Glu Asn Ser Pro Arg Lys Leu Ala
            20                  25                  30

Asn Ser Met Asn Val Ile His Glu Trp Lys Tyr Leu Asp Tyr Asp Phe
        35                  40                  45

Gly Ser Asp Glu Arg Arg Gln Ala Ala Met Gln Ser Gly Glu Tyr Asp
    50                  55                  60

His Thr Lys Asn Tyr Pro Phe Asp Val Asp Gln Trp Arg Gly Met Thr
65                  70                  75                  80

Phe Val Thr Val Pro Arg Tyr Lys Gly Val Pro Ser Ser Leu Asn Val
                85                  90                  95

Ile Ser Glu Lys Ile Gly Asn Gly Arg Leu Leu Gln Pro Tyr Pro
            100                 105                 110

Asp Trp Ser Trp Ala Asn Tyr Lys Asp Cys Ser Gly Ile Val Ser Ala
            115                 120                 125

Tyr Lys Ile Ala Ile Asp Lys Phe Asp Arg Leu Trp Ile Leu Asp Ser
    130                 135                 140

Gly Ile Ile Asn Asn Thr Gln Pro Met Cys Ser Pro Lys Leu His Val
145                 150                 155                 160

Phe Asp Leu Asn Thr Ser His Gln Leu Lys Gln Val Val Met Pro His
                165                 170                 175

Asp Ile Ala Val Asn Ala Ser Thr Gly Asn Gly Leu Val Ser Leu
            180                 185                 190

Val Val Gln Ala Met Asp Pro Val Asn Thr Ile Val Tyr Met Ala Asp
    195                 200                 205

Asp Lys Gly Asp Ala Leu Ile Val Tyr Gln Asn Ser Asp Glu Ser Phe
210                 215                 220

His Arg Leu Thr Ser Asn Thr Phe Asp Tyr Asp Pro Lys Tyr Ile Lys
225                 230                 235                 240

Met Met Asp Ala Gly Glu Ser Phe Thr Ala Gln Asp Gly Ile Phe Gly
                245                 250                 255

Met Ala Leu Ser Pro Met Thr Asn Asn Leu Tyr Tyr Ser Pro Leu Ser
            260                 265                 270

Ser Arg Ser Leu Tyr Tyr Val Asn Thr Lys Pro Phe Met Lys Ser Glu
    275                 280                 285

Tyr Gly Ala Asn Asn Val Gln Tyr Gln Gly Val Gln Asp Ile Phe Asn
290                 295                 300

Thr Glu Ser Ile Ala Lys Ile Met Ser Lys Asn Gly Val Leu Phe Phe
305                 310                 315                 320

Gly Leu Met Asn Ser Ala Ile Gly Cys Trp Asn Glu His Gln Pro
                325                 330                 335

Leu Gln Arg Glu Asn Met Asp Met Val Ala Gln Asn Glu Thr Leu
            340                 345                 350

Gln Thr Val Val Ala Met Lys Met Met His Leu Pro Gln Ser Asn Lys
    355                 360                 365

Met Asn Arg Met His Arg Met Asn Arg Val Asn Arg Val Asn Arg Met
370                 375                 380

Asp Arg Met Asp Arg Ile Asp Arg Met Asp Arg Met Asp Arg Met Asp
385                 390                 395                 400
```

Thr Met Asp Thr Met Asp Arg Ile Asp Arg Met Asp Arg
                405                 410                 415

Ile Asp Arg Ile Asp Arg Met His Thr Met Thr Asp Thr Met
            420                 425                 430

Asp Arg Thr Asp Lys Met Ser Ser Met Asp Arg Met Asp Arg Met Asp
            435                 440                 445

Arg Val Asp Arg Met Asp Thr Met Asp Arg Thr Asp Lys Met Ser Ser
    450                 455                 460

Met Asp Arg Met Asp Arg Met Asp Arg Val Asp Thr Met Asp Thr Met
465                 470                 475                 480

Asp Thr Met Asp Arg Met Asp Arg Met Asp Arg Met Asp Arg Met Asp
                485                 490                 495

Arg Met Asp Arg Met Asp Thr Met Asp Arg Thr Asp Lys Met Ser Arg
                500                 505                 510

Ile Asp Arg Met Asp Lys Ile Asp Arg Met Asp Arg Met Asp Arg Thr
            515                 520                 525

Asn Arg Met Asp Arg Met Asn Arg Met Asn Arg Gln Met Asn Glu Tyr
    530                 535                 540

Met Met Ala Leu Ser Met Lys Leu Gln Lys Phe Ile Asn Asn Asp Tyr
545                 550                 555                 560

Asn Phe Asn Glu Val Asn Phe Arg Ile Leu Gly Ala Asn Val Asn Asp
                565                 570                 575

Leu Ile Met Asn Thr Arg Cys Ala Asn Ser Asp Asn Gln Asn Asn
                580                 585                 590

Gln Asn Lys His Asn Asn
        595

<210> SEQ ID NO 6
<211> LENGTH: 437
<212> TYPE: PRT
<213> ORGANISM: Apis mellifera

<400> SEQUENCE: 6

Met Thr Asn Trp Leu Leu Leu Ile Val Cys Leu Ser Ile Ala Cys Gln
1               5                   10                  15

Asp Val Thr Ser Ala Ile His Gln Arg Lys Ser Ser Lys Asn Leu Glu
                20                  25                  30

His Ser Met Asn Val Ile His Glu Trp Lys Tyr Ile Asp Tyr Asp Phe
            35                  40                  45

Gly Ser Asp Glu Lys Arg Gln Ala Ala Ile Gln Ser Gly Glu Tyr Asp
    50                  55                  60

Tyr Thr Lys Asn Tyr Pro Phe Asp Val Asp Gln Trp His Asn Lys Thr
65                  70                  75                  80

Phe Leu Ala Val Ile Arg Tyr Asp Gly Val Pro Ser Ser Leu Asn Val
                85                  90                  95

Ile Ser Glu Lys Ile Gly Asn Gly Gly Cys Leu Leu Gln Pro Tyr Pro
                100                 105                 110

Asp Trp Ser Trp Ala Asn Tyr Lys Asp Cys Ser Gly Ile Val Ser Ala
            115                 120                 125

Tyr Lys Ile Ala Ile Asp Lys Phe Asp Arg Leu Trp Val Leu Asp Ser
    130                 135                 140

Gly Leu Ile Asn Asn Ile Gln Leu Met Cys Ser Pro Lys Leu Leu Ala
145                 150                 155                 160

Phe Asp Leu Asn Thr Ser Lys Leu Leu Lys Gln Ile Glu Ile Pro His
                165                 170                 175

Asn Ile Ala Val Asn Ala Ser Thr Gly Met Gly Pro Val Ser Leu
            180                 185                 190

Val Val Gln Ala Met Asp Pro Met Asn Thr Thr Val Tyr Ile Ala Asp
            195                 200                 205

Asp Arg Gly Asp Ala Leu Ile Ile Tyr Gln Asn Ser Asp Asp Ser Phe
            210                 215                 220

His Arg Leu Thr Ser Lys Thr Phe Asp Asn Asp Leu Arg Tyr Ser Glu
225                 230                 235                 240

Leu Ala Val Ala Gly Glu Ser Phe Thr Val His Asp Gly Ile Phe Gly
            245                 250                 255

Met Ala Leu Ser Pro Val Thr Asn Asn Leu Tyr Tyr Ser Pro Leu Thr
            260                 265                 270

Ser His Ser Leu Tyr Tyr Val Asn Met Glu Pro Phe Met Lys Ser Gln
            275                 280                 285

Tyr Glu Glu Asn Asn Ile Glu Tyr Glu Gly Ile Gln Asp Ile Phe Asn
            290                 295                 300

Thr Gln Ser Ser Ala Lys Val Met Ser Lys Asn Gly Val Leu Phe Phe
305                 310                 315                 320

Gly Leu Val Asn Asn Ser Ala Ile Gly Cys Trp Asn Glu His Gln Pro
            325                 330                 335

Leu Gln Arg Gln Asn Met Asp Met Val Ala Gln Asn Glu Lys Thr Leu
            340                 345                 350

Gln Met Ile Ile Ser Val Lys Ile Ile Gln Asn Leu Ala Tyr Ser Gly
            355                 360                 365

Arg Met Asn Arg Ile His Lys Asn Glu Tyr Met Leu Ala Leu Ser Asn
            370                 375                 380

Arg Met Gln Lys Ile Val Asn Asn Asp Phe Asn Phe Asp Glu Val Asn
385                 390                 395                 400

Phe Arg Ile Leu Gly Ala Asn Val Asn Leu Ile Lys Asn Thr Arg
            405                 410                 415

Cys Ala Lys Ser Asn Asn Gln Asn Asn Asn Gln Asn Lys Tyr Lys Asn
            420                 425                 430

Gln Ala His Leu Asp
            435

<210> SEQ ID NO 7
<211> LENGTH: 443
<212> TYPE: PRT
<213> ORGANISM: Apis mellifera

<400> SEQUENCE: 7

Met Thr Arg Trp Leu Phe Met Val Ala Cys Leu Gly Ile Ala Cys Gln
1               5                   10                  15

Gly Ala Ile Leu Arg Glu Asn Ser Ala Arg Asn Leu Lys Asn Ser Leu
            20                  25                  30

Lys Val Met His Glu Trp Lys Tyr Ile Asp Tyr Asp Phe Gly Ser Glu
            35                  40                  45

Glu Lys Arg Gln Ala Ala Ile Gln Ser Asp Glu Tyr Asp His Thr Lys
            50                  55                  60

Asn Tyr Pro Phe Asp Val Asp Gln Trp Arg Asp Lys Thr Phe Val Thr
65                  70                  75                  80

Val Leu Arg Tyr Asp Gly Val Pro Ser Ser Leu Asn Val Ile Ser Glu
            85                  90                  95

Lys Thr Gly Asn Gly Gly Arg Leu Leu Gln Pro Tyr Pro Asp Trp Ser

```
            100                 105                 110
Trp Thr Lys Tyr Lys Asp Cys Ser Gly Ile Val Ser Ala Tyr Ser Ile
        115                 120                 125
Ala Ile Asp Lys Phe Asp Arg Leu Trp Val Leu Asp Ser Gly Leu Val
    130                 135                 140
Asn Asn Thr Gln Pro Met Cys Phe Pro Lys Leu Leu Val Phe Asp Leu
145                 150                 155                 160
Asn Ser Ser Gln Leu Ile Lys Gln Val Asp Ile Pro His Glu Ile Ala
                165                 170                 175
Val Asn Thr Thr Thr Glu Gln Gly Arg Leu Lys Ser Leu Ala Val Gln
            180                 185                 190
Ala Ile Ser Ser Val Asn Thr Leu Val Tyr Ile Ala Asp Asn Lys Gly
        195                 200                 205
Asp Gly Leu Ile Val Tyr Gln Asn Ser Asp Ser Phe His Arg Leu
    210                 215                 220
Thr Ser Asn Thr Phe Asn Tyr Asp Pro Arg Tyr Thr Lys Met Thr Val
225                 230                 235                 240
Glu Gly Glu Ser Phe Thr Val Gln Asp Gly Ile Tyr Gly Met Ala Leu
                245                 250                 255
Ser Pro Met Thr Asn Asn Leu Tyr Tyr Ser Pro Leu Ala Ser Arg Asp
            260                 265                 270
Leu Tyr Tyr Val Asn Thr Lys Pro Phe Ile Lys Ser Glu Tyr Gly Glu
        275                 280                 285
Asn Lys Val Gln Tyr Asn Gly Val Gln Asp Val Phe Asn Thr Gln Thr
    290                 295                 300
Thr Ala Lys Ala Val Ser Lys Asn Gly Ile Leu Phe Phe Gly Leu Val
305                 310                 315                 320
Asn Asn Thr Ala Val Gly Cys Trp Asn Glu His Gln Thr Leu Gln Arg
                325                 330                 335
Glu Asn Thr Asp Met Val Ala Gln Asn Glu Glu Thr Leu Gln Met Ile
            340                 345                 350
Val Gly Met Lys Ile Lys Gln Leu Leu Pro His Ile Val Ile Ile Asp
        355                 360                 365
Ile Asp Asn Ile Ile Asn Asp Glu Tyr Met Leu Val Leu Thr Asn Arg
    370                 375                 380
Met Gln Lys Ile Leu Asn Asn Asp Leu Asn Phe Asn Asp Ile Asn Phe
385                 390                 395                 400
Arg Ile Leu Ile Gly Gly Val Ser Asp Leu Leu Glu Asn Thr Arg Cys
                405                 410                 415
Thr Asn Phe Asn Ile Gln Asn Asp Asp Ser Asp Glu Asn Asn Asp Asp
            420                 425                 430
Ser Ile Arg Ile Thr Ile Asp Ala Ser Phe Asn
        435                 440

<210> SEQ ID NO 8
<211> LENGTH: 416
<212> TYPE: PRT
<213> ORGANISM: Apis mellifera

<400> SEQUENCE: 8

Met Ile Arg Trp Leu Leu Met Tyr Leu Gly Ile Thr Cys Gln Gly
1               5                   10                  15

Val Thr Asp Ile His Ser Arg Asn Leu Thr Asn Ser Leu Lys Val Ile
            20                  25                  30
```

```
Tyr Glu Trp Lys Tyr Ile Asp Tyr Asp Phe Gly Ser Asp Glu Lys Arg
             35                  40                  45

Gln Ala Ala Ile Gln Ser Gly Asp Tyr Asn Tyr Thr Met Asn Tyr Leu
 50                  55                  60

Leu Asp Thr Asp Gln Trp Gly Asp Lys Thr Phe Val Ile Ile Met Lys
65                  70                  75                  80

Phe Asn Gly Val Pro Ser Ser Leu Asn Val Ile Thr Asn Lys Thr Gly
                 85                  90                  95

Asn Gly Gly Pro Leu Leu Ala Pro Tyr Pro Asp Trp Thr Trp Ala Lys
            100                 105                 110

Asn Glu Asn Cys Ser Gly Ile Thr Ser Ala Tyr Lys Ile Glu Ile Asp
            115                 120                 125

Met Cys Asp Arg Leu Trp Val Leu Asp Ser Gly Leu Ile Asn Asn Val
130                 135                 140

Arg Ser Val Cys Pro Pro Gln Leu Leu Val Phe Asp Leu Asn Thr Ser
145                 150                 155                 160

Gln Leu Leu Lys Gln Val Lys Ile Pro His Asp Ile Ala Val Asn Thr
                165                 170                 175

Thr Thr Glu Lys Gly Ala Leu Val Thr Leu Ser Val Gln Leu Leu Ser
            180                 185                 190

Cys Glu Val Asn Gly Ser Thr Leu Val Tyr Ile Gly Asp Asn Glu Gly
            195                 200                 205

Phe Ala Leu Ile Ile Tyr Asn Asn Ser Asp Asn Ser Phe Gln Arg Leu
            210                 215                 220

Thr Ser Ser Thr Phe Ala Ser Asp Pro Arg Tyr Thr Thr Phe Thr Ile
225                 230                 235                 240

Asn Gly Glu Ser Phe Thr Leu Gln Ser Gly Ile Phe Gly Met Ala Leu
                245                 250                 255

Ser Pro Leu Thr Gln Asn Leu Tyr Tyr Ser Ala Leu Ser Ser His Asn
            260                 265                 270

Leu Asn Tyr Val Asn Thr Glu Gln Phe Val Lys Ser Gln Tyr Gln Ala
            275                 280                 285

Asn Asn Val His Tyr Gln Gly Lys Glu Asn Ile Leu Trp Thr Gln Ala
            290                 295                 300

Ser Ala Lys Gly Ile Ser Asp Asn Gly Val Leu Phe Phe Gly Leu Val
305                 310                 315                 320

Gly Asp Thr Ser Leu Ala Cys Trp Asn Glu Asn Arg Leu Leu Asp Arg
                325                 330                 335

Arg Asn Ile Glu Val Val Ala Lys Asn Lys Glu Thr Leu Gln Ala Ile
            340                 345                 350

Thr Gly Leu Lys Val Lys Arg Arg Ile Ser Phe Ile Leu Val His Gly
            355                 360                 365

Phe Pro Leu Glu Tyr Glu Tyr Val Leu Ala Val Ser Asn Arg Ile Gln
370                 375                 380

Lys Val Ile Tyr Gly Phe Asp Phe Asn Asp Val Asn Phe Arg Ile Leu
385                 390                 395                 400

Ile Ala Asn Val Asn Asp Leu Ile Lys Asn Thr Arg Cys Ile Ser Pro
                405                 410                 415
```

<210> SEQ ID NO 9
<211> LENGTH: 423
<212> TYPE: PRT
<213> ORGANISM: Apis mellifera

<400> SEQUENCE: 9

```
Met Ser Phe Asn Ile Trp Trp Leu Ile Leu Tyr Phe Ser Ile Val Cys
1               5                   10                  15

Gln Ala Lys Ala His Tyr Ser Leu Arg Asp Phe Lys Ala Asn Ile Phe
                20                  25                  30

Gln Val Lys Tyr Gln Trp Lys Tyr Phe Asp Tyr Asn Phe Gly Ser Asp
            35                  40                  45

Glu Lys Arg Gln Ala Ala Ile Gln Ser Gly Glu Tyr Asn Tyr Lys Asn
        50                  55                  60

Asn Val Pro Ile Asp Val Asp Arg Trp Asn Gly Lys Thr Phe Val Thr
65                  70                  75                  80

Ile Leu Arg Asn Asp Gly Val Pro Ser Ser Leu Asn Val Ile Ser Asn
                85                  90                  95

Lys Ile Gly Asn Gly Gly Pro Leu Leu Glu Pro Tyr Pro Asn Trp Ser
                100                 105                 110

Trp Ala Lys Asn Gln Asn Cys Ser Gly Ile Thr Ser Val Tyr Arg Ile
            115                 120                 125

Ala Ile Asp Glu Trp Asp Arg Leu Trp Val Leu Asp Asn Gly Ile Ser
        130                 135                 140

Gly Glu Thr Ser Val Cys Pro Ser Gln Ile Val Val Phe Asp Leu Lys
145                 150                 155                 160

Asn Ser Lys Leu Leu Lys Gln Val Lys Ile Pro His Asp Ile Ala Ile
                165                 170                 175

Asn Ser Thr Thr Gly Lys Arg Asn Val Val Thr Pro Ile Val Gln Ser
            180                 185                 190

Phe Asp Tyr Asn Asn Thr Trp Val Tyr Ile Ala Asp Val Glu Gly Tyr
        195                 200                 205

Ala Leu Ile Ile Tyr Asn Asn Ala Asp Asp Ser Phe Gln Arg Leu Thr
        210                 215                 220

Ser Ser Thr Phe Val Tyr Asp Pro Arg Tyr Thr Lys Tyr Thr Ile Asn
225                 230                 235                 240

Asp Glu Ser Phe Ser Leu Gln Asp Gly Ile Leu Gly Met Ala Leu Ser
                245                 250                 255

His Lys Thr Gln Asn Leu Tyr Tyr Ser Ala Met Ser Ser His Asn Leu
            260                 265                 270

Asn Tyr Val Asn Thr Lys Gln Phe Thr Gln Gly Lys Phe Gln Ala Asn
        275                 280                 285

Asp Ile Gln Tyr Gln Gly Ala Ser Asp Ile Leu Trp Thr Gln Ala Ser
        290                 295                 300

Ala Lys Ala Ile Ser Glu Thr Gly Ala Leu Phe Phe Gly Leu Val Ser
305                 310                 315                 320

Asp Thr Ala Leu Gly Cys Trp Asn Glu Asn Arg Pro Leu Lys Arg Arg
            325                 330                 335

Asn Ile Glu Ile Val Ala Lys Asn Asn Asp Thr Leu Gln Phe Ile Ser
        340                 345                 350

Gly Ile Lys Ile Ile Lys Gln Ile Ser Ser Asn Ile Tyr Glu Arg Gln
        355                 360                 365

Asn Asn Glu Tyr Ile Trp Ile Val Ser Asn Lys Tyr Gln Lys Ile Ala
370                 375                 380

Asn Gly Asp Leu Asn Phe Asn Glu Val Asn Phe Arg Ile Leu Asn Ala
385                 390                 395                 400

Pro Val Asn Gln Leu Ile Arg Tyr Thr Arg Cys Glu Asn Pro Lys Thr
                405                 410                 415
```

```
Asn Phe Phe Ser Ile Phe Leu
            420

<210> SEQ ID NO 10
<211> LENGTH: 6
<212> TYPE: PRT
<213> ORGANISM: Artificial sequence
<220> FEATURE:
<223> OTHER INFORMATION: Major royal jelly protein fragment

<400> SEQUENCE: 10

Lys Ile Ser Ile His Leu
1               5

<210> SEQ ID NO 11
<211> LENGTH: 8
<212> TYPE: PRT
<213> ORGANISM: Artificial sequence
<220> FEATURE:
<223> OTHER INFORMATION: Major royal jelly protein fragment

<400> SEQUENCE: 11

Lys Asn Asn Asn Gln Asn Asp Asn
1               5

<210> SEQ ID NO 12
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 12

Lys Leu His
1

<210> SEQ ID NO 13
<211> LENGTH: 10
<212> TYPE: PRT
<213> ORGANISM: Artificial sequence
<220> FEATURE:
<223> OTHER INFORMATION: Major royal jelly protein fragment

<400> SEQUENCE: 13

Lys Ser Asn Asn Arg His Asn Asn Asn Asp
1               5                   10

<210> SEQ ID NO 14
<211> LENGTH: 4
<212> TYPE: PRT
<213> ORGANISM: Artificial sequence
<220> FEATURE:
<223> OTHER INFORMATION: Major royal jelly protein fragment

<400> SEQUENCE: 14

Lys His Asn Asn
1

<210> SEQ ID NO 15
<211> LENGTH: 7
<212> TYPE: PRT
<213> ORGANISM: Artificial sequence
<220> FEATURE:
<223> OTHER INFORMATION: Major royal jelly protein fragment

<400> SEQUENCE: 15

Lys Asn Gln Ala His Leu Asp
```

-continued

```
<210> SEQ ID NO 16
<211> LENGTH: 8
<212> TYPE: PRT
<213> ORGANISM: Artificial sequence
<220> FEATURE:
<223> OTHER INFORMATION: Major royal jelly protein fragment

<400> SEQUENCE: 16

Lys Asn Thr Arg Cys Ile Ser Pro
1               5

<210> SEQ ID NO 17
<211> LENGTH: 9
<212> TYPE: PRT
<213> ORGANISM: Artificial sequence
<220> FEATURE:
<223> OTHER INFORMATION: Major royal jelly protein fragment

<400> SEQUENCE: 17

Lys Thr Asn Phe Phe Ser Ile Phe Leu
1               5

<210> SEQ ID NO 18
<211> LENGTH: 8
<212> TYPE: PRT
<213> ORGANISM: Artificial sequence
<220> FEATURE:
<223> OTHER INFORMATION: Major royal jelly protein fragment

<400> SEQUENCE: 18

Pro Phe Lys Ile Ser Ile His Leu
1               5

<210> SEQ ID NO 19
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (8)..(8)
<223> OTHER INFORMATION: CARBOXYL TERMINUS

<400> SEQUENCE: 19

Pro Phe Lys Ile Ser Ile His Leu
1               5

<210> SEQ ID NO 20
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: CARBOXYL TERMINUS

<400> SEQUENCE: 20
```

```
Lys Ile Ser Ile His Leu
1               5

<210> SEQ ID NO 21
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: CARBOXYL TERMINUS

<400> SEQUENCE: 21

Lys Ile Ser Ile
1

<210> SEQ ID NO 22
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: CARBOXYL TERMINUS

<400> SEQUENCE: 22

Pro Phe Lys Ile
1

<210> SEQ ID NO 23
<211> LENGTH: 10
<212> TYPE: PRT
<213> ORGANISM: Artificial sequence
<220> FEATURE:
<223> OTHER INFORMATION: Major royal jelly protein fragment

<400> SEQUENCE: 23

Asn Gln Lys Asn Asn Asn Gln Asn Asp Asn
1               5                   10

<210> SEQ ID NO 24
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (10)..(10)
<223> OTHER INFORMATION: CARBOXYL TERMINUS

<400> SEQUENCE: 24

Asn Gln Lys Asn Asn Asn Gln Asn Asp Asn
1               5                   10
```

```
<210> SEQ ID NO 25
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (8)..(8)
<223> OTHER INFORMATION: CARBOXYL TERMINUS

<400> SEQUENCE: 25

Asn Gln Lys Asn Asn Asn Gln Asn
1               5

<210> SEQ ID NO 26
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: CARBOXYL TERMINUS

<400> SEQUENCE: 26

Asn Gln Lys Asn Asn Asn
1               5

<210> SEQ ID NO 27
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: CARBOXYL TERMINUS

<400> SEQUENCE: 27

Asn Gln Lys Asn
1

<210> SEQ ID NO 28
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: CARBOXYL TERMINUS
```

```
<400> SEQUENCE: 28

Lys Asn
1

<210> SEQ ID NO 29
<211> LENGTH: 7
<212> TYPE: PRT
<213> ORGANISM: Artificial sequence
<220> FEATURE:
<223> OTHER INFORMATION: Major royal jelly protein fragment

<400> SEQUENCE: 29

His His Ser Ser Lys Leu His
1               5

<210> SEQ ID NO 30
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: CARBOXYL TERMINUS

<400> SEQUENCE: 30

His Ser Ser Lys Leu His
1               5

<210> SEQ ID NO 31
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: CARBOXYL TERMINUS

<400> SEQUENCE: 31

Ser Lys Leu His
1

<210> SEQ ID NO 32
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(3)
<223> OTHER INFORMATION: CARBOXYL TERMINUS
<220> FEATURE:
<221> NAME/KEY: MISC_FEATURE
<222> LOCATION: (2)..(2)
```

```
<223> OTHER INFORMATION: CARBOXYL TERMINUS

<400> SEQUENCE: 32

Ser Lys
1

<210> SEQ ID NO 33
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: CARBOXYL TERMINUS

<400> SEQUENCE: 33

His Ser Ser Lys
1

<210> SEQ ID NO 34
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: CARBOXYL TERMINUS

<400> SEQUENCE: 34

Ser Ser Lys Ser
1

<210> SEQ ID NO 35
<211> LENGTH: 13
<212> TYPE: PRT
<213> ORGANISM: Artificial sequence
<220> FEATURE:
<223> OTHER INFORMATION: Major royal jelly protein fragment

<400> SEQUENCE: 35

His Ser Ser Lys Ser Asn Asn Arg His Asn Asn Asn Asp
1               5                   10

<210> SEQ ID NO 36
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (12)..(12)
<223> OTHER INFORMATION: CARBOXYL TERMINUS

<400> SEQUENCE: 36
```

```
Ser Ser Lys Ser Asn Asn Arg His Asn Asn Asp
1               5                   10

<210> SEQ ID NO 37
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (10)..(10)
<223> OTHER INFORMATION: CARBOXYL TERMINUS

<400> SEQUENCE: 37

Ser Ser Lys Ser Asn Asn Arg His Asn Asn
1               5                   10

<210> SEQ ID NO 38
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (8)..(8)
<223> OTHER INFORMATION: CARBOXYL TERMINUS

<400> SEQUENCE: 38

Ser Ser Lys Ser Asn Asn Arg His
1               5

<210> SEQ ID NO 39
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: CARBOOXYL TERMINUS
<220> FEATURE:
<221> NAME/KEY: MISC_FEATURE
<222> LOCATION: (6)..(6)
<223> OTHER INFORMATION: CARBOXYL TERMINUS

<400> SEQUENCE: 39

Ser Ser Lys Ser Asn Asn
1               5

<210> SEQ ID NO 40
<211> LENGTH: 4
<212> TYPE: PRT
<213> ORGANISM: Artificial sequence
<220> FEATURE:
<223> OTHER INFORMATION: Synthetic peptide
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: CARBOXYL TERMINUS

<400> SEQUENCE: 40

Ser Ser Lys Ser
1

<210> SEQ ID NO 41
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: CARBOXYL TERMINUS

<400> SEQUENCE: 41

Lys Ser
1

<210> SEQ ID NO 42
<211> LENGTH: 6
<212> TYPE: PRT
<213> ORGANISM: Artificial sequence
<220> FEATURE:
<223> OTHER INFORMATION: Major royal jelly protein fragment

<400> SEQUENCE: 42

Gln Asn Lys His Asn Asn
1               5

<210> SEQ ID NO 43
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: CARBOXYL TERMINUS

<400> SEQUENCE: 43

Gln Asn Lys His Asn Asn
1               5

<210> SEQ ID NO 44
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MISC_FEATURE
<222> LOCATION: (4)..(4)
<223> OTHER INFORMATION: CARBOXYL TERMINUS

<400> SEQUENCE: 44

Lys His Asn Asn
1

<210> SEQ ID NO 45
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: CARBOXYL TERMINUS

<400> SEQUENCE: 45

Lys His
1

<210> SEQ ID NO 46
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: CARBOXYL TERMINUS

<400> SEQUENCE: 46

Gln Asn Lys His
1

<210> SEQ ID NO 47
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 47

Met His Arg
1

<210> SEQ ID NO 48
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
```

```
<223> OTHER INFORMATION: CARBOXYL TERMINUS

<400> SEQUENCE: 48

Leu Val Lys
1

<210> SEQ ID NO 49
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: AMIDATION

<400> SEQUENCE: 49

Leu Val Lys
1

<210> SEQ ID NO 50
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 50

Phe Asp Arg
1

<210> SEQ ID NO 51
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 51

Leu Ile Arg
1

<210> SEQ ID NO 52
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: AMIDATION

<400> SEQUENCE: 52

Leu Ile Arg
1

<210> SEQ ID NO 53
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 53

Phe Asp Arg
1

<210> SEQ ID NO 54
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (4)..(4)
<223> OTHER INFORMATION: CARBOXYL TERMINUS

<400> SEQUENCE: 54

His Asn Ile Arg
1

<210> SEQ ID NO 55
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 55

Leu Gln Lys
1

<210> SEQ ID NO 56
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MISC_FEATURE
<222> LOCATION: (3)..(3)
<223> OTHER INFORMATION: CARBOXYL TERMINUS

<400> SEQUENCE: 56

Leu Leu Lys
1

<210> SEQ ID NO 57
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: AMIDATION

<400> SEQUENCE: 57

Leu Leu Lys
1

<210> SEQ ID NO 58
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: CARBOXYL TERMINUS

<400> SEQUENCE: 58

Lys Ile
1

<210> SEQ ID NO 59
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: CARBOXYL TERMINUS

<400> SEQUENCE: 59

His Asn Ile Arg
1

<210> SEQ ID NO 60
<211> LENGTH: 3
<212> TYPE: PRT
<213> ORGANISM: Artificial sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXY TERMINUS

<400> SEQUENCE: 60

Phe Ala Lys
1

<210> SEQ ID NO 61
<211> LENGTH: 4
<212> TYPE: PRT
<213> ORGANISM: Artificial sequence
<220> FEATURE:
<223> OTHER INFORMATION: Major royal jelly protein fragment

<400> SEQUENCE: 61

Pro Phe Lys Ile
1

<210> SEQ ID NO 62
<211> LENGTH: 4
<212> TYPE: PRT
<213> ORGANISM: Artificial sequence
<220> FEATURE:
<223> OTHER INFORMATION: Major royal jelly protein fragment

<400> SEQUENCE: 62

Lys Ile Ser Ile
1

<210> SEQ ID NO 63
<211> LENGTH: 6
<212> TYPE: PRT
<213> ORGANISM: Artificial sequence
<220> FEATURE:
<223> OTHER INFORMATION: Major royal jelly protein fragment

<400> SEQUENCE: 63

Lys Ile Ser Ile His Leu
1               5

<210> SEQ ID NO 64
<211> LENGTH: 8
<212> TYPE: PRT
<213> ORGANISM: Artificial sequence
<220> FEATURE:
<223> OTHER INFORMATION: Major royal jelly protein fragment

<400> SEQUENCE: 64

Pro Phe Lys Ile Ser Ile His Leu
1               5

<210> SEQ ID NO 65
<211> LENGTH: 2
<212> TYPE: PRT
<213> ORGANISM: Artificial sequence
<220> FEATURE:
<223> OTHER INFORMATION: Major royal jelly protein fragment

<400> SEQUENCE: 65

Lys Asn
1
```

```
<210> SEQ ID NO 66
<211> LENGTH: 4
<212> TYPE: PRT
<213> ORGANISM: Artificial sequence
<220> FEATURE:
<223> OTHER INFORMATION: Major royal jelly protein fragment

<400> SEQUENCE: 66

Asn Gln Lys Asn
1

<210> SEQ ID NO 67
<211> LENGTH: 6
<212> TYPE: PRT
<213> ORGANISM: Artificial sequence
<220> FEATURE:
<223> OTHER INFORMATION: Major royal jelly protein fragment

<400> SEQUENCE: 67

Asn Gln Lys Asn Asn Asn
1               5

<210> SEQ ID NO 68
<211> LENGTH: 8
<212> TYPE: PRT
<213> ORGANISM: Artificial sequence
<220> FEATURE:
<223> OTHER INFORMATION: Major royal jelly protein fragment

<400> SEQUENCE: 68

Asn Gln Lys Asn Asn Asn Gln Asn
1               5

<210> SEQ ID NO 69
<211> LENGTH: 10
<212> TYPE: PRT
<213> ORGANISM: Artificial sequence
<220> FEATURE:
<223> OTHER INFORMATION: Major royal jelly protein fragment

<400> SEQUENCE: 69

Asn Gln Lys Asn Asn Asn Gln Asn Asp Asn
1               5                   10

<210> SEQ ID NO 70
<211> LENGTH: 6
<212> TYPE: PRT
<213> ORGANISM: Artificial sequence
<220> FEATURE:
<223> OTHER INFORMATION: Major royal jelly protein fragment

<400> SEQUENCE: 70

His Ser Ser Lys Leu His
1               5

<210> SEQ ID NO 71
<211> LENGTH: 4
<212> TYPE: PRT
<213> ORGANISM: Artificial sequence
<220> FEATURE:
<223> OTHER INFORMATION: Major royal jelly protein fragment

<400> SEQUENCE: 71

Ser Lys Leu His
1
```

```
<210> SEQ ID NO 72
<211> LENGTH: 2
<212> TYPE: PRT
<213> ORGANISM: Artificial sequence
<220> FEATURE:
<223> OTHER INFORMATION: Major royal jelly protein fragment

<400> SEQUENCE: 72

Ser Lys
1

<210> SEQ ID NO 73
<211> LENGTH: 4
<212> TYPE: PRT
<213> ORGANISM: Artificial sequence
<220> FEATURE:
<223> OTHER INFORMATION: Major royal jelly protein fragment

<400> SEQUENCE: 73

His Ser Ser Lys
1

<210> SEQ ID NO 74
<211> LENGTH: 4
<212> TYPE: PRT
<213> ORGANISM: Artificial sequence
<220> FEATURE:
<223> OTHER INFORMATION: Major royal jelly protein fragment

<400> SEQUENCE: 74

Ser Ser Lys Ser
1

<210> SEQ ID NO 75
<211> LENGTH: 2
<212> TYPE: PRT
<213> ORGANISM: Artificial sequence
<220> FEATURE:
<223> OTHER INFORMATION: Major royal jelly protein fragment

<400> SEQUENCE: 75

Lys Ser
1

<210> SEQ ID NO 76
<211> LENGTH: 12
<212> TYPE: PRT
<213> ORGANISM: Artificial sequence
<220> FEATURE:
<223> OTHER INFORMATION: Major royal jelly protein fragment

<400> SEQUENCE: 76

Ser Ser Lys Ser Asn Asn Arg His Asn Asn Asn Asp
1               5                   10

<210> SEQ ID NO 77
<211> LENGTH: 6
<212> TYPE: PRT
<213> ORGANISM: Artificial sequence
<220> FEATURE:
<223> OTHER INFORMATION: Major royal jelly protein fragment

<400> SEQUENCE: 77

Ser Ser Lys Ser Asn Asn
1               5

<210> SEQ ID NO 78
```

```
<211> LENGTH: 8
<212> TYPE: PRT
<213> ORGANISM: Artificial sequence
<220> FEATURE:
<223> OTHER INFORMATION: Major royal jelly protein fragment

<400> SEQUENCE: 78

Ser Ser Lys Ser Asn Asn Arg His
1               5

<210> SEQ ID NO 79
<211> LENGTH: 10
<212> TYPE: PRT
<213> ORGANISM: Artificial sequence
<220> FEATURE:
<223> OTHER INFORMATION: Major royal jelly protein fragment

<400> SEQUENCE: 79

Ser Ser Lys Ser Asn Asn Arg His Asn Asn
1               5                   10

<210> SEQ ID NO 80
<211> LENGTH: 2
<212> TYPE: PRT
<213> ORGANISM: Artificial sequence
<220> FEATURE:
<223> OTHER INFORMATION: Major royal jelly protein fragment

<400> SEQUENCE: 80

Lys His
1

<210> SEQ ID NO 81
<211> LENGTH: 6
<212> TYPE: PRT
<213> ORGANISM: Artificial sequence
<220> FEATURE:
<223> OTHER INFORMATION: Major royal jelly protein fragment

<400> SEQUENCE: 81

Gln Asn Lys His Asn Asn
1               5

<210> SEQ ID NO 82
<211> LENGTH: 4
<212> TYPE: PRT
<213> ORGANISM: Artificial sequence
<220> FEATURE:
<223> OTHER INFORMATION: Major royal jelly protein fragment

<400> SEQUENCE: 82

Lys His Asn Asn
1

<210> SEQ ID NO 83
<211> LENGTH: 4
<212> TYPE: PRT
<213> ORGANISM: Artificial sequence
<220> FEATURE:
<223> OTHER INFORMATION: Major royal jelly protein fragment

<400> SEQUENCE: 83

Gln Asn Lys His
1

<210> SEQ ID NO 84
<211> LENGTH: 3
```

```
<212> TYPE: PRT
<213> ORGANISM: Artificial sequence
<220> FEATURE:
<223> OTHER INFORMATION: Major royal jelly protein fragment

<400> SEQUENCE: 84

Leu Val Lys
1

<210> SEQ ID NO 85
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (4)..(4)
<223> OTHER INFORMATION: CARBOXYL TERMINUS

<400> SEQUENCE: 85

Tyr Ile Asn Arg
1

<210> SEQ ID NO 86
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 86

Leu Ile Arg
1

<210> SEQ ID NO 87
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: CARBOXYL TERMINUS

<400> SEQUENCE: 87

Tyr Ile Asn Arg
1

<210> SEQ ID NO 88
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
```

```
<223> OTHER INFORMATION: CARBOXYL TERMINUS

<400> SEQUENCE: 88

Phe Thr Lys
1

<210> SEQ ID NO 89
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 89

Leu Leu Lys
1

<210> SEQ ID NO 90
<211> LENGTH: 2
<212> TYPE: PRT
<213> ORGANISM: Artificial sequence
<220> FEATURE:
<223> OTHER INFORMATION: Major royal jelly protein fragment

<400> SEQUENCE: 90

Lys Ile
1

<210> SEQ ID NO 91
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 91

Phe Thr Lys
1

<210> SEQ ID NO 92
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (7)..(7)
<223> OTHER INFORMATION: CARBOXYL TERMINUS

<400> SEQUENCE: 92

Ile Phe Val Thr Met Leu Arg
1               5

<210> SEQ ID NO 93
<211> LENGTH: 7
<212> TYPE: PRT
```

```
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (7)..(7)
<223> OTHER INFORMATION: CARBOXYL TERMINUS

<400> SEQUENCE: 93

Ile Phe Val Thr Met Leu Arg
1               5

<210> SEQ ID NO 94
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 94

Met Gln Lys
1

<210> SEQ ID NO 95
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 95

Met Gln Lys
1

<210> SEQ ID NO 96
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 96

Cys Asp Arg
1
```

```
<210> SEQ ID NO 97
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 97

Cys Asp Arg
1

<210> SEQ ID NO 98
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 98

Met Thr Arg
1

<210> SEQ ID NO 99
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 99

Met Thr Arg
1

<210> SEQ ID NO 100
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Terminal amino blocked with trinitrobenzene
      sulphonic acid
<220> FEATURE:
<221> NAME/KEY: MOD_RES
<222> LOCATION: (3)..(3)
```

```
<223> OTHER INFORMATION: Terminal carboxyl modified to include
      paranitroanalide

<400> SEQUENCE: 100

Phe Ala Lys
1

<210> SEQ ID NO 101
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (5)..(5)
<223> OTHER INFORMATION: CARBOXYL TERMINUS

<400> SEQUENCE: 101

Gln Asn Asp Asn Lys
1               5

<210> SEQ ID NO 102
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: CARBOXYL TERMINUS

<400> SEQUENCE: 102

Gln Asn Asp Asn Lys
1               5

<210> SEQ ID NO 103
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (5)..(5)
<223> OTHER INFORMATION: CARBOXYL TERMINUS

<400> SEQUENCE: 103

Gln Asn Asp Asn Arg
1               5

<210> SEQ ID NO 104
<211> LENGTH: 5
<212> TYPE: PRT
<213> ORGANISM: Artificial sequence
<220> FEATURE:
<223> OTHER INFORMATION: Synthetic peptide
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: CARBOXYL TERMINUS

<400> SEQUENCE: 104

Gln Asn Asp Asn Arg
1               5

<210> SEQ ID NO 105
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (5)..(5)
<223> OTHER INFORMATION: CARBOXYL TERMINUS

<400> SEQUENCE: 105

Gln Asn Gly Asn Lys
1               5

<210> SEQ ID NO 106
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: CARBOXYL TERMINUS

<400> SEQUENCE: 106

Gln Asn Gly Asn Lys
1               5

<210> SEQ ID NO 107
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (5)..(5)
<223> OTHER INFORMATION: CARBOXYL TERMINUS

<400> SEQUENCE: 107

Gln Asn Gly Asn Arg
1               5

<210> SEQ ID NO 108
<211> LENGTH: 5
```

```
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: CARBOXYL TERMINUS

<400> SEQUENCE: 108

Gln Asn Gly Asn Arg
1               5

<210> SEQ ID NO 109
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 109

Thr Asn Arg
1

<210> SEQ ID NO 110
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 110

Thr Asn Arg
1

<210> SEQ ID NO 111
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 111

Met Asp Lys
```

```
<210> SEQ ID NO 112
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 112

Met Asp Lys
1

<210> SEQ ID NO 113
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 113

Met Asp Arg
1

<210> SEQ ID NO 114
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 114

Met Asp Arg
1

<210> SEQ ID NO 115
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
```

```
<223> OTHER INFORMATION: CARBOXYL TERMINUS

<400> SEQUENCE: 115

Thr Asp Lys
1

<210> SEQ ID NO 116
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 116

Thr Asp Lys
1

<210> SEQ ID NO 117
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 117

Ile Asp Arg
1

<210> SEQ ID NO 118
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 118

Ile Asp Arg
1

<210> SEQ ID NO 119
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
```

```
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 119

Val Asn Arg
1

<210> SEQ ID NO 120
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 120

Val Asn Arg
1

<210> SEQ ID NO 121
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 121

Met His Arg
1

<210> SEQ ID NO 122
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 122

Met His Arg
1

<210> SEQ ID NO 123
<211> LENGTH: 3
<212> TYPE: PRT
```

```
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 123

Met Asn Arg
 1

<210> SEQ ID NO 124
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 124

Met Asn Arg
 1

<210> SEQ ID NO 125
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: AMINO TERMINUS
<220> FEATURE:
<221> NAME/KEY: MISC_FEATURE
<222> LOCATION: (3)..(3)
<223> OTHER INFORMATION: CARBOXYL TERMINUS

<400> SEQUENCE: 125

Leu Gln Lys
 1

<210> SEQ ID NO 126
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: CARBOXYL TERMINUS

<400> SEQUENCE: 126

Leu Gln Lys
 1
```

<210> SEQ ID NO 127
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 127

Phe Asp Arg
1

<210> SEQ ID NO 128
<211> LENGTH: 4
<212> TYPE: PRT
<213> ORGANISM: Artificial sequence
<220> FEATURE:
<223> OTHER INFORMATION: Major royal jelly protein fragment

<400> SEQUENCE: 128

His Asn Ile Arg
1

<210> SEQ ID NO 129
<211> LENGTH: 4
<212> TYPE: PRT
<213> ORGANISM: Artificial sequence
<220> FEATURE:
<223> OTHER INFORMATION: Major royal jelly protein fragment

<400> SEQUENCE: 129

Tyr Ile Asn Arg
1

<210> SEQ ID NO 130
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 130

Phe Thr Lys
1

<210> SEQ ID NO 131
<211> LENGTH: 7
<212> TYPE: PRT
<213> ORGANISM: Artificial sequence
<220> FEATURE:
<223> OTHER INFORMATION: Major royal jelly protein fragment

<400> SEQUENCE: 131

Ile Phe Val Thr Met Leu Arg
1               5

<210> SEQ ID NO 132
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 132

Met Gln Lys
1

<210> SEQ ID NO 133
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 133

Cys Asp Arg
1

<210> SEQ ID NO 134
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 134

Met Thr Arg
1

<210> SEQ ID NO 135
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 135

Phe Ala Lys
1

<210> SEQ ID NO 136
<211> LENGTH: 5
<212> TYPE: PRT
<213> ORGANISM: Artificial sequence
<220> FEATURE:
<223> OTHER INFORMATION: Major royal jelly protein fragment

<400> SEQUENCE: 136

Gln Asn Asp Asn Arg
1               5

<210> SEQ ID NO 137
<211> LENGTH: 5
<212> TYPE: PRT
<213> ORGANISM: Artificial sequence
<220> FEATURE:
<223> OTHER INFORMATION: Major royal jelly protein fragment

<400> SEQUENCE: 137

Gln Asn Gly Asn Lys
1               5

<210> SEQ ID NO 138
<211> LENGTH: 5
<212> TYPE: PRT
<213> ORGANISM: Artificial sequence
<220> FEATURE:
<223> OTHER INFORMATION: Major royal jelly protein fragment

<400> SEQUENCE: 138

Gln Asn Gly Asn Arg
1               5

```
<210> SEQ ID NO 139
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 139

Thr Asn Arg
1

<210> SEQ ID NO 140
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 140

Met Asp Lys
1

<210> SEQ ID NO 141
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 141

Met Asn Arg
1

<210> SEQ ID NO 142
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 142

Met Asp Arg
1

<210> SEQ ID NO 143
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 143

Thr Asp Lys
1

<210> SEQ ID NO 144
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 144

Ile Asp Arg
1
```

```
<210> SEQ ID NO 145
<211> LENGTH: 3
<212> TYPE: PRT
<213> ORGANISM: Artificial sequence
<220> FEATURE:
<223> OTHER INFORMATION: Major royal jelly protein fragment

<400> SEQUENCE: 145

Val Asn Arg
1
```

ANTI-INFLAMMATORY PROTEINS AND PEPTIDES AND METHODS OF PREPARATION AND USE THEREOF

RELATED APPLICATIONS

This application is a 35 U.S.C. §371 National Stage filing of International Application Number PCT/NZ2013/000110, filed on Jun. 24, 2013, which claims priority to, and the benefit of, New Zealand Provisional Application No. NZ 600847, filed on Jun. 22, 2012. The contents of the aforementioned applications are hereby incorporated herein by reference.

SEQUENCE LISTING

The instant application contains a Sequence Listing which has been submitted electronically in ASCII format and is hereby incorporated by reference in its entirety. Said ASCII copy, created on Jul. 15, 2015, is named WSJ-006US_Sequence_Listing.txt and is 69,737 bytes in size.

FIELD OF THE INVENTION

The present disclosure relates to anti-inflammatory proteins and peptides, their uses, and methods of their detection.

BACKGROUND OF THE INVENTION

Honey has been used for centuries by cultures through the world for its multiple health benefits. Two of the most important health benefits of honey are its anti-bacterial and anti-inflammatory properties. Manuka honey, which is produced by bees that collect nectar from *Leptospermum scoparium*, a plant native to New Zealand and southern Australia, has been identified as being a variety of honey that exhibits particularly effective anti-bacterial and anti-inflammatory properties. Jelly Bush honey, which is produced by bees that collect nectar from *Leptospermum polygalifolium*, a plant native to Australia, has also been identified as being a variety of honey that exhibits particularly effective antibacterial and anti-inflammatory properties.

Recently, it was discovered that the chemical, methylglyoxal (MGO, also called 2-oxopropanal and pyruvaldehyde), is a major component of the antibacterial activity of *Leptospermum* derived honey, such as manuka honey and jelly bush honey. Manuka honey and jelly bush honey samples contain greater concentrations of MGO, and have a higher amount of anti-bacterial activity as compared to honey samples with lower concentrations of MGO. MGO is believed to confer anti-bacterial properties on honey because MGO is a highly chemically reactive compound, and MGO can readily react with cellular molecules. The chemical reactions between MGO and cellular molecules in bacteria damage bacterial molecules that are important for viability. In this way, MGO functions as an antibacterial agent.

The presence of high levels of MGO in the honey is a feature that distinguishes manuka honey and jelly bush honey from other varieties of honey. While most varieties of honey exhibit some anti-bacterial activity, the anti-bacterial activity in most varieties of honey is primarily a result of the presence of hydrogen peroxide in the honey. *Leptospermum* derived honey, in contrast, exhibits anti-bacterial activity primarily because of the presence of MGO in the honey.

In 2004, Kohno et. al. examined the anti-inflammatory effects or actions of royal jelly at a cytokine level. The results suggest that royal jelly has anti-inflammatory actions brought about by an inhibition of pro-inflammatory cytokine production, such as TNF-α, IL-6 and IL-1, by activated macrophages. The study further suggests that the active fractions or components from the royal jelly extracts are sized between 5 kDa and 30 kDa. Thus, most honeys may have a weak anti-inflammatory effect due to royal jelly proteins that occur in the honey.

While multiple mechanisms of action of the anti-bacterial activity of manuka honey have been elucidated, the mechanisms whereby manuka honey functions as an anti-inflammatory agent have remained unknown. There is a need to develop anti-inflammatory agents based on honey, as many anti-inflammatory agents currently available have major drawbacks to their use. For example, COX-2 inhibitors, a form of non-steroidal anti-inflammatory drug (NSAID), may increase the risk of heart attack and stroke in patients, and aspirin may increase the risk of gastrointestinal bleeding. Additionally, corticosteroids are reported to inhibit the growth of epithelial cells and NSAIDs are reported as being cytotoxic so both of these classes of anti-inflammatory agents are unsuitable for use in wound care. Anti-inflammatory agents derived from honey may have fewer toxic side effects in one or more areas than drugs currently available, and may also offer different possible uses than anti-inflammatory drugs currently available.

Described in the co-pending application PCT/NZ/2011/000271 is a modified apalbumin of approximately 55-75 kDa from manuka honey that results from the high levels of methylglyoxal found in manuka honey. The inventors have identified that the modified apalbumin or major royal jelly protein has significantly greater anti-inflammatory properties than an unmodified apalbumin or major royal jelly protein.

SUMMARY OF THE INVENTION

Described herein are apalbumins, also known as major royal jelly proteins, and functional fragments thereof, which have at least one lysine or arginine amino acid chemically modified by methylglyoxal (MGO), and which exhibit enhanced anti-inflammatory effects.

In a first aspect the present invention provides a method of reducing inflammation in a cellular tissue, comprising the step of contacting the cellular tissue with a functional fragment of a major royal jelly protein (MRJP); wherein the functional fragment has been isolated, enriched, synthesized, or recombinantly produced; wherein the functional fragment comprises 2 to 20 amino acids of the last 20 amino acids at the C-terminus of the protein; and wherein a lysine amino acid residue of the functional fragment has been chemically modified by methylglyoxal (MGO). In one embodiment the major royal jelly protein (MRJP) is selected from the group consisting of MRJP1 (SEQ ID NO: 1), MRJP2 (SEQ ID NO: 2), MRJP3 (SEQ ID NO: 3), MRJP4 (SEQ ID NO: 4), MRJP5 (SEQ ID NO: 5), MRJP6 (SEQ ID NO: 6), MRJP7 (SEQ ID NO: 7), MRJP8 (SEQ ID NO: 8), and MRJP9 (SEQ ID NO: 9).

In another aspect the present invention provides a method of reducing inflammation in a cellular tissue, comprising the step of contacting the cellular tissue with a functional fragment of a major royal jelly protein (MRJP); wherein the functional fragment has been isolated, enriched, synthesized, or recombinantly produced; wherein the functional fragment comprises an amino acid sequence selected from the group consisting of: LVK (SEQ ID NO: 84), LIR (SEQ ID NO: 86), FDR (SEQ ID NO: 127), HNIR (SEQ ID NO: 128), FTK (SEQ ID NO: 130), and QNGNK (SEQ ID NO:

137); and wherein a lysine or arginine amino acid residue of the functional fragment has been chemically modified by methylglyoxal (MGO). In one embodiment the inflammation is associated with one or more of the group consisting of: an inflammatory disorder, a cardiovascular disorder, a neurological disorder, a pulmonary disorder, a proliferative disorder, an infectious disease or associated syndrome, an allergic, immunological or autoimmune disorder, and inflammation associated with a wound.

In a further aspect there is provided a method of inhibiting Cathepsin B activity in a cellular tissue, comprising the step of contacting the cellular tissue with a functional fragment of a major royal jelly protein (MRJP); wherein the functional fragment has been isolated, enriched, synthesized, or recombinantly produced; wherein the functional fragment comprises an amino acid sequence selected from the group consisting of: LVK (SEQ ID NO: 84), LIR (SEQ ID NO: 86), FDR (SEQ ID NO: 127), HNIR (SEQ ID NO: 128), FTK (SEQ ID NO: 130), and QNGNK (SEQ ID NO: 137); and wherein a lysine or arginine amino acid residue of the functional fragment has been chemically modified by methylglyoxal (MGO).

In a further aspect, there is provided an isolated functional fragment of a major royal jelly protein (MRJP), wherein the functional fragment comprises an amino acid sequence selected from the group consisting of:

| i. | KISIHL; | (SEQ ID NO: 10) |
|---|---|---|
| ii. | KNNNQNDN; | (SEQ ID NO: 11) |
| iii. | KLH; | (SEQ ID NO: 12) |
| iv. | KSNNRHNNND; | (SEQ ID NO: 13) |
| v. | KHNN; | (SEQ ID NO: 14) |
| vi. | KNQAHLD; | (SEQ ID NO: 15) |
| vii. | KNTRCISP; | (SEQ ID NO: 16) |
| viii. | KTNFFSIFL; | (SEQ ID NO: 17) | and
wherein a lysine amino acid residue of the functional fragment has been chemically modified by methylglyoxal (MGO).

In another aspect the present invention provides an isolated functional fragment of a major royal jelly protein (MRJP); wherein the functional fragment comprises an amino acid sequence selected from the group consisting of: LVK (SEQ ID NO: 84), LIR (SEQ ID NO: 86), FDR (SEQ ID NO: 127), HNIR (SEQ ID NO: 128), FTK (SEQ ID NO: 130), and QNGNK (SEQ ID NO: 137); and wherein a lysine or arginine amino acid residue of the functional fragment has been chemically modified by methylglyoxal (MGO).

In another aspect there is provided a method of producing an anti-inflammatory molecule that is an apalbumin protein or functional fragment thereof by modifying royal jelly, the method including the step of reacting royal jelly with at least 0.1% MGO at between 18 and 37 degrees Celsius.

In another aspect there is provided a method of enriching the anti-inflammatory molecules in a *Leptospermum* genus derived MGO containing honey comprising the step of adding Major Royal Jelly Protein to the honey.

In a further aspect there is provided a method of identifying (i) the anti-inflammatory capacity or (ii) MGO-modified major royal jelly protein concentration of a sample of honey, comprising the step of: assaying the Cathepsin B inhibition levels of the honey sample.

In another aspect there is provided a method of inhibiting Cathepsin B activity in a cellular tissue, comprising the step of contacting the cellular tissue with a functional fragment of a major royal jelly protein (MRJP); wherein the functional fragment has been isolated, enriched, synthesized, or recombinantly produced; wherein the functional fragment comprises 2 to 20 amino acids of the last 20 amino acids at the C-terminus of the protein; and wherein a lysine amino acid residue of the functional fragment has been chemically modified by methylglyoxal (MGO). In one embodiment the major royal jelly protein (MRJP) is selected from the group consisting of MRJP1 (SEQ ID NO: 1), MRJP2 (SEQ ID NO: 2), MRJP3 (SEQ ID NO: 3), MRJP4 (SEQ ID NO: 4), MRJP5 (SEQ ID NO: 5), MRJP6 (SEQ ID NO: 6), MRJP7 (SEQ ID NO: 7), MRJP8 (SEQ ID NO: 8), and MRJP9 (SEQ ID NO: 9).

The foregoing brief summary broadly describes the features and technical advantages of certain embodiments of the present invention. Further technical advantages will be described in the detailed description of the invention and Examples that follows. Novel features that are believed to be characteristic of the invention will be better understood from the detailed description of the invention when considered in connection with any accompanying figures and examples. However, the Figures and Examples provided herein are intended to help illustrate the invention or assist with developing an understanding of the invention, and are not intended to limit the invention's scope.

BRIEF DESCRIPTION OF THE DRAWINGS

FIG. 1A: Bolt® 4-12% Bis-Tris Plus gel. Lane 1: Protein marker (SeeBlue Plus2 Pre-stained Standard. Lane 2: Crude royal jelly is dissolved in double distilled water (10 µl load of approximately 5 mg/mL crude). Lane 3: Crude royal jelly is dissolved in double distilled water (10 µl load of approximately 2 mg/mL crude). FIG. 1B: NuPAGE® Novex® 4-12% Bis-Tris gel. Lane 3: Crude royal jelly dissolved in double distilled water (soluble fractions, pH 4). Lane 4: Fraction 2 of 5 mL HiTrap™ de-salt column in 6 M urea containing no PMSF, pH 4, 48 h at room temperature. Lane 5: Fraction 2 of 5 mL HiTrap™ de-salt column in 6 M urea containing 1 mM PMSF, pH 4, 48 h at room temperature. Lane 6: Fraction 2 of 5 mL HiTrap™ de-salt column in 6 M urea containing no PMSF, pH 8, 48 h at room temperature. Lane 7: Fraction 2 of 5 mL HiTrap™ de-salt column in 6 M urea containing 1 mM PMSF, pH 8, 48 h at room temperature. Lane 8: Fraction 2 of 5 mL HiTrap™ de-salt column in 6 M urea containing no PMSF, pH 8, 168 h at room temperature. Lane 9: Fraction 2 of 5 mL HiTrap™ de-salt column in 6 M urea containing 1 mM PMSF, pH 8, 168 h at room temperature. Lane 10: Protein marker.

FIG. 10: Amino acid sequence of MRJP1, SEQ ID NO: 1.

FIG. 11A: C-terminal sequence of MRJP1. MGO-modified lysine residue is indicated by underlining. FIG. 11B: Synthetic peptides tested for Cathepsin B inhibition. FIG. 11C: Cathepsin B inhibition by unmodified and MGO-modified peptides.

FIG. 12A: C-terminal sequence of MRJP2. MGO-modified lysine residue is indicated by underlining. FIG. 12B: Synthetic peptides tested for Cathepsin B inhibition. FIG. 12C: Cathepsin B inhibition by unmodified and MGO-modified peptides.

FIG. 13A: C-terminal sequence of MRJP3. MGO-modified lysine residue is indicated by underlining. FIG. 13B: Synthetic peptides tested for Cathepsin B inhibition. FIG. 13C: Cathepsin B inhibition by unmodified and MGO-modified peptides.

FIG. 14A: C-terminal sequence of MRJP4. MGO-modified lysine residue is indicated by underlining. FIG. 14B: Synthetic peptides tested for Cathepsin B inhibition. FIG. 14C: Cathepsin B inhibition by unmodified and MGO-modified peptides.

FIG. 15A: C-terminal sequence of MRJP5. MGO-modified lysine residue is indicated by underlining. FIG. 15B: Synthetic peptides tested for Cathepsin B inhibition. FIG. 15C: Cathepsin B inhibition by unmodified and MGO-modified peptides.

FIG. 16A: Synthetic peptide sequences. FIG. 16B: Cathepsin B inhibition by unmodified and MGO-modified peptides.

DETAILED DESCRIPTION OF THE INVENTION

Figures 1A, 1B:
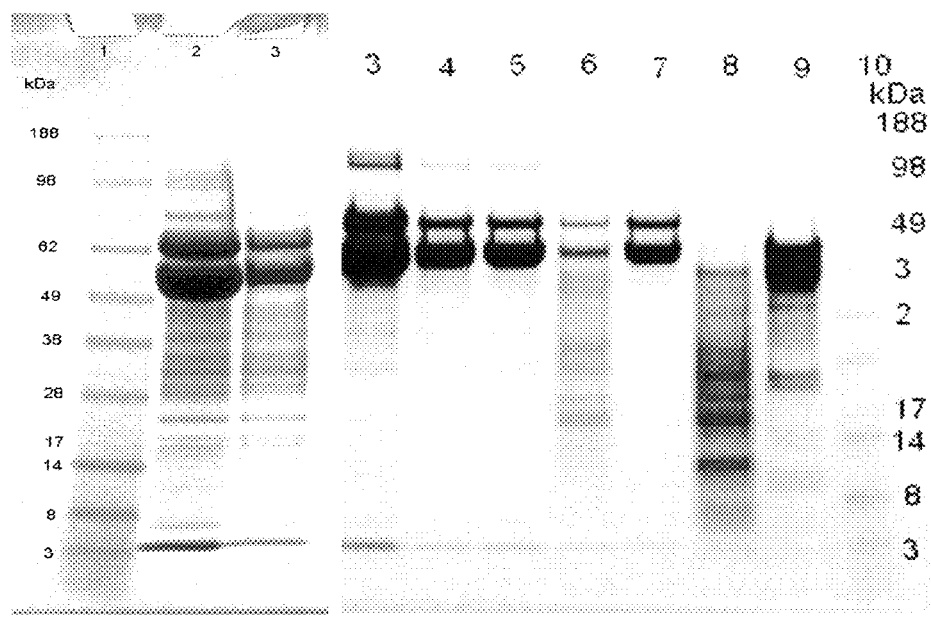
FIGS. 1A-1B: SDS PAGE analysis of MRJP.

The following description sets forth numerous exemplary configurations, parameters, and the like. It should be recog-

DEFINITIONS

In each instance herein, in descriptions, embodiments, and examples of the present invention, the terms "comprising", "including", etc., are to be read expansively, without limitation. Thus, unless the context clearly requires otherwise, throughout the description and the claims, the words "comprise", "comprising", and the like are to be construed in an inclusive sense as to opposed to an exclusive sense, that is to say in the sense of "including but not limited to".

"Royal jelly" is a honey bee secretion that is secreted from the glands in the hypopharynx of worker bees. Aside from water, protein is the major component of royal jelly and comprises the Major Royal Jelly proteins.

An "apalbumin protein" is a glycoprotein found in honey and in royal jelly. The major apalbumin found in honey is Apalbumin 1 (Apa1) also known as Major Royal Jelly Protein 1 (MRJP1) or royalactin. While the specification focuses on the major apalbumins found in honey, it is to be appreciated that the other apalbumins found in honey may also exhibit similar modification potential and similar anti-inflammatory capacity because they are all glycoproteins with a high mannose type of glycosylation as reported in 2000 by Kimura et. al. in Biosci. Biotechnol. Biochem. There are approximately nine major royal jelly proteins and the sequences of major royal jelly proteins 1-9 are shown in the Sequence Listing.

It should be understood that the terms "MRJP" (e.g., any one of MRJP1-9), "peptide" (e.g., peptide derived from any one of MRJP1-9), and "SEQ ID NO:" (e.g., any one of SEQ ID NO: 1-145, and other such terms, for simplicity, are used to identify the molecules described herein and not to provide their complete characterization. Thus, a protein or peptide may be characterized herein as having a particular amino acid sequence, a particular 2-dimensional representation of the structure, but it is understood that the actual molecule claimed has other features, including 3-dimensional structure, mobility about certain bonds and other properties of the molecule as a whole. It is the molecules themselves and their properties as a whole that are encompassed by this disclosure.

"Modification" of a primary amino acid sequence is understood to include "deletions" (that is, polypeptides in which one or more amino acid residues are absent), "additions" (that is, a polypeptide which has one or more additional amino acid residues as compared to the specified polypeptide), "substitutions" (that is, a polypeptide which results from the replacement of one or more amino acid residues), and "fragments" (that is, a primary amino acid sequence which is identical to a portion of the primary sequence of the specified polypeptide).

"Modified apalbumin" is to be understood to include any apalbumin or major royal jelly protein or fragment thereof that has been modified by the chemical reaction of methylglyoxal on the amino acids or the chemical reaction of methylglyoxal on the side chains of the amino group that make up the protein. Methylglyoxal modifications occur at free amino groups of lysine, arginine and/or cysteine amino acid moieties within the apalbumin, including the terminal amino acid, and such MGO modifications may occur on approximately 1-40 sites within the protein. For example, modified apalbumin1 means Apa1 modified at one or more sites on its amino acid sequences to provide a MGO-modified Apa1.

As described herein, MRJP "fragments" (i.e., fragments derived from one or more MRJP) will be taken to include peptides obtained from any source, e.g., isolated naturally occurring peptides, recombinant peptides, and synthetic peptides. These include peptides having the naturally occurring sequences as well as modified peptide sequences. Of particular interest are functional fragments of MRJPs, i.e., fragments that retain one or more of the activities of the starting protein, or analogues thereof. Such activities are described in detail herein. Thus, it will be understood that a "fragment" is not limited to a peptide obtained directly from a polypeptide, for example, by digestion of the original polypeptide by a peptidase.

As used herein, the term "analogue" of a protein or peptide means a protein or peptide that includes a modification as described herein, or a peptide or fragment thereof that includes one or more non-amino acid substituents replacing amino acids, while the analogue still provides the necessary activity and respective stability of the peptide or peptide fragment. The analogues of the invention may include an acetylated N-terminus (Ac) and/or an amidated C-terminus ($NH_2$), as well as a C-terminal hydroxyl residue (OH). Other analogues are also possible, including those that stabilize the domain necessary for Cathepsin B inhibition. Functional analogue are specifically encompassed by the present invention, i.e., analogues that retain one or more of the activities of the starting sequence. It will be understood that where a peptide analogue is specifically noted (e.g., Ac-Xaa-Xaa-Xaa-OH; 5), the amino acid sequence itself is also considered to be disclosed (e.g., Xaa-Xaa-Xaa). Similarly, where an unmodified peptide is specifically noted (e.g., Xaa-Xaa-Xaa), the analogue is also considered to be disclosed (e.g., Ac-Xaa-Xaa-Xaa-OH).

"C-terminus" or "C-terminal region" is to be understood to be the amino acid region that is proximate the end of an amino acid chain carrying the free alpha carboxyl group of the last amino acid.

"Lysine modified by MGO" is to be understood as a lysine amino acid covalently bound to MGO. "Arginine modified by MGO" is understood as an arginine amino acid covalently bound to MGO.

Amino acid "sequence similarity" or "sequence identity" refers to the amino acid to amino acid comparison of two or more polypeptides at the appropriate place, where amino acids are identical or possess similar chemical and/or physical properties such as charge or hydrophobicity. Sequence similarity and identity are typically determined by sequence alignments at the regions of highest homology. Sequence alignment algorithms are well known and widely used in the art. Based on the sequence comparison, a "percent identity" can be determined between the compared polypeptide sequences.

Tissue that is "inflamed" is defined as tissue in which an immune response has occurred in response to injury or infection in the tissue, and in which the tissue has one or more symptoms of pain, swelling, heat, sensitivity, and redness.

As used herein, "anti-inflammatory capacity" is defined as the capacity to clinically reduce inflammation or the symptoms of inflammation in cellular tissue. Anti-inflammatory capacity may be determined using the phagocytosis inhibition assay (PIA) described in PCT/NZ PCT/NZ/2011/000271 or the DCFDA assay also described in PCT/NZ/

2011/000271 or the anti-inflammatory capacity may also be determined by the inhibition of Cathepsin B as described in detail below.

BRIEF DESCRIPTION OF THE SEQUENCES

SEQ ID NO: 1—amino acid sequence of Apa1 (also known as Major Royal Jelly Protein 1) obtained from http://www.uniprot.org/uniprot/O18330. See FIG. 10.

SEQ ID NO: 2—amino acid sequence of Major Royal Jelly Protein 2 obtained from http://http://www.uniprot.org/uniprot/O77061 is shown in the Sequence Listing.

SEQ ID NO: 3—amino acid sequence of Major Royal Jelly Protein 3 obtained from http://www.uniprot.org/uniprot/Q17060-1 is shown in the Sequence Listing.

SEQ ID NO: 4—amino acid sequence of Major Royal Jelly Protein 4 obtained from http://www.uniprot.org/uniprot/Q17060-1 is shown in the Sequence Listing.

SEQ ID NO: 5—amino acid sequence of Major Royal Jelly Protein 5 obtained from http://www.uniprot.org/uniprot/O97432 is shown in the Sequence Listing.

SEQ ID NO: 6—amino acid sequence of Major Royal Jelly Protein 6 obtained from http://www.uniprot.org/uniprot/Q6W3E3 is shown in the Sequence Listing.

SEQ ID NO: 7—amino acid sequence of Major Royal Jelly Protein 7 obtained from http://www.uniprot.org/uniprot/Q6IMJ9 is shown in the Sequence Listing.

SEQ ID NO: 8—amino acid sequence of Major Royal Jelly Protein 8 obtained from http://www.uniprot.org/uniprot/Q6TGR0 is shown in the Sequence Listing.

SEQ ID NO: 9—amino acid sequence of Major Royal Jelly Protein 9 obtained from http://www.uniprot.org/uniprot/Q4ZJX1 is shown in the Sequence Listing.

Exemplary fragments of MRJPs include a fragment of SEQ ID NO: 1 that comprises -Lys-Ile-Ser-Ile-His-Leu (SEQ ID NO: 10) or an analogue thereof; a fragment of SEQ ID NO: 2 that comprises -Lys-Asn-Asn-Asn-Gln-Asn-Asp-Asn (SEQ ID NO: 11) or an analogue thereof; a fragment of SEQ ID NO: 3 that includes -Lys-Leu-His (SEQ ID NO: 12) or an analogue thereof; a fragment of SEQ ID NO: 4: that includes -Lys-Ser-Asn-Asn-Arg-His-Asn-Asn-Asn-Asp (SEQ ID NO: 13) or an analogue thereof; a fragment of SEQ ID NO: 5 that includes -Lys-His-Asn-Asn (SEQ ID NO: 14) or an analogue thereof; a fragment of SEQ ID NO: 6 that includes -Lys-Asn-Gln-Ala-His-Leu-Asp-(SEQ ID NO: 15) or an analogue thereof; a fragment of SEQ ID NO: 8 that includes -Lys-Asn-Thr-Arg-Cys-Ile-Ser-Pro (SEQ ID NO: 16) or an analogue thereof; a fragment of SEQ ID NO: 9 that includes -Lys-Thr-Asn-Phe-Phe-Ser-Ile-Phe-Leu (SEQ ID NO: 17) or an analogue thereof. In certain aspects, the lysine residue of these fragments is modified by MGO.

Other fragments are described in detail herein, including those shown as SEQ ID NO: 18-145. The Sequence Listing and all the sequences included therein are hereby incorporated herein in their entirety.

MGO-Modified Major Royal Jelly Proteins

Methylglyoxal or MGO is a highly chemically reactive compound with the formula $C_3H_4O_2$. MGO is formed by multiple metabolic pathways in living organisms. Certain preparations of manuka honey, which are referred to as "active" manuka honey, contain much higher concentrations of MGO than other varieties of honey. Active manuka honey has been determined to contain MGO concentrations up to 1000-fold greater than the MGO concentration in other varieties of honey (E. Mavric et al, 2008).

MGO can participate in a variety of chemical reactions in living organisms, including the formation process of advanced glycation endproducts (AGEs). MGO can modify proteins by reacting with the free amino groups of the amino acids arginine, lysine, and/or cysteine and the terminal amino group, and thereby can chemically modify proteins that contain arginine and/or lysine.

MGO-modified major royal jelly proteins (MRJPs) and fragments thereof can be derived by isolation of the molecules from active manuka honey. The modified proteins and fragments can be isolated from honey and/or enriched from honey by biochemical techniques. These techniques include but are not limited to filtration, centrifugation, and chromatography, such as ion-exchange, affinity, hydrophobic interaction, size exclusion, and reverse-phase chromatography. MGO-modified MRJP and fragments can also be purified from various sources or chemically synthesized by addition of MGO to royal jelly. In another approach, the major royal jelly may be added to honey derived from the *Leptospermum* genus, such as manuka honey and jelly bush honey to achieve enrichment of MGO-modified MRJP and fragments in the honey.

A MGO-modified MRJP or a fragment thereof may also be derived by obtaining a sequence coding for the amino acid sequences of SEQ IDs NO: 1-145, cloning the coding sequence into an appropriate vector, transforming a cell line with the vector, causing the polypeptide or peptide to be expressed, purifying the polypeptide or peptide, mixing the polypeptide or peptide with MGO to allow for chemical reaction between MGO and the polypeptide or peptide, and purifying the MGO-modified polypeptide or peptide.

Expression systems may contain control sequences, such as promoters, enhancers, and termination controls such as are known in the art for a variety of hosts (See e.g. Sambrook et al., *Molecular Cloning: A Laboratory Manual*, Second Ed., Cold Spring Harbor Press (1989) which is incorporated herein in its entirety). The expression systems may also contain signal peptide and prep-pro-protein sequences that facilitate expression of the coding sequence and/or folding of the protein.

Synthetic production or peptides may be carried out using the solid-phase synthetic method described by Goodman M. (ed.), "Synthesis of Peptides and Peptidomimetics" in Methods of organic chemistry (Houben-Weyl) (Workbench Edition, 2004; Georg Thieme Verlag, Stuttgart, N.Y.). This technique is well understood and is a common method for preparation of peptides. Peptides may also be synthesized using standard solution peptide synthesis methodologies, involving either stepwise or block coupling of amino acids or peptide fragments using chemical or enzymatic methods of amide bond formation. These solution synthesis methods are well known in the art. See, e.g. H. D. Jakubke in The Peptides, Analysis, Synthesis, Biology, Academic Press, New York, 1987, p. 103-165; J. D. Glass, ibid., pp. 167-184; and EP 0324659 A2, describing enzymatic peptide synthesis methods. Commercial peptide synthesizers, such as the Applied Biosystems Model 430A, may also be used.

MGO-modified forms of amino acid variants of MRJPs and their fragments may also exhibit anti-inflammatory capacity. As would be understood by one of ordinary skill in the art, minor modification of the primary amino acid sequence of SEQ ID NO: 1 may result in a polypeptide which has substantially equivalent or enhanced anti-inflammatory activity as compared to SEQ ID NO: 1. A peptide may be also modified to provide substantially equivalent or enhanced anti-inflammatory activity as the original peptide. When modification includes one or more substitutions, preferred substitutions are those that are of a conservative nature, i.e., wherein the residue is replaced by another of the same general type.

In making modifications to the protein or peptide, the hydropathic index of amino acids may be considered (See, e.g., Kyte. et al., J. Mol. Biol. 157, 105-132 (1982), herein incorporated by reference in its entirety). It is known in the art that certain amino acids may be substituted by other amino acids having a similar hydropathic index or score and still result in a molecule having similar biological activity.

In particular aspects, the MGO-modified MRJP variant or fragment variant exhibits at least about 75% sequence identity to the non-variant sequence, preferably at least about 80% identity, more preferably at least about 85%, 90%, 91%, 92%, 93%, 94%, 95%, 96%, 97%, 98%, 99% or 100% sequence identity to any wild type or reference sequence described herein. It is of particular interest where the MGO-modified MRJP variant or fragment variant exhibits anti-inflammatory capacity substantially comparable to or increased over that of non-variant molecule.

In certain aspects, the MRJP fragment is derived from the C-terminal sequence of the protein. The fragment may be derived from the last 20 amino acids, last 18 amino acids, last 16 amino acids, last 14 amino acids, last 12 amino acids, last 10 amino acids, last 8 amino acids, last 6 amino acids, last 4 amino acids, or last 2 amino acids of the C-terminal sequence of the protein. The functional fragment may comprise 2 to 20 amino acids, 2 to 18 amino acids, 2 to 16 amino acids, 2 to 14 amino acids, 2 to 12 amino acids, 2 to 10 amino acids, 2 to 8 amino acids, 2 to 6 amino acids, 2 to 4 amino acids, or 2 amino acids of this C-terminal region. Thus, the MRJP fragment may be 20 amino acids, 18 amino acids, 16 amino acids, 14 amino acids, 12 amino acids, 10 amino acids, 8 amino acids, 6 amino acids, 4 amino acids, or 2 amino acids in length. Longer fragments may also be useful. In particular aspects, the MGO-modified lysine is at least three residues from the C-terminus, or no more than six residues from the C-terminus of the protein.

Of particular interest are functional fragments of the C-terminus of MRJPs as described in detail herein. However, other fragment of MRJPs may also be obtained, for example, fragments corresponding to internal amino acid sequences of the protein. In some aspects, a fragment may include a MRJP-derived amino acid sequence which is fused to (i.e., contiguous with) one or more heterologous amino acid sequences. Thus, an MRJP fragment may be presented as a portion of a major royal jelly protein that is included as part of a larger peptide or polypeptide. This may provide better stability and or expression capabilities, or provide options for cleavage or tagging. In certain aspects, the MRJP fragment may be chemically linked to other molecules, for example, one or more chemical moieties. While MGO-modified fragments are specifically embraced, other chemical modifications of are also possible. The MRJP fragment may also be linked to a substrate such as beads, catheters, needles, sutures, stents, implantable medical devices, contact lenses, root canal fillers, wound dressings, burn dressings, tissue culture plates, fibers, and paper. The fragment may be prepared as a peptide conjugate in accordance with known methods.

The formation of MGO-modified MRJP or its fragments in honey can be stimulated by (i) prolonged storage at ambient temperature, or (ii) incubation of honey at elevated temperatures (30-40 degrees Celsius), thereby increasing the antiinflammatory capacity of a sample of honey. Addition of MGO or an MGO precursor, such as dihydroxyacetone (DHA) to a sample of honey, along with sufficient time and/or heating to convert the MGO precursor to MGO, may also stimulate the formation of MGO-modified MRJP or fragments thereof in that sample of honey, and may also increase the anti-inflammatory capacity of the sample of honey, by the generation of MGO-modified MRJP in the honey sample.

MRJP1 and MRJP3 with enhanced anti-inflammatory properties can also be formed outside of honey. Completely or partially purified MRJP has been found to be treatable with MGO, in order to yield MGO-modified MRJP. The MGO-modified MRJP1 and MRJP3 exhibits enhanced anti-inflammatory properties when compared to the unmodified MRJP1 and MRJP3.

MGO-modified MRJP, fragments thereof, and variants thereof may be included in therapeutically-effective amounts in pharmaceutical compositions. It is also to be appreciated that a peptide having MGO-modified lysine and/or arginine may be prepared synthetically for use in the compositions.

The pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intravitreal, intramuscular, intravenous or epidural injection as, for example, a sterile solution or suspension, or sustained release formulation.

Also encompassed is topical application, for example, as an eye drop, or as a cream, ointment, or a controlled release patch or spray applied to the skin; as well as administration intravaginally or intrarectally, for example, as a pessary, cream or foam; administration sublingually; administration ocularly; administration transdermally; administration pulmonarily, or nasally.

When the compounds of the present invention are administered as pharmaceuticals, to humans and animals, they can be given per se or as a pharmaceutical composition containing, for example, about 0.1 to 99%, or about 1 to 50%, or about 10 to 40%, or about 10 to 30, or about 10 to 20%, or about 10 to 15% of active ingredient in combination with a pharmaceutically acceptable carrier or excipient.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the pharmaceutical compositions described herein. These compositions may also contain adjuvants such as preservatives, wetting agents, emulsifying agents, and dispersing agents.

Prevention of the action of microorganisms upon the compounds of the present invention may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Methods of Use for MGO-Modified MRJPs or Fragments Thereof

Cysteine proteases such as Cathepsin B are involved in the normal lysosomal degradation and processing of proteins. The increased expression or enhanced activation of cysteine proteases is associated with a number of medical conditions. The MGO-modified MRJPs or fragments, or a MGO-modified MRJP- or fragment-containing composition may thereby be used in the prevention, delay, mitigation, or treatment of the following disorders.

Included are inflammatory disorders such as rheumatoid arthritis, polyarthritis, and other inflammatory arthritidies, inflammatory bowel disease, and inflammatory bowel syndrome, inflammatory peritonitis, uveitis, sepsis, systemic inflammatory response syndrome, multiple organ failure; cardiovascular disorders such as ischemia reperfusion injury from transplantation and/or vascular surgery, angiogenesis, neovascularization, acute cardiac allograft dysfunction, ischemic cardiac damage, chemotherapy-induced myocardial suppression; musculoskeletal disorders such as osteoarthritis, osteoporosis, muscular dystrophy, myositis; neurological disorders such as multiple sclerosis, stroke, Alzheimer's disease, progressive multifocal leukoencephalopathy (PML), prion-associated disorders, ataxia telangiectasia, central nervous system injury; pulmonary disorders such as asthma, bronchitis, chronic obstructive pulmonary disease (COPD), adult respiratory distress syndrome, Wegeneres granulomatosis, and emphysema.

Included as well are proliferative disorders, including those involving solid tumors, lymphomas, leukemias and other malignancies, for example, acute and chronic myelogenous leukemia, neuronal cancer, cancer invasion and metastasis, tumor angiogenesis, B and T cell lymphomas, acute and chronic lymphocytic leukemia, resistance to chemotherapy, cancer associated coagulopathies (including deep venous thrombosis, coronary artery disorder, pulmonary embolism, disseminated intravascular coagulation), Hodgkin's disease, carcinomas of the colon, liver, lung, breast, kidney, stomach, pancreas, esophagus, oral pharynx, intestine, thyroid, prostate, bladder, brain; osteosarcoma, chondrosarcoma and liposarcoma; neuroblastoma; melanoma; and carcinomas derived from amnion and/or chorion).

Additionally included are infectious diseases and associated syndromes such as septic shock (including Gram-negative sepsis), HIV infection and AIDS, genital herpes, zoster, chickenpox, molluscum contagiosum, EBV infections, encephalitis including EBV associated encephalitis, choreoretinitis, cytomegalovirus (CMV) associated choreoretinitis or encephalitis, cytomegalovirus infections in neonates (including related pneumonitis), opportunistic infections in immunocompromised individuals (including AIDS and transplant patients), dysentery, hepatitis C, hepatitis A, keratoconjuctovitis, bronchopneumonia (including pneumonia in immunocompromised individuals), gastroenteritis, malaria, rhinovirus, polio, enterovirus infections, common cold, aseptic meningitis, foot and mouth disease, *Klebsiella pneumoniae* infection, *Escherichia coli* or *Staphylococcus epidermidis*, leprosy bacteremia, otitis media, lambliasis, non-atopic sinusitis, and fuliminant hepatitis.

Further included are allergic, immunological, and autoimmune disorders such as house dust mite allergy, transplant rejection, graft verses host disease, Type 1 diabetes mellitus, autoimmune thyroiditis, psoriasis, dermatitis (e.g., contact dermatitis), antibody-mediated autoimmune diseases, lupus erythematosus, Sjogren's syndrome, autoimmune encephalomyelitis; kidney disorders such as polycystic kidney disease, glomerulonephritis; as well as other disorders such as periodontal disease, alcohol hepatitis, prostate hypertrophy, trauma, cutaneous mastocytosis, radiation- and HIV-induced diarrhea, cachexia (including accompanying cancer and malnutrition), and inflammation associated with wounds, e.g., puncture wounds, diabetic ulcers, fungating wounds, cuts, bites, and surgical wounds.

Indications of note include: rheumatoid arthritis, polyarthritis, Alzheimer's disease, multiple sclerosis, especially relapsing-remitting multiple sclerosis, progressive multifocal leukoencephalopathy (PML), asthma, bronchitis, adult respiratory distress syndrome, Wegeneres granulomatosis, emphysema, and COPD, melanoma, genital herpes, EBV infection, encephalitis, including EBV associated encephalitis, choreoretinitis, including CMV choreoretinitis, bronchopneumonia, gastroenteritis, uveitis, psoriasis, dermatitis, and various wounds.

In a specific aspect, the MGO-modified MRJPs or fragments thereof may be formulated as a wound dressing. This includes any covering that can be applied to a lesion. This encompasses infected and non-infected abrasions, cuts, bites, burns, wounds, ulcers, abscesses, surgical wounds, fungating tumors, and pressure sores. The lesion is preferably external, for example resulting from damage or injury to the skin.

The MGO-modified MRJP or fragment, or the MGO-modified MRJP- or fragment-containing composition may be positoned on a surface of a substrate, such as a wound dressing substrate. The composition may include water and optionally another solvent. For such compositions, the water and optional solvent may be allowed to evaporate. The MGO-modified MRJP or fragment, or the MGO-modified MRJP- or fragment-containing composition may be incorporated into a natural or synthetic fiber. For example, the polypeptide or peptide may be incorporated on or into fibers used for cloth, synthetic or paper dressings. Paper may be used as part of a temporary wound dressing.

The treated substrate may include natural or synthetic materials, and implantable devices. The biocompatibility of the substrate may be evaluated by any suitable methodology known in the art, including one or more viability/cytotoxicity assays known to those of ordinary skill in the art. The treated substrate may be in contact with an aqueous environment, such as water or the inside of a patient. Alternatively, the treated substrate may be contact with air or air and/or air borne bacteria in an external environment or an enclosed bodily organ, such as a lung.

Thus, inflammation in tissue may be reduced by administering one or more purified MGO-modified MRJPs or fragments, or a MGO-modified MRJP- or fragment-containing composition to inflamed tissue. Inflammation from various injuries, infections, and medical diseases may be treated. Included are acute and chronic inflammatory diseases as noted above.

Regarding rheumatoid arthritis, it is noted that peptidyl fluoromethyl ketones with the amino acid sequence Phe-Ala held constant but with variable N-terminal groups were effective in inhibiting Cathepsin B activity in vitro and also inhibiting the severity of inflammation and the extent of cartilage and bone damage in adjuvant-induced arthritis. See Ahmed et al., 1992. It is considered that the MGO-modified MRJP peptides or fragments or a MGO-modified MRJP-containing composition of the invention can be used in similar treatments for rheumatoid arthritis.

MGO-modified MRJPs or fragments, or a MGO-modified MRJP- or fragment-containing composition may reduce inflammation in tissue by reducing the rate of phagocytosis by immune cells, and by blocking the mannose receptor or other receptors on immune cells, which trigger phagocytosis. Immune cells include macrophages, monocytes, dendritic cells, and granulocytes.

Phagocytosis is a cellular response or process of engulfing solid particles and cellular uptake in the immune system. It is a major mechanism used to remove pathogens and cell debris. Bacteria, dead tissue cells, and small mineral particles are all examples of objects that may be phagocytosed or engulfed by a cell. Phagocytosis occurs at the beginning of the inflammatory response of leukocytes to a trigger of inflammation. Reactive oxygen species and cytokines are produced by cells after phagocytosis to recruit and activate more phagocytes as part of a cascade of cellular events which start with phagocytosis. Thus, inhibition of phagocytosis stops the inflammatory response at the start of the cascade.

MGO-modified MRJPs or fragments, or an MGO-modified MRJP- or fragment-containing composition may be administered to inflamed tissue in various different forms. The MGO-modified molecule may be purified from other components. For administration, it may be desirable to include one or more other types of compounds such as pharmaceutically acceptable carriers, adjuvants, or other therapeutic molecules. Other anti-inflammatory agents may be used for co-administration with the MGO-modified MRJPs or fragments, or an MGO-modified MRJP- or fragment-containing composition.

MGO-modified MRJPs or functional fragments thereof may be isolated from active manuka honey, or from manuka honey, or any other type of honey to which MGO or an MGO precursor has been added to modify the apalbumin, or it may be purified from royal jelly or a system in which apalbumin is recombinantly expressed and then treated with MGO.

MGO-modified MRJPs or fragments may be included in a composition containing one or more other types of compounds. This includes MGO-modified MRJPs or fragments contained in honey or a honey extract that has been enriched for MGO-modified components, and MGO-modified MRJPs or fragments in extracts from the recombinant production of an apalbumin or its peptides, and the chemical modification of the apalbumin or its peptides with MGO.

MGO-modified MRJPs or fragments or an MGO-modified MRJP- or fragment-containing composition may be administered to inflamed tissue in various different forms, including but not limited to: creams, lotions, liquid solutions, or poultices. MGO-modified MRJPs or fragments may also be administered to inflamed tissue as by inclusion of MGO-modified MRJP peptides or fragments in an edible product. Such products include but are not limited to beverages, candies, syrups, lozenges, pills, and foods.

Methods of Detecting MGO-Modified MRJPs or MRJP Fragments, and Characterizing Properties of Honey The anti-inflammatory capacity of a sample of honey may be determined through detection of MGO-modified MRJPs or fragments thereof. The chemical modification of MRJPs by MGO generates molecules that exhibit Cathepsin B inhibition activity. Because MRJPs are present in honey, by measuring the Cathepsin B inhibition activity of a sample of honey, a measurement of the relative concentration of MGO-modified MRJPs or fragments in the honey sample can be obtained. A measurement of the concentration of MGO-modified MRJPs or fragments in a sample of honey directly relates to the anti-inflammatory capacity of the sample of honey.

Because high MGO concentration is a feature unique to manuka honey among all honey varieties, honey producers may try to simulate active manuka honey by adding MGO to samples of honey that do not naturally contain a desired concentration of MGO. Consumers prefer naturally occurring honeys over treated honeys. Purified, active MGO is readily available from commercial chemical producers (e.g. Sigma-Aldrich, St. Louis, Mo., sells a solution of ~40% methylglyoxal in water), and honey producers may add MGO to a sample of honey that does not naturally contain a desired concentration of MGO, in order to raise the concentration of MGO in the honey sample to a desired level.

In particular aspects, the MGO-modified MRJPs or functional fragments thereof are obtained by one or more processes independent from natural honey formation. A process independent from natural honey formation includes any activity not performed by bees, and it therefore includes activities such as addition of purified MGO to a honey sample. A process independent from natural honey formation does not include activities such as bees collecting nectars, pollens, or other plant products that contain high levels of MGO or MGO-precursor molecules.

The Cathepsin B inhibition activity of honey may also be used to determine an appropriate time to harvest honey from a hive or to store harvested honey in order to obtain honey with desired anti-inflammatory properties. Because the modification of MRJPs by MGO in honey may occur over a period of time, a honey producer may choose to keep honey in the hive until it contains a desired anti-inflammatory capacity and concentration of MGO-modified MRJPs. By measuring the Cathepsin B inhibition activity of samples of honey from the hive at different time intervals, a honey producer can use the measurement of the Cathepsin B inhibition activity of the honey as a method for determining the optimal time to harvest honey from the hive in order to obtain a honey having desired anti-inflammatory properties in the honey.

Similarly, a honey producer may also measure the Cathepsin B inhibition activity of honey stored outside of the hive, in order to determine if the honey sample has a desired level of anti-inflammatory properties. By measuring the Cathepsin B inhibition activity of honey samples, a honey producer seeking to obtain a honey sample containing a desired anti-inflammatory capacity can store honey until it has developed a desired level of anti-inflammatory capacity by the formation of MGO-modified MRJPs.

EXAMPLES

The examples described herein are provided for the purpose of illustrating specific embodiments of the invention and are not intended to limit the invention in any way. Persons of ordinary skill can utilize the disclosures and teachings herein to produce other embodiments and variations without undue experimentation. All such embodiments and variations are considered to be part of this invention.

Example 1

Preparation and Analysis of MGO-Modified MRJP Proteins 1 and 3

Royal jelly obtained from Watson & Son/ManukaMed, was dissolved at 50 mg/mL in phosphate buffered saline pH 7.4 or in 100 mM disodium hydrogen phosphate pH 9.4. The pH value of the final solutions was 3.5-4.0 when PBS was used, or pH 7.4 when 100 mM disodium hydrogen phosphate pH 9.4 was used.

The protein solution was mixed for 10 minutes before centrifugation of the solution at 10,000 rpm in an SS34 rotor at 4° C. The supernatant was passed through a 0.45 micron filter and then further fractionated using ion exchange chromatography and heparin Sepharose™ to purify MRJP1. Alternatively, the crude mixture was fractionated using a 5 mL HiTrap™ desalting column (GE), or separated using size exclusion chromatography on a Sephadex™ G75 column (GE).

The crude mixture was also reacted with MGO at final concentrations of 0.05%, 0.1%, 0.15%, 0.5%, and 1% at pH 7.4 and 3.5-4.0 as well as pH 6.9, and pH 5.0. Reactions were performed at room temperature, 22° C., 37° C., 40° C. and 60° C. The reactions with respect of MGO coupling were performed over the following time periods: 1 day, 2 day, 3 day, 4 day, 5 day, 6 days, 7 days, 8 days, 9 days and 14 days.

Analysis of the MGO-modified proteins was performed using native PAGE analysis, SDS PAGE analysis, absorbance at 280 nm (protein concentration), absorbance at 330 nm (Arg-MGO adduct formation), size exclusion chromatography (SEC) on Sephadex™ G75, HiTrap™ desalting column and reactions with trinitrobenzene sulphonic acid (TNBS) reaction with lysine residues, fluorescence analysis excitation at 330 nm and emission at 410 nm (Arg-MGO adduct formation) due to the formation of argpyrimidine (Kim et al., 2010).

SDS PAGE analysis was performed on a Bolt® 4-12% Bis-Tris Plus gel. A 10 well system (BG04412BOX, Life technologies, NZ) was used in the gel electrophoresis analysis of samples following the manufacturer's protocol. 2-mercaptoethanol (M3148, Sigma Aldrich, NZ) was used as a reducing agent instead of DTT. The protein marker was SeeBlue Plus2 Pre-stained Standard (LC5925, Life Technologies, NZ). Further SDS PAGE analysis was performed using NuPAGE® Novex® 4-12% Bis-Tris gels, 1.0 mm, 10 well (NP0321BOX, Life technologies, NZ). Gel electrophoresis analysis was carried out for samples dissolved in 6M urea followed by manufacturer's protocol. As before, 2-mercaptoethanol (M3148, Sigma Aldrich, NZ) was used as a reducing agent instead of DTT, and the protein marker was SeeBlue Plus2 Pre-stained Standard (LC5925, Life Technologies, NZ). This analysis revealed the presence of two major royal jelly proteins MRJP1 and MRJP3 (FIGS. 1A and 1B).

MGO modification reactions were carried out at different pH conditions for a total of 9 days, as detailed above. Samples were collected every 24 hours and analyzed on 4-16% Native PAGE™ Novex® Bis-Tris gels 1.0 mm, 15 well (BN1004BOX, Life Technologies, NZ) following instructions provided in the manual. Typically, 4 µL of NuPAGE™ LDS sample buffer (4×) (Invitrogen, Carlsbad USA Cat. No. NP0007) was mixed with 11 µl of protein sample plus 1 µl of Native PAGE™ 5% G-250 sample additive. Then, 12 µl of this sample mix was loaded into native PAGE gels. Gels were run at 150 V for 120 minutes following manufacturer's protocols. Protein bands were visualized after de-staining for 2-4 hours following manufacturer's instructions. Gels were scanned using the UVITEC Cambridge, UK Gel-doc system.

Figure 2:
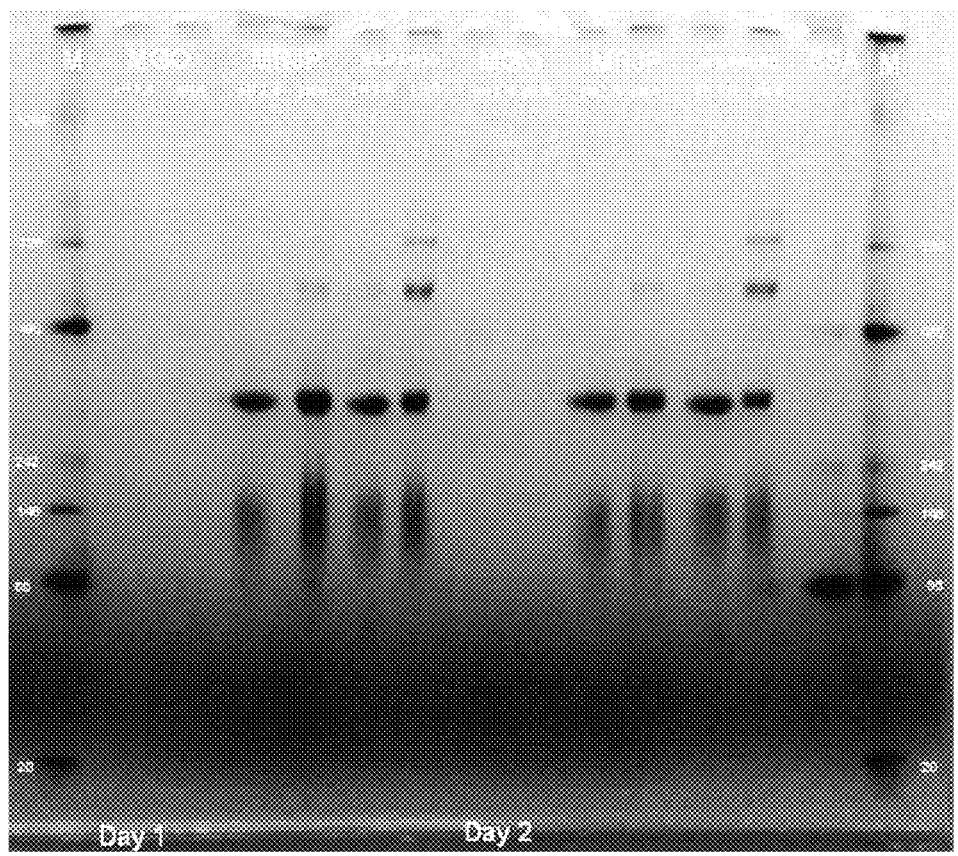
FIG. 2: Native PAGE™ Novex® 4-16% Bris-Tri gel of MGO-modified MRJP at pH 4.0 and 7.0, day 1 and day 2. Lane 1: Protein Standard contains protein bands 20-12,000 kDa]. Lane 2: MGO alone in PBS buffer, pH 7.4 after 24 h. Lane 3: MGO alone in 0.2 M sodium acetate buffer, pH 4.0 after 24 h. Lane 4: MRJP in PBS buffer, pH 7.4 after 24 h. Lane 5: MRJP in 0.2 M sodium acetate buffer, pH 4.0 after 24 h. Lane 6: MRJP reacted with MGO in PBS buffer, pH 7.4 after 24 h. Lane 7: MRJP reacted with MGO in 0.2 M sodium acetate buffer, pH 4.0 after 24 h. Lane 8: MGO alone in PBS buffer, pH 7.4 after 48 h. Lane 9: MGO alone in 0.2 M sodium acetate buffer, pH 4.0 after 48 h. Lane 10: MRJP in PBS buffer, pH 7.4 after 48 h. Lane 11: MRJP in 0.2 M sodium acetate buffer, pH 4.0 after 48 h. Lane 12: MRJP reacted with MGO in PBS buffer, pH 7.4 after 48 h. Lane 13: MRJP reacted with MGO in 0.2 M sodium acetate buffer, pH 4.0 after 48 h. Lane 14: BSA control. Lane 15: Protein marker (same as Lane 1).
Figure 3:
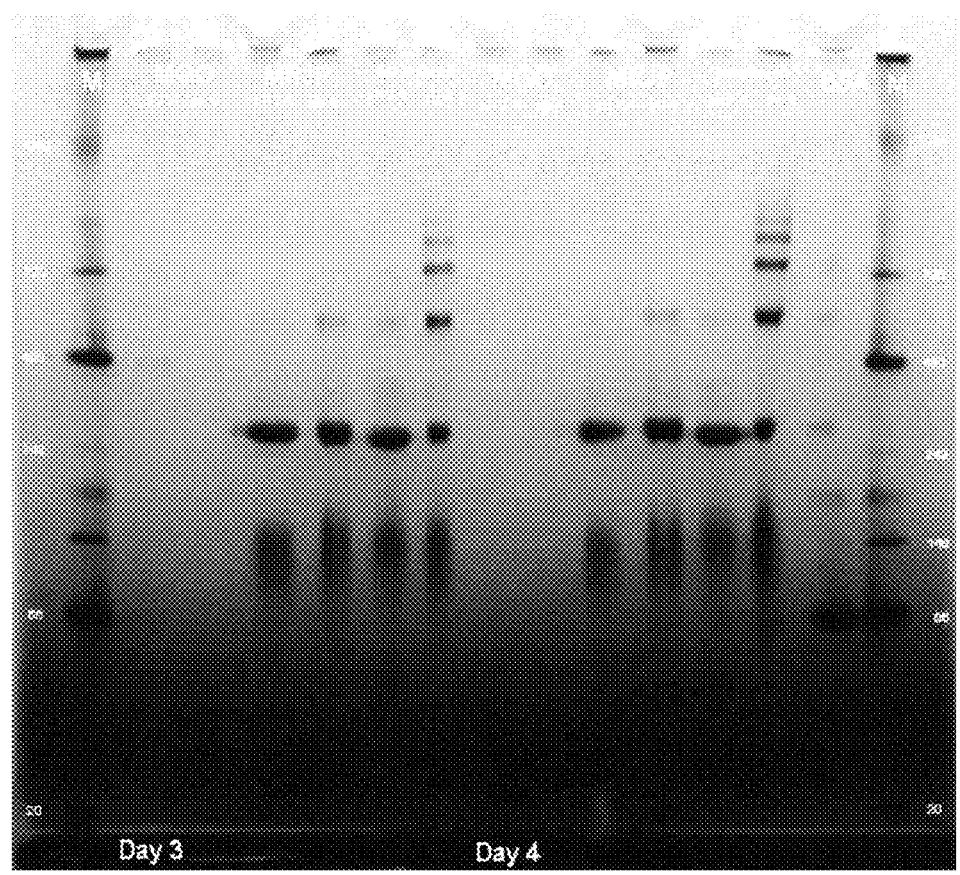
FIG. 3: Native PAGE™ Novex® 4-16% Bris-Tri gel of MGO-modified MRJP at pH 4.0 and 7.0, day 3 and day 4. Lane 1: Protein Standard contains protein bands 20-12,000 kDa. Lane 2: MGO alone in PBS buffer, pH 7.4 after 72 h. Lane 3: MGO alone in 0.2 M sodium acetate buffer, pH 4.0 after 72 h. Lane 4: MRJP in PBS buffer, pH 7.4 after 72 h. Lane 5: MRJP in 0.2 M sodium acetate buffer, pH 4.0 after 72 h. Lane 6: MRJP reacted with MGO in PBS buffer, pH 7.4 after 72 h. Lane 7: MRJP reacted with MGO in 0.2 M sodium acetate buffer, pH 4.0 after 72 h. Lane 8: MGO alone in PBS buffer, pH 7.4 after 96 h. Lane 9: MGO alone in 0.2 M sodium acetate buffer, pH 4.0 after 96 h. Lane 10: MRJP in PBS buffer, pH 7.4 after 96 h. Lane 11: MRJP in 0.2 M sodium acetate buffer, pH 4.0 after 96 h. Lane 12: MRJP reacted with MGO in PBS buffer, pH 7.4 after 96 h. Lane 13: MRJP reacted with MGO in 0.2 M sodium acetate buffer, pH 4.0 after 96 h. Lane 14: BSA control. Lane 15: Protein marker (same as Lane 1).
Figure 4:
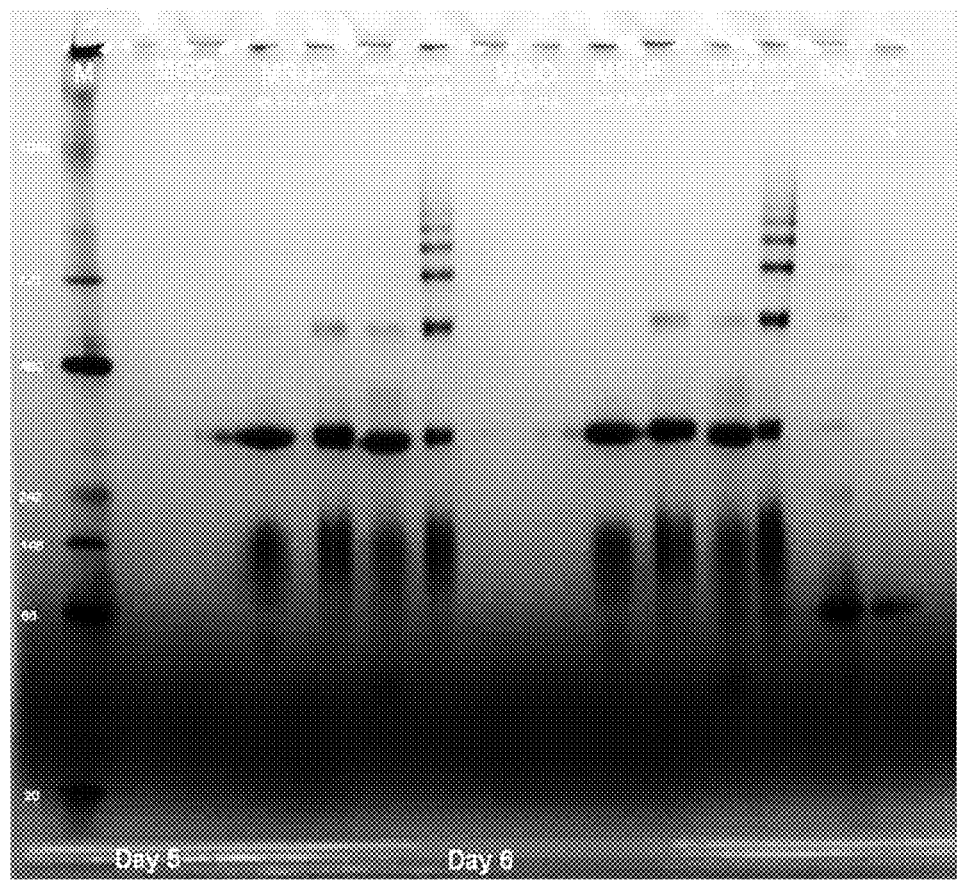
FIG. 4: Native PAGE™ Novex® 4-16% Bris-Tri gel of MGO-modified MRJP at pH 4.0 and 7.0, day 5 and day 6. Lane 1: Protein Standard contains protein bands 20-12,000 kDa. Lane 2: MGO alone in PBS buffer, pH 7.4 after 120 h. Lane 3: MGO alone in 0.2 M sodium acetate buffer, pH 4.0 after 120 h. Lane 4: MRJP in PBS buffer, pH 7.4 after 120 h. Lane 5: MRJP in 0.2 M sodium acetate buffer, pH 4.0 after 120 h. Lane 6: MRJP reacted with MGO in PBS buffer, pH 7.4 after 120 h. Lane 7: MRJP reacted with MGO in 0.2 M sodium acetate buffer, pH 4.0 after 120 h. Lane 8: MGO alone in PBS buffer, pH 7.4 after 144 h. Lane 9: MGO alone in 0.2 M sodium acetate buffer, pH 4.0 after 144 h. Lane 10: MRJP in PBS buffer, pH 7.4 after 144 h. Lane 11: MRJP in 0.2 M sodium acetate buffer, pH 4.0 after 144 h. Lane 12: MRJP reacted with MGO in PBS buffer, pH 7.4 after 144 h. Lane 13: MRJP reacted with MGO in 0.2 M sodium acetate buffer, pH 4.0 after 144 h. Lane 14: BSA control. Lane 15: Manuka honey (crude)
Figure 5:
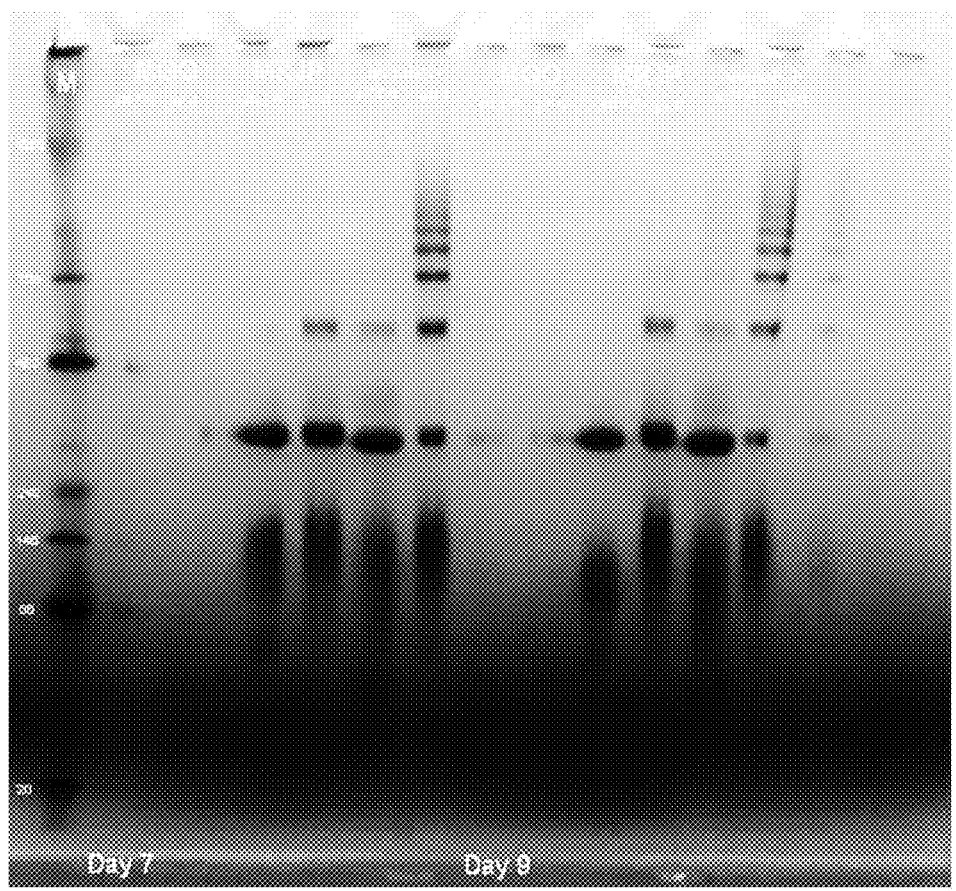
FIG. 5: Native PAGE™ Novex® 4-16% Bris-Tri gel of MGO-modified MRJP at pH 4.0 and 7.0, day 7 and day 9. Lane 1: Protein Standard contains protein bands 20-12,000 kDa. Lane 2: MGO alone in PBS buffer, pH 7.4 after 168 h. Lane 3: MGO alone in 0.2 M sodium acetate buffer, pH 4.0 after 168 h. Lane 4: MRJP in PBS buffer, pH 7.4 after 168 h. Lane 5: MRJP in 0.2 M sodium acetate buffer, pH 4.0 after 168 h. Lane 6: MRJP reacted with MGO in PBS buffer, pH 7.4 after 168 h. Lane 7: MRJP reacted with MGO in 0.2 M sodium acetate buffer, pH 4.0 after 168 h. Lane 8: MGO alone in PBS buffer, pH 7.4 after 216 h. Lane 9: MGO alone in 0.2 M sodium acetate buffer, pH 4.0 after 216 h. Lane 10: MRJP in PBS buffer, pH 7.4 after 216 h. Lane 11: MRJP in 0.2 M sodium acetate buffer, pH 4.0 after 216 h. Lane 12: MRJP reacted with MGO in PBS buffer, pH 7.4 after 216 h. Lane 13: MRJP reacted with MGO in 0.2 M sodium acetate buffer, pH 4.0 after 216 h. Lane 14: No sample loaded here but there was a sample overflow from lane 13. Lane 15: No sample (empty)

The native PAGE results are presented in FIGS. 2-5. At pH 4.0 but not at pH 7.0, the formation of MRJP high molecular weight adducts is seen after 24 hours of MGO treatment (FIG. 2, Lane 7). At day 9, it is apparent that the majority of the 300 kDa hexamer is the likely source for the higher molecular weight adducts (FIG. 5, Lane 13).

Changes in the lower molecular weight species are less apparent, but it is expected that MGO modification on the royalactin monomeric form of MRJP1 has also occurred. It may not be as readily apparent due to preclusion of higher molecular weight adducts from the gel. Visible precipitate was observed on the bottom of the micro centrifuge tube upon the centrifugation.

Example 2

Incubation of Major Royal Jelly Proteins in the Presence of MGO and Resulting Inhibitory Activity After partial thawing, the MRJP mixture was dissolved in PBS (pH 7.4) at a concentration of 50 mg/ml. This mixture was stirred for 30 to 60 minutes. The resulting cloudy solution was clarified by centrifugation (10,000 rpm for 10 minutes). The protein content was determined as 5.0±0.5 mg/ml. The pH of the solution was 3.8.

For the modification with MGO, 900 µl protein solution was mixed with 100 µl aqueous MGO solution (5%) The 5% MGO stock solution was produced by adding 125 µL of 40% MGO to 875 µL of water. To obtain the final MGO concentration of 0.15% reaction, 30 µL of 5% MGO was added to 970 µL of protein solution and incubated at 22° C. (set temperature) or allowed to sit out at ambient room temperature (RT) for 1 to 10 days. The set temperature of 22° C. was maintained using a water bath.

After each incubation interval, unreacted MGO was removed on a HiTrap™ desalting column (5 ml, GE healthcare). The protein was eluted with PBS buffer (25 mM, pH 7.4) at a flow rate of 2 ml/min. Eluting compounds were detected by UV absorbance at 214, 280 and 330 nm. Alternatively, the elution was carried out in sodium acetate buffer (10 mM, pH 4.0). The chromatography was carried out on an Äkta-900™ system (GE-healthcare) under the control of UNICORN software.

To test for activity, MGO was removed by passing 500 µl of reaction mixture (MRJP+MGO) through a 5 ml HiTrap™ desalting column. 1 ml fractions were collected and tested in the DCFDA oxidation assay (see Carter W O, Narayanan P K, Robinson J P. Intracellular hydrogen peroxide and superoxide anion detection in endothelial cells. J Leukoc Biol. 1994 February; 55(2):253-8) and in the Cathepsin B assay (see below) to determine for the presence of reactive species as well as Cathepsin B inhibitors.

The desalting fractions 1-3 containing the high molecular weight proteins were also analyzed for the presence of free amines using TNBS and absorbance at 280 and 330 nm determined as well as fluorescence profile. The numbers were normalized to protein concentration and difference between the starting MRJP and MGO-modified MRJP determined to identify amino acids involved in the activity associated with Cathepsin B inhibition.

Figure 6A:
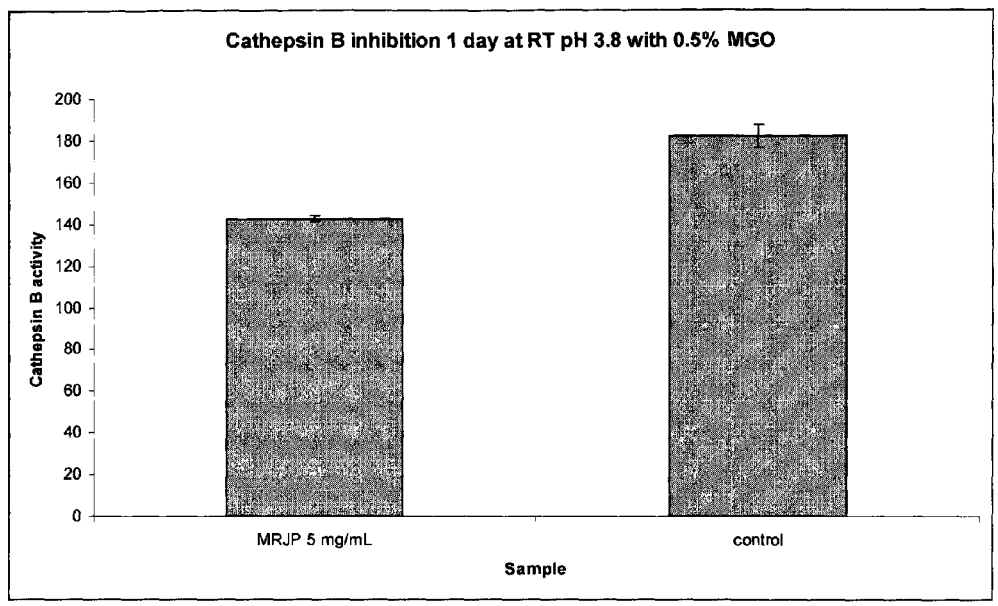
FIG. 6A: Inhibition of Cathepsin B with 0.5% MGO at pH 3.8, incubation for 1 day.
Figure 6B:
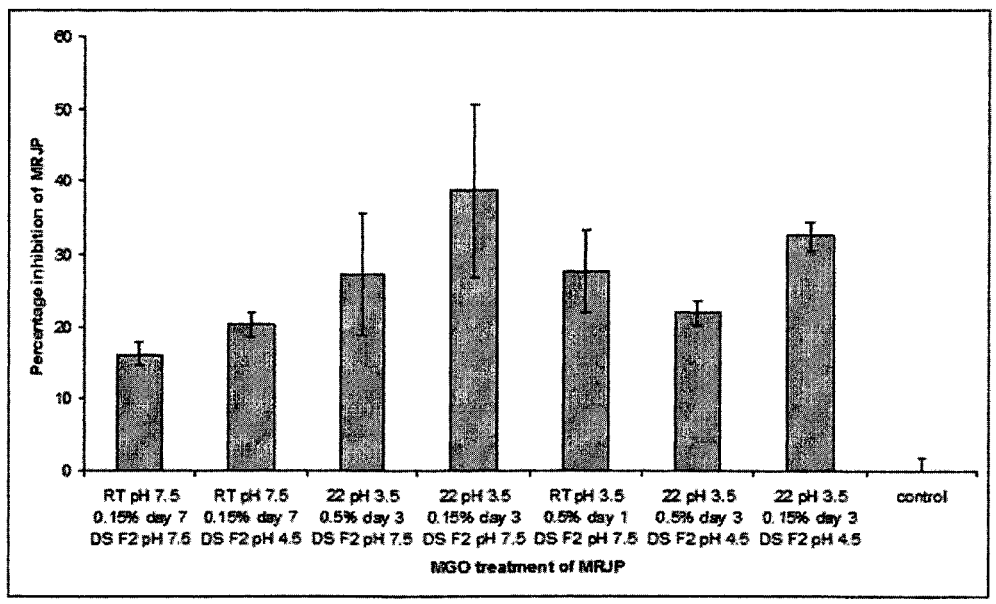
FIG. 6B: Inhibition of Cathepsin B with 0.15% MGO and 0.5% MGO modification of MRJP at 22° C. (set temperature) or RT (ambient room temperature).

Activity is observed after overnight treatment under the following conditions: 0.5% MGO, room temperature incubation at pH 3.8, with 5 mg/ml MRJP (FIG. 6A). Such treatment produces the most rapid production of Cathepsin B inhibitory activity. Inhibition of Cathepsin B is also found using modification with 0.15% MGO and 0.5% MGO at room temperature. See FIG. 6B. When the lower MGO concentration of 0.15% is used for MRJP modification, activity is only apparent after longer incubation periods. The reaction products were separated using GE Healthcare desalting column and the high MW fractions that were free of MGO were tested for cathepsin B activity. The gel filtration was performed either at pH 7.5 in PBS or at pH 4.5 in 100 mM sodium acetate buffer. Fractionation was performed under conditions that corresponded to the conditions used for MGO modification either at pH 7.5 or at pH 3.5. This is in contrast to the higher MGO concentration. A similar trend was observed for pH, whereby acidic pH produced inhibitory activity at a faster rate by comparison to pH 7.4. See FIG. 6B.

Example 3

Assay for Cathepsin B Activity

Cathepsin B was obtained from Sigma (C6286-25UN Cathepsin B from bovine spleen). The enzyme was prepared by adding 1 mL of 100 mM sodium acetate pH 4.5 containing 2 mM EDTA and 2 mM 2-mercaptoethanol to the enzyme vial. This activated the Cathepsin B. For assays, 50 µl of activated Cathepsin B was diluted with 5 mL of the assay buffer (100 mM sodium acetate pH 4.5 containing 2 mM EDTA and 2 mM 2-mercaptoethanol). 50 µl was used per well in a 96 well plate.

Assays were performed in duplicate and repeated in replicates of four for active material. To each well of a 96 well plate, 100 µl of assay buffer was added, followed by 50 µl of sample and 50 µl of Cathepsin B (stock 5.25 mg/mL having 12.5 U/mg) diluted 1:100 to 52.5 µg/mL for use in the assay. Total amount of cathepsin B in the assay was 2.625 µg. The plate was allowed to incubate at 37° C. for up to 10 minutes. However, routine analysis was performed with 2-5 minutes of incubation.

The addition of the substrate was used to initiate the reaction, Na—CBZ-L-lysine p-nitrophenyl ester (CLN) (Sigma C 3637) (Z-Lys-pNP). The protocol was performed similar to that described by O'Neil et al., 1996. 27 mg of substrate was dissolved in 1 mL of DMSO and then 50 µl of the stock substrate solution was mixed with 5 mL of assay buffer (100 mM sodium acetate pH 4.5 containing 2 mM EDTA and 2 mM 2-mercaptoethanol). 50 µl of the substrate was added to each well of a 96 well plate. A row of eight wells of the 96 well plate was assayed during each run.

The plate was read in a SpectraMax® M4 plate reader incubated at 37° C. The plate was agitated for 10 seconds and for 3 seconds between each read. The Vmax rate change in absorbance at 330 nm was read over 2 minutes with 10 s interval between reads. A delay of 30 seconds was used for the analysis. The linear portion of the curve was used to calculate the Vmax (milli units/min) The average of duplicate readings was performed. Active fractions were tested again to confirm activity.

Example 4

Identification of Amino Acid Residues Involved in Cathepsin B Inhibition

Figure 7:
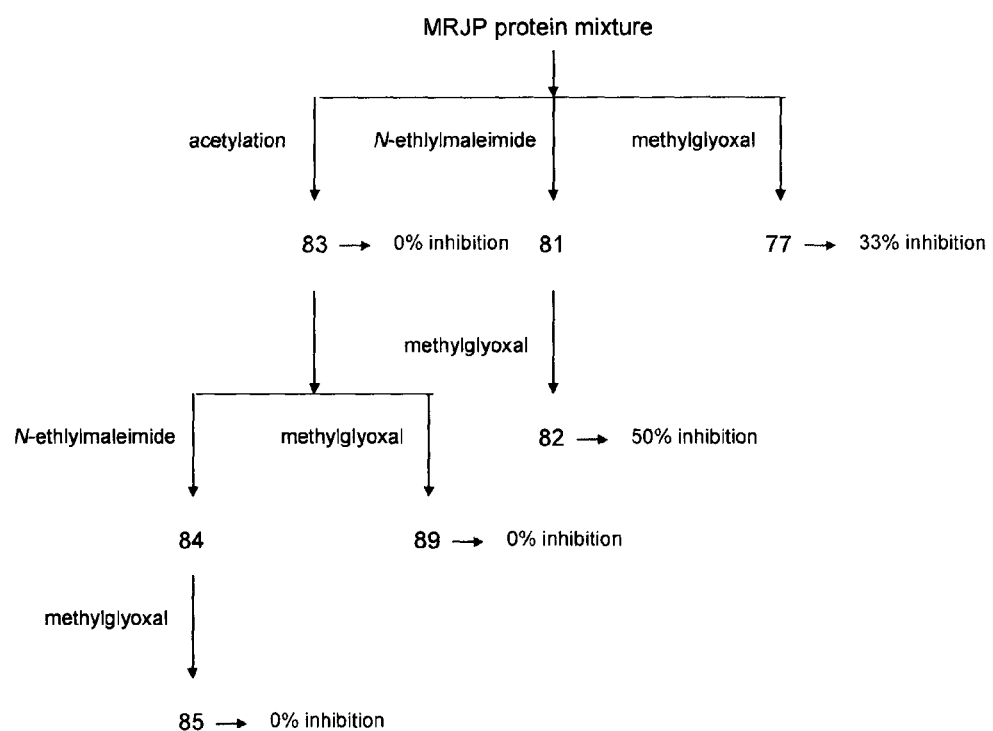
FIG. 7: Schematic chart of MRJP modification by acetic anhydride (reaction with epsilon amino group), N-ethyl maleimide (NEM) (blocking of cysteine residues) and MGO (reaction with Arg, Lys and Cys residues).

The following methods were employed to demonstrate which amino acids residues were important for Cathepsin B inhibition. The MRJP were either treated with MGO (product 77), acetic anhydride (blocking lysine residues) (product 83) or N-ethylmaleimide (NEM) (product 81). These last two samples were then further treated with MGO (yielding products 89 and 82, respectively). A sample of the acetylated MRJP (product 83) was taken and further reacted with NEM (yielding product 84). This sample was then further treated with MGO (yielding product 85). See reaction schematic in FIG. 7.

Modification of MRJP Mixture with MGO to Give Product 77

After partially thawing, the MRJP mixture was dissolved in PBS (pH 7.4) at a concentration of 50 mg/ml by stirring for 30 to 60 minutes. The resulting cloudy solution was clarified by centrifugation (10,000 rpm for 10 minutes). The protein content was determined as 5.0±0.5 mg/ml. The pH of the solution was 3.8.

For the modification with MGO, 900 µl protein solution was mixed with 100 µl aqueous MGO solution (5%) and incubated at 22° C. for 1 to 10 days. The temperature was maintained by incubation in a water bath.

After each incubation interval, unreacted MGO was removed on a HiTrap™ desalting column (5 ml, GE healthcare). The protein was eluted with PBS buffer (25 mM, pH 7.4) at a flow rate of 2 ml/min. Eluting compounds were detected by UV absorbance at 214, 280 and 330 nm. Alternatively, the elution was carried out in sodium acetate buffer (10 mM, pH 4.0). The chromatography was carried out on an Äkta-900™ system (GE-healthcare) under the control of the UNICORN software.

Modification of MRJP Mixture with NEM to Give Product 81

The MRJP mixture was dissolved in sodium phosphate buffer (pH 9.6) at a concentration of 50 mg/ml by stirring for 30 to 60 minutes. The resulting slightly cloudy solution was clarified by centrifugation (10,000 rpm for 10 minutes). The protein content was determined as 5.0±0.5 mg/ml. The pH of the solution was 7.5.

To 1 ml of the protein solution 53 µl of NEM solution (200 mM in PBS) were added and the mixture was stirred for 1 hour at room temperature. Unreacted NEM was removed on a HiTrap™ desalting column (5 ml, GE healthcare). The protein was eluted with sodium acetate buffer (10 mM, pH 4.0) at a flow rate of 2 ml/min. Eluting compounds were detected by UV absorbance at 214, 280 and 330 nm.

Modification of NEM-Treated MRJP with MGO to Give Product 82

Protein containing fraction from the desalting column (fraction 2) was modified with MGO as described above. Briefly, 900 µl of fraction 2 were reacted with 100 µl MGO (5%) at 22° C. overnight. Unreacted MGO was removed on a HiTrap™ desalting column (5 ml, GE healthcare). The protein was eluted with PBS buffer (25 mM, pH 7.4) at a flow rate of 2 ml/min. Eluting compounds were detected by UV absorbance at 214, 280 and 330 nm. Alternatively, the elution was carried out in sodium acetate buffer (10 mM, pH 4.0).

Acetylation of MRJP Mixture to Give Product 83

1.2814 g of defrosted RJP mixture was dissolved in 50 mL of Tris/HCl (0.1 M, pH 8.5) containing 6 M urea. The solution was cooled down on an ice water bath. Acetic anhydride was added every 20 minutes in aliquots of 0.5 ml over a period of 2 hours. The pH of the solution was determined before every addition and adjusted to a pH above 7.5 using Tris/HCl buffer (1 M, pH 8.5).

The sample was transferred to a dialysis tubing (molecular weight cut off 10 kDa) and dialysed over night against 1.6 liters of water with three changes of dialysate. The content of the dialysis tubing was frozen and freeze dried. 239.9 mg of a white slightly sticky material was recovered.

Modification of Acetylated MRJP Mixture with NEM to Give Product 84

The concentrated protein solution (500 µl) was diluted with 500 µl PBS (25 mM, pH 7.4), 53 µl of NEM solution (200 mM in PBS) were added and the mixture was stirred for 1 hour at room temperature. Unreacted NEM was removed on a HiTrap™ desalting column (5 ml, GE healthcare). The protein was eluted with sodium acetate buffer (10 mM, pH 4.0) at a flow rate of 2 ml/min. Eluting compounds were detected by UV absorbance at 214, 280 and 330 nm.

Modification of NEM-Treated Acetylated MRJP with MGO to Give Product 85

Protein containing fraction from the desalting column (fraction 2) was modified with MGO as described above. Briefly, 900 µl of fraction 2 were reacted with 100 µl MGO (5%) at 22° C. overnight. Unreacted MGO was removed on a HiTrap™ desalting column (5 ml, GE healthcare). The protein was eluted with PBS buffer (25 mM, pH 7.4) at a flow rate of 2 ml/min. Eluting compounds were detected by UV absorbance at 214, 280 and 330 nm. Alternatively, the elution was carried out in sodium acetate buffer (10 mM, pH 4.0).

Results from NEM, Acetylation, and MGO Modifications

The samples after treatment with MGO were desalted with a 5 mL HiTrap™ desalting column and fraction 2 containing the high molecular weight proteins were analysed for their ability to inhibit Cathepsin B. The assay for Cathepsin B activity is detailed further above.

Figure 8:
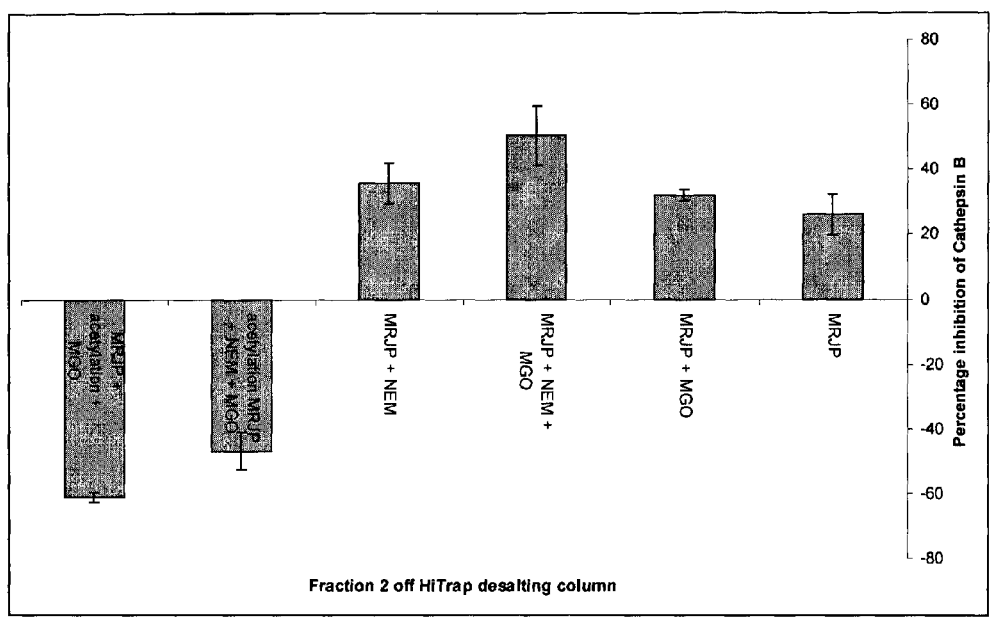
FIG. 8: Cathepsin B inhibition after treatment of MRJPs with NEM, acetic anhydride, and MGO.

MRJP treated with MGO produced inhibitory activity (FIG. 8). Inhibitory activity was also observed for the NEM plus MGO treated MRJP sample. However, upon acetylating MRJP and treating with MGO (product 89; see schematic in FIG. 7), all inhibitory activity was lost, providing evidence that MGO modification of lysine residues is important for Cathepsin B inhibitory activity (FIG. 8). After acetylation of the lysine residues of MRJP, the proteins appeared to stimulate rather than inhibit Cathepsin B activity (FIG. 8).

It is noted that NEM is also a cysteine protease inhibitor. Our results showed that NEM modification followed by MGO modification produced greater inhibition of Cathepsin B. This was attributed to residual NEM remaining in the samples of MGO-modified protein, allowing the NEM to act in combination with the MGO-modified protein and to further inhibit Cathepsin B activity.

Thus, in summary, MGO reaction with MRJP produces a Cathepsin B inhibitor. Blocking thiol groups with NEM followed by MGO treatment also produces an active inhibitor of Cathepsin B. Acetylation of MRJP followed by reaction with MGO prevented the production of the Cathepsin B inhibitory activity. Acetylation followed by NEM treatment to block both lysine and cysteine residues on MRJPs followed by MGO treatment also failed to produce an active Cathepsin B inhibitor.

It has been demonstrated in PCT/NZ/2011/000271 that acetylation selectively blocks lysine residues. As noted above, the acetylated MRJP sample was found to lack activity after addition of MGO. This indicated that the MGO modification of lysine residues is important for the functional activity seen by modified MRJP in relation to the formation of a reactive form of MGO on the surface of the protein.

To confirm these results, another sample prepared in an identical fashion was tested for its ability to inhibit Cathepsin B. The acetylated proteins from royal jelly were unable to inhibit Cathepsin B, even after optimal MGO treatment, i.e., 0.5% MGO at pH 3.5, 22° C. overnight. The speed by which this could be done making it preferred over the other methods outlined in FIG. 6B which took from 3-7 days to generate similar levels of cathepsin B inhibitory activity. It was concluded that MGO modification of lysine is a key factor in Cathepsin B inhibitory activity.

Example 5

Cathepsin B Digestion of MGO-Modified MRJP

Cathepsin B working reagent solution was prepared (1:50) from Cathepsin B stock solution in the buffer system containing 100 mM sodium acetate, 2 mM EDTA and 2.5 mM 2-mercaptoethanol, pH 5.0.

Cathepsin digestion was performed on selected samples of SEC fractions. Typically, 10 µl of Cathepsin B working solution was mixed with 20 µl of protein sample and digested at 37° C. for overnight. After hydrolysis, the digests were prepared for native PAGE analysis. The gel was stained with Coomassie® G250 as shown in FIG. 9, see Lanes 7-10.

Samples used in the Cathepsin B digestion were: 1) Crude MRJP protein; 2) Desalted fraction (first big peak) of MGO-modified MRJP at pH 4.0 for 9 days sample; 3) Desalted fraction (first big peak) of MGO-modified MRJP in PBS (pH 7.5) for 9 days sample; 4) SEC fractions of pH 5.0 fractions; 5) SEC fractions of reaction 221.

Figure 9:
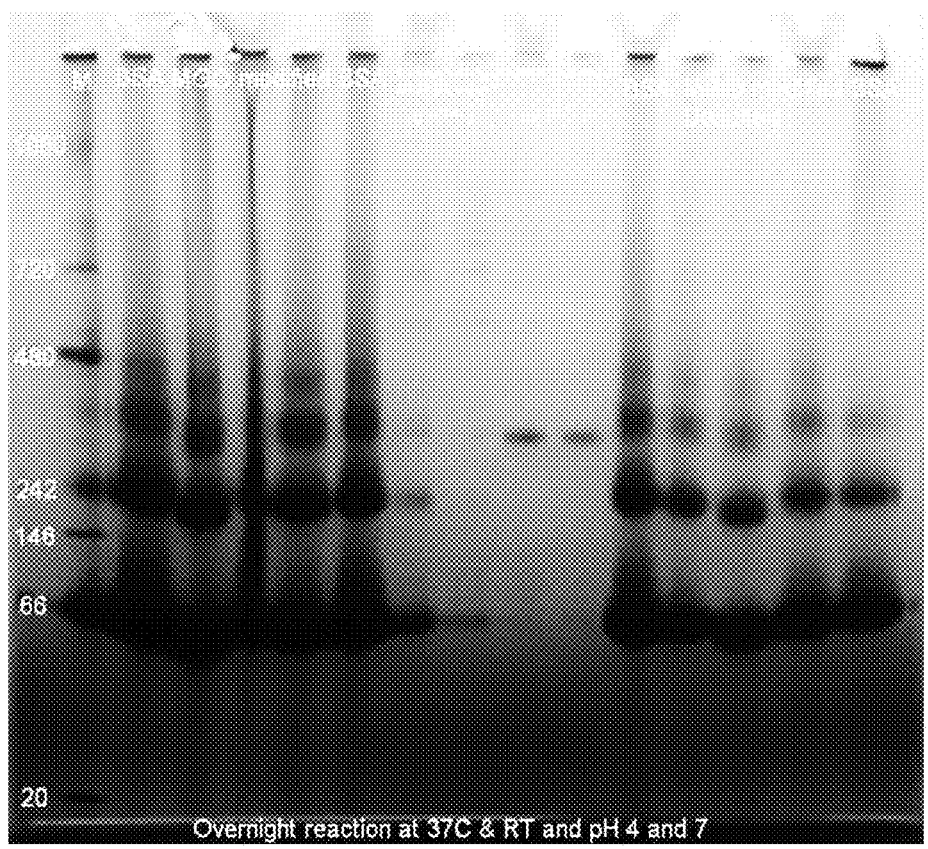
FIG. 9: Native PAGE™ Novex® 4-16% Bris-Tri gel of MGO-modified BSA and Cathepsin B hydrolysis of MGO-modified MRJP. Cathepsin B hydrolysis was performed on MGO-modified MRJP prepared at either pH 4.0 or 7.0. Lane 1: Protein standard contains protein bands 20-12,000 kDa. Lane 2: BSA control in PBS, pH 7.4, 37° C., overnight. Lane 3: MGO-modified BSA reaction in PBS pH 7.4, 37° C., overnight. Lane 4: MGO-modified BSA reaction in 0.2 M sodium acetate buffer pH 4.0, 37° C., overnight. Lane 5: MGO-modified BSA reaction in PBS pH 7.4, room temperature, overnight. Lane 6: MGO-modified BSA reaction in 0.2 M sodium acetate buffer pH 4.0, room temperature, overnight. Lane 7: Desalted fraction of MOO-modified MRJP at pH 4/9 days without Cathepsin B digestion. Lane 8: Desalted fraction of MGO-modified MRJP at pH 4/9 days with Cathepsin B digestion. Lane 9: Desalted fraction of MGO-modified MRJP at pH 7.5/9 days without Cathepsin B digestion. Lane 10: Desalted fraction of MGO-modified MRJP at pH 7.5/9 days with Cathepsin B digestion. Lanes 11 to Lane 15: Same as Lane 2 to Lane 6 but desalted before loading into the gel.
Figures 11A, 11B, 11C:
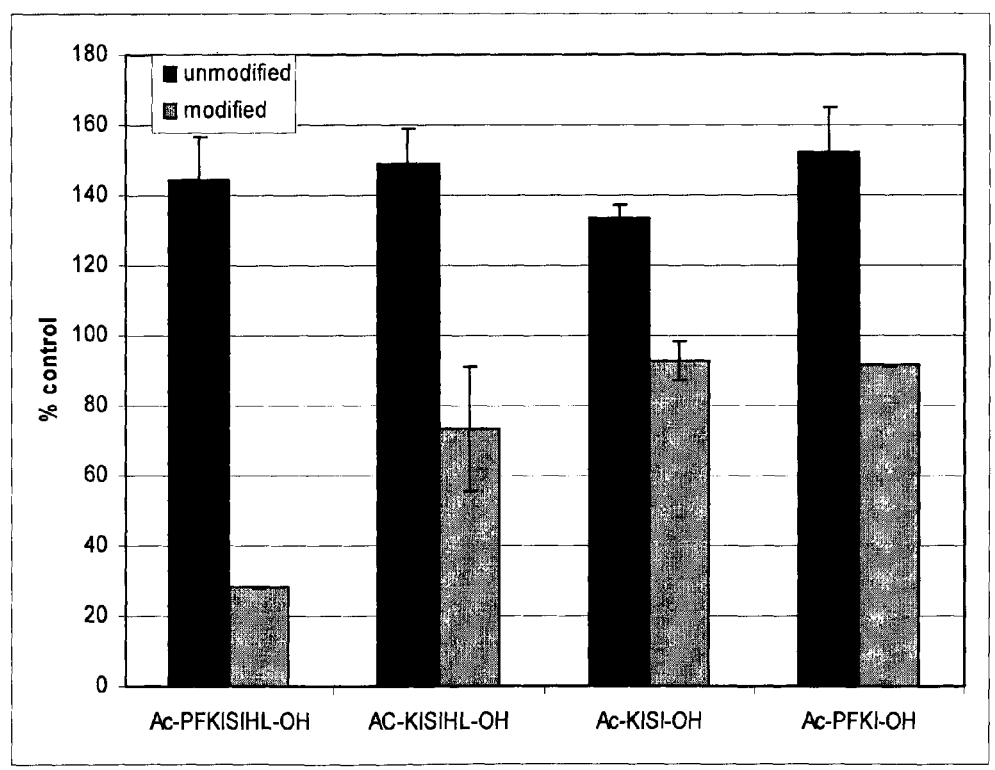
FIGS. 11A-C: Inhibitory activity of peptides derived from the C-terminus of MRJP1.
Figures 12A, 12B, 12C:
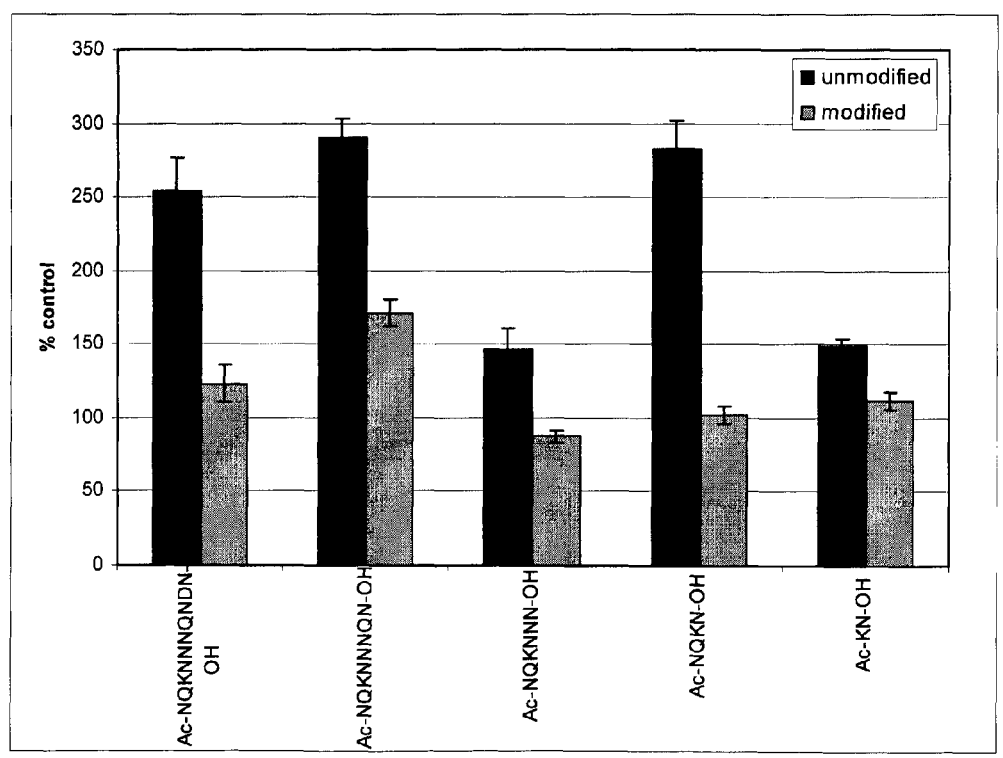
FIGS. 12A-C: Inhibitory activity of peptides derived from the C-terminus of MRJP2.
Figures 13A, 13B, 13C:
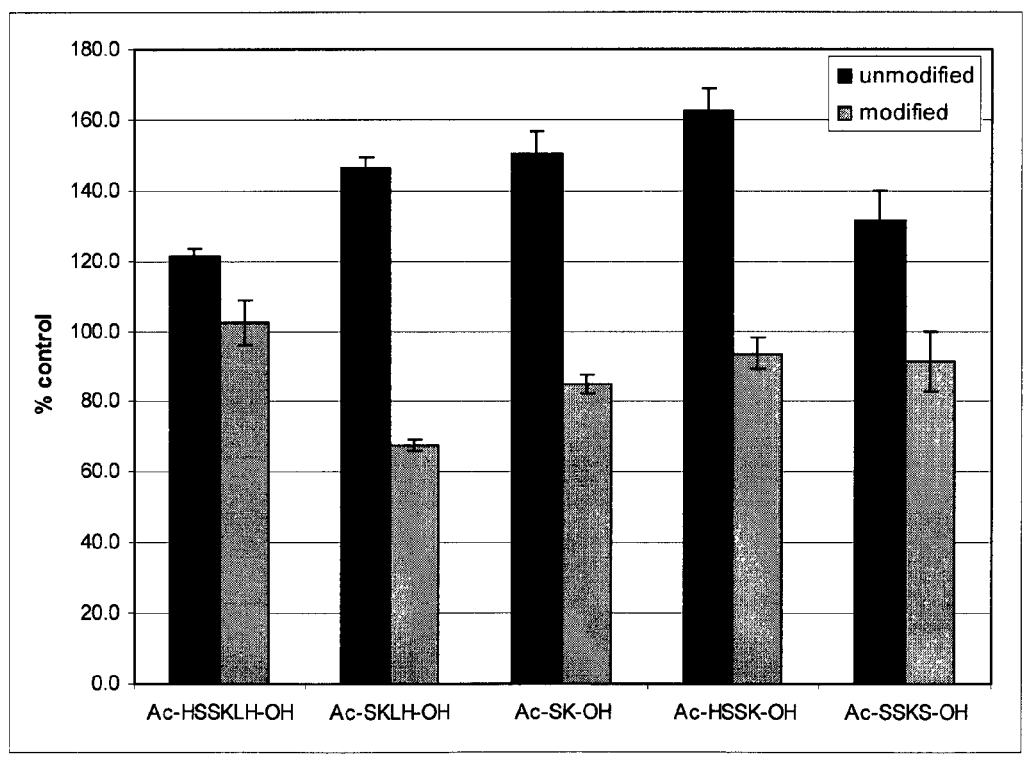
FIGS. 13A-C: Inhibitory activity of peptides derived from the C-terminus of MRJP3.
Figures 14A, 14B, 14C:
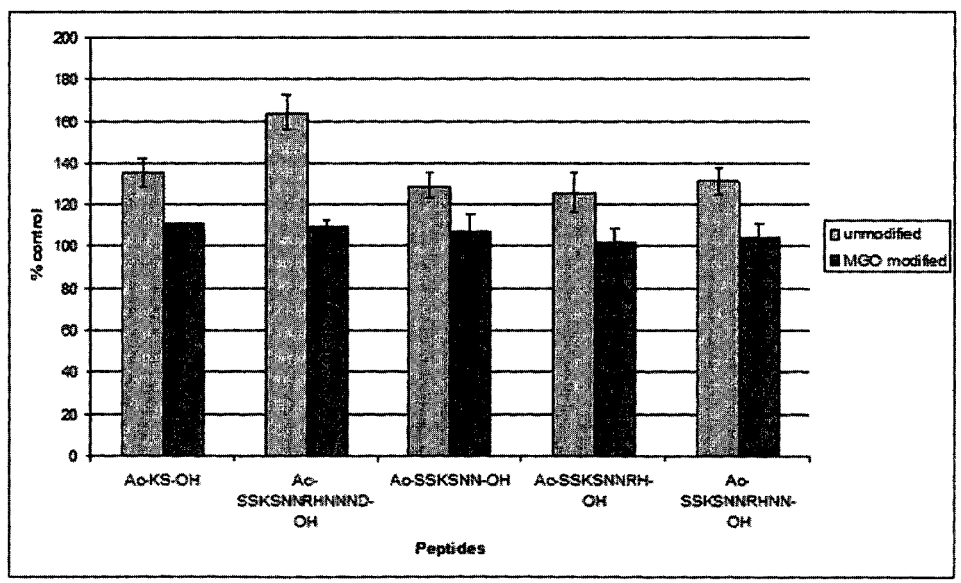
FIGS. 14A-C: Inhibitory activity of peptides derived from the C-terminus of MRJP4.
Figures 15A, 15B, 15C:
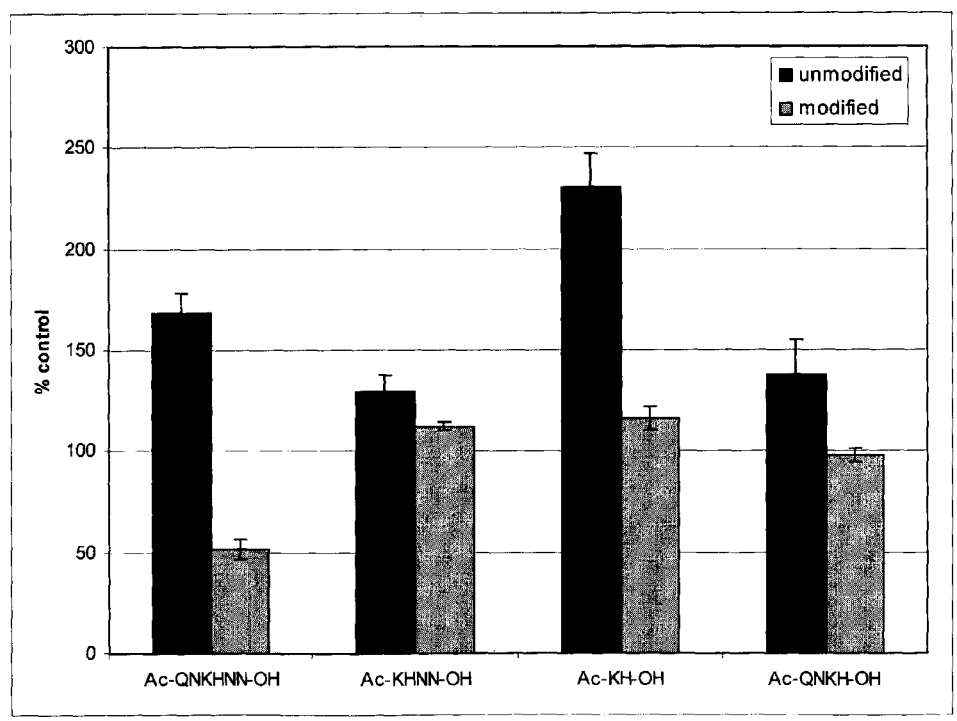
FIGS. 15A-C: Inhibitory activity of peptides derived from the C-terminus of MRJP5.

Results are depicted in FIG. 9. Lane 1 shows native PAGE molecular weight markers, Lane 7 shows the undigested MGO-modified MRJP at pH 4.0, Lane 8 shows the Cathepsin B digested MGO-modified MRJP at pH 4.0, Lane 9 shows undigested MGO-modified MRJP at pH 7.0, and Lane 10 shows Cathepsin B digested MGO-modified MRJP at pH 7.0.

At pH 4.0, which is the anticipated pH of honey, high molecular weight adducts (>480 kDa) of MRJPs are formed (see FIG. 9, Lane 7 and FIG. 2, Lane 5). These bands are not evident when the MGO modification is performed at pH 7.0 (see FIG. 9, Lanes 9-10). Thus, Cathepsin B is unable to hydrolyze the protein at pH 7.0 but was able to hydrolyze the lower molecular weight species produced at pH 4.0. The higher molecular weight species at pH 4.0 appeared to be more resistant to proteolysis than the lower molecular weight species. However, the species produced by MGO-modification of the MRJP at pH 7.0 appeared also to be resistant to hydrolysis.

Without wishing to be limited by theory, the inability of Cathepsin B to hydrolyze MRJP is proposed to be due to inhibition of this enzyme. We refer to FIG. 9. In contrast, the native hexamer form of MRJP1 and the monomeric form of royalactin were readily degraded by this enzyme (data not shown).

Notably, the level of protein loaded in the gel varied where 25% less protein was loaded for the hydrolyzed samples. For hydrolysis, 10 µL of a 1 mg/mL solution (10 µg) of Cathepsin B was used. Thus, a very high level of enzyme activity was employed for these experiments. Moreover, the reaction was performed over two days at 37° C. Under these conditions, we expected to see complete or near complete hydrolysis of the MRJP proteins.

As Cathepsin B has an exopeptidase activity at pH 4.0, it was expected that dipeptides would be generated from the hydrolysis that cannot be seen by native PAGE analysis. The incomplete hydrolysis we observed suggests that some Cathepsin B inhibition occurred, and/or the length of time and concentration of Cathepsin B was higher than the inhibitory activity of the MGO-modified MRJP proteins. This may have allowed partial hydrolysis of the 58 kDa protein (MRJP1) and the band present around 242 kDa.

By comparison, the larger cross-linked complexes did not appear to be susceptible to Cathepsin B cleavage at pH 4.0. Cross-linking of proteins with MGO occurs between lysine residues or lysine and Arg residues. At pH 7.0, the hydrolysis of the oligomeric complex of MRJP proteins was not hydrolyzed by Cathepsin B. This was attributed to the substrate specificity of Cathepsin B at this pH being limited to cleavage at Arg-Arg|Xaa sequences within the MRJP proteins, i.e., endopeptidase activity.

Yet, this site within MRJPs does not appear to be available for cleavage. The protein level observed on the gel after substantial hydrolysis with Cathepsin B is essentially the same as that observed without the addition of Cathepsin B. It is possible that Cathepsin B was completely inhibited under these conditions. MGO modification of Arg residues is also likely. This would prevent recognition of the MRJP cleavage site for Cathepsin B at pH 7.0. It is also possible that the native gel electrophoresis failed to separate the protein fragments sufficiently.

Example 6

Proposed Mechanism of Cathepsin B Inhibition

Cathepsin B is a thiol protease that participates in intracellular degradation and turnover of proteins. It is an important enzyme in the phagocytosis process and it has also been implicated in tumor invasion and metastasis.

The primary specificity of Cathepsin B is for cleavage sites Arg-Arg-|-Xaa (where | indicates the point of cleavage). The MRJPs would be predicted to be suitable substrates for this enzyme due to the presence of an Arg-Arg peptide sequence in MRJP1-5. However, the significance of this cleavage site has been questioned by our results. In particular, MGO-modified bovine serine albumin that has the same Arg-Arg peptide sequence shows no anti-inflammatory activity, in contrast to the MGO-modified MRJP1 and MRJP3 proteins (results not shown). The results indicate that Arg-Arg cleavage may only be relevant for plasma membrane bound Cathepsin B at optimal conditions of pH 7 (data not shown).

Cathepsin B also has some C-terminal dipeptidase activity (Brömme et al., 1987 and Chapman et al., 1994). Without wishing to be bound by theory, it is proposed that the C-terminal peptide regions of MGO-modified MRJP1 and MGO-modified MRJP3 are inhibiting the activity of Cathepsin B. It is proposed that the MGO-modified lysine, which can be involved in thiol lysine cross-links, is in close proximity to the thiol active site of Cathepsin B. In this way, the MGO on the lysine is reacting with the thiol active site of Cathepsin B, and inhibiting its action.

Notably, MRJP1 has a lysine (see SEQ ID NO: 1 at 427) that is 3 cleavage sites from the C-terminus end. MRJP3 has a lysine residue at the first cleavage site at 542 (see SEQ ID NO: 3). Similarly, MRJP2 has a lysine residue at the fourth cleavage site at 445 (see SEQ ID NO: 2) and MRJP 4 has a lysine residue at the fifth cleavage site at 455 (see SEQ ID NO: 4). MRJP 5 has a lysine residue at the second cleavage site at 595 (SEQ ID NO: 5). MRJP6 has a lysine residue at the 3rd cleavage site at 431 (see SEQ ID NO: 6). MRJP8 has a lysine at the 4th cleavage site at 409 (see SEQ ID NO: 8) and MRJP 9 has a lysine at the fourth cleavage site at 415 (see SEQ ID NO: 9).

Bovine serum albumin does not have a lysine at the C-terminus until the fifth cleavage point of Cathepsin B. In this way, the lysine residue in MGO-modified BSA may be too far away to inhibit Cathepsin B. Moreover, the lysine residue at 573 in BSA is involved in an alpha helical structure and not readily available for cleavage by Cathepsin B. It is therefore postulated that the inhibitory activity of MGO-modified MRJP1 and MRJP3 is seen because of the relatively close proximity of the lysine to the C-terminus end of the peptide. It is anticipated also that MGO-modified MRJP2, MRJP4, MRJP5, MRJP6, MRJP8, and MRJP9 will also show Cathepsin B inhibitory activity.

The presence of a reactive MGO species on the surface of the protein was also detected using DCFDA oxidation to fluorescein (data not shown). The reaction of hydrogen peroxide with MGO led to a reaction in the level of DCFDA oxidized and therefore leads to a reduction in the level of fluorescence detected (data not shown). Isolation of high molecular weight proteins using gel filtration or HiTrap™ desalting led to the identification of a highly reactive species on the surface of the protein. This species as seen by DCFDA analysis correlates to the Cathepsin B inhibitory activity (data not shown).

It is known that the Arg-MGO adduct formation is favored under lower MGO concentrations and this leads to an irreversible adduct that can be detected with absorbance at 330 nm or fluorescence Ex330 nm and Em410 nm. The reaction with Cys residues forms a hemiacetyl that is reversible and unstable leading to release of MGO off the surface of the protein. The reaction with lysine can form both reversible and irreversible reactions with MGO.

The initial adduct formed is slowly rearranged to form a stabilized covalently linked MGO attached to the epsilon amino group of lysine. Further rearrangements can occur, leading to the generation of various chemical functionality including $N(\epsilon)$-(carboxyethyl)lysine (CEL) acid group, hydroxyl group, aldehyde or ketone functionality as well as the irreversible reactions with other protein to form cross-links.

MGO modification can lead to reactive species such as aldehydes bound to the protein, and aldehydes can react with the thiol of the Cathepsin B active site. From this, it is possible that inhibition of Cathepsin B may occur between MGO-modified lysine residues with an aldehyde functionality. Lysines are also of interest in Cathepsin B inhibition, as bound MGO can undergo a cannizzaro rearrangement forming CEL and a hydroxyl group, which has carboxylic acid functionality. Two aldehydes react, where one aldehyde is reduced to a corresponding alcohol, while the second aldehyde is oxidized to carboxylic acid.

At pH 4.0, Cathepsin B has a C-terminal exodipeptidase activity. It is hypothesized that the acid functionality present in the CEL, carboxylic acid moiety may be recognized by Cathepsin B as a C-terminus. This would place the peptide in an orientation that prevents cleavage. Both structures are potentially formed by MGO upon reaction with lysine. Various reaction pathways are likely to be favored under various conditions.

The chemical reactivity of MGO under acidic conditions, as present in Manuka honey, appears to enable formation of high molecular weight cross-links. This would appear to favor aldehyde formation, which, in turn, continues to react to form protein cross-links. The cannizzaro rearrangement is favored under basic conditions, which is more likely to occur when MRJP proteins are reacted at neutral pH 7.0. The cannizzaro rearrangement prevents further cross-linking between proteins. The aldehyde functional group that is involved in cross-linking is replaced with an acid group and a hydroxyl group. The hydroxyl provides further diversification of the chemistry on the surface of lysine residues after MGO modification and this can provide changes in inhibitory selectivity and affinity.

As noted above, we observed that blocking lysine residues with acetic anhydride followed by MGO-modification blocks Cathepsin B inhibition. This highlights the importance of lysines in producing inhibitory activity. The reaction of lysine epsilon amino groups with acetic anhydride produces an amide bond. This removes the features required for recognition by the C-terminal exopeptidase activity of Cathepsin B. This, in turn, abolishes enzyme interaction and inhibition.

Example 7

MGO Modification of Synthetic Peptides and their Inhibitory Activity

Thirty-seven synthetic peptides were supplied by Mimotopes Pty Ltd (Melbourne, Australia). The structures were based on peptide sequences in MRJP 1-5. Particular focus was placed on the C-terminus of these proteins.

MGO modification was performed as follows. The incubation mixture included 180 µl peptide solution (5 mM) and 20 µl MGO solution (5%). Incubation was carried out overnight at room temperature. MGO was removed using C18 SPE cartridges. Eluted peptides were concentrated and solutions made up to original concentration.

The test for inhibition of Cathepsin B activity was carried out with solutions containing 2 mM of unmodified or modified peptide according to the previously described procedure. The synthetic peptides and results are shown in FIGS. 11A-C, 12A-C, 13A-C, 14A-C, and 15A-C, and Tables 1-5, below.

TABLE 1

Synthetic peptides derived from the C-terminus of MRJP1

| peptide | SEQ ID NO: | unmodified | MGO-modified |
|---|---|---|---|
| Ac-PFKI-OH | 22 | 152.05 ± 13.20 | 91.45 ± 0.11 |
| Ac-KISI-OH | 21 | 133.11 ± 4.29 | 92.82 ± 5.44 |
| Ac-KISIHL-OH | 20 | 149.04 ± 9.65 | 73.23 ± 17.90 |
| Ac-PFKISIHL-OH | 19 | 144.22 ± 12.20 | 28.11 ± 0.06 |

TABLE 2

Synthetic peptides derived from the C-terminus of MRJP2

| peptide | SEQ ID NO: | unmodified | MGO-modified |
|---|---|---|---|
| Ac-KN-OH | 28 | 149.55 ± 4.42 | 111.84 ± 6.21 |
| Ac-NQKN-OH | 27 | 282.39 ± 19.66 | 102.36 ± 6.36 |
| Ac-NQKNNN-OH | 26 | 146.89 ± 14.87 | 87.48 ± 4.31 |
| Ac-NQKNNNQN-OH | 25 | 290.25 ± 12.34 | 171.38 ± 9.10 |
| Ac-NQKNNNQNDN-OH | 24 | 254.04 ± 22.31 | 123.18 ± 12.85 |

TABLE 3

Synthetic peptides derived from the C-terminus of MRJP3

| peptide | SEQ ID NO: | unmodified | MGO-modified |
|---|---|---|---|
| Ac-HSSKLH-OH | 30 | 121.50 ± 2.05 | 102.36 ± 6.36 |
| Ac-SKLH-OH | 31 | 146.35 ± 2.91 | 67.57 ± 1.73 |
| Ac-SK-OH | 32 | 137.62 ± 9.65 | 115.94 ± 1.24 |

TABLE 3-continued

Synthetic peptides derived from the C-terminus of MRJP3

| peptide | SEQ ID NO: | unmodified | MGO-modified |
|---|---|---|---|
| Ac-HSSK-OH | 33 | 164.77 ± 3.87 | 134.68 ± 1.13 |
| Ac-SSKS-OH | 34 | 118.71 ± 9.09 | 107.49 ± 4.29 |

TABLE 4

Synthetic peptides derived from the C-terminus of MRJP4

| peptide | SEQ ID NO: | unmodified | MGO-modified |
|---|---|---|---|
| Ac-KS-OH | 41 | 135.26 ± 7.09 | 110.69 ± 0.89 |
| Ac-SSKSNNRHNNND-OH | 36 | 164.01 ± 8.57 | 109.55 ± 3.11 |
| Ac-SSKSNN-OH | 39 | 129.06 ± 6.31 | 107.043 ± 8.64 |
| Ac-SSKSNNRH-OH | 38 | 125.43 ± 9.56 | 101.92 ± 6.31 |
| Ac-SSKSNNRHNN-OH | 37 | 131.11 ± 6.491 | 104.11 ± 7.46 |

TABLE 5

Synthetic peptides derived from the C-terminus of MRJP5

| peptide | SEQ ID NO: | unmodified | MGO-modified |
|---|---|---|---|
| Ac-KH-OH | 45 | 230.49 ± 16.21 | 115.95 ± 5.94 |
| Ac-QNKHNN-OH | 43 | 167.90 ± 10.09 | 51.30 ± 5.31 |
| Ac-KHNN-OH | 44 | 129.26 ± 7.90 | 111.90 ± 2.07 |
| Ac-QNKH-OH | 46 | 137.67 ± 17.04 | 97.77 ± 3.70 |

From this analysis, the synthetic peptides of interest include: MRJP1: Ac-PFKISIHL-OH (SEQ ID NO: 19); MRJP2: Ac-NQKNNNQNDN—OH (SEQ ID NO: 24); Ac-NQKN—OH (SEQ ID NO: 27); MRJP3: Ac-SKLH-OH (SEQ ID NO: 31); and MRJP5: Ac-QNKHNN—OH (SEQ ID NO: 43); Ac—KH—OH (SEQ ID NO: 45).

Additional synthetic peptides were prepared based on the amino acid sequences of MRJP1, MRJP3, and MRJP5, in accordance with the procedure noted above.

TABLE 6

MRJP1 derived synthetic peptides

| sample | SEQ ID NO: | unmodified | MGO-modified |
|---|---|---|---|
| H-FDR-OH | 50 | 174.56 ± 11.96 | 71.18 ± 2.22 |
| Ac-FDR-OH | 53 | 85.57 ± 3.51 | 44.78 ± 1.54 |

TABLE 6-continued

MRJP1 derived synthetic peptides

| sample | SEQ ID NO: | unmodified | MGO-modified |
|---|---|---|---|
| H-HNIR-OH | 54 | 151.51 ± 0.62 | 103.38 ± 3.65 |
| Ac-HNIR-OH | 59 | 171.58 ± 11.29 | 106.82 ± 3.02 |
| H-YINR-OH | 85 | 142.33 ± 3.64 | 79.21 ± 2.12 |
| Ac-YINR-OH | 87 | 93.14 ± 2.42 | 99.05 ± 7.78 |
| H-FTK-OH | 88 | 147.63 ± 0.70 | 76.59 ± 2.24 |
| Ac-FTK-OH | 91 | 148.84 ± 16.13 | 105.35 ± 5.73 |
| H-IFVTMLR-OH | 92 | 80.48 ± 4.25 | 78.70 ± 3.67 |
| Ac-IFVTMLR-OH | 93 | 88.31 ± 12.62 | 92.63 ± 2.00 |
| H-MQK-OH | 94 | 127.00 ± 0.93 | 99.48 ± 2.95 |
| Ac-MQK-OH | 95 | 121.24 ± 3.57 | 69.15 ± 4.87 |
| H-CDR-OH | 96 | 165.10 ± 0.38 | 96.01 ± 6.45 |
| Ac-CDR-OH | 97 | 120.52 ± 8.17 | 78.51 ± 2.51 |
| H-MTR-OH | 98 | 143.48 ± 2.33 | 104.39 ± 2.68 |
| Ac-MTR-OH | 99 | 126.30 ± 8.12 | 118.90 ± 5.62 |
| TNBS-FAK-pNA | 100 | 99.27 ± 3.8 | 122.48 ± 7.65 |

TNBS = N-terminus blocked with trinitrobenzene sulphonic acid.
pNA = paranitroanalide.

TABLE 7

MRJP3 derived synthetic peptides

| sample | SEQ ID NO: | unmodified | MGO-modified |
|---|---|---|---|
| H-QNDNK-OH | 101 | 104.37 ± 4.99 | 68.42 ± 0.22 |
| Ac-QNDNK-OH | 102 | 167.26 ± 7.64 | 122.35 ± 3.05 |
| H-QNDNR-OH | 103 | 162.38 ± 16.36 | 116.16 ± 3.66 |
| Ac-QNDNR-OH | 104 | 161.75 ± 9.25 | 132.44 ± 4.77 |
| H-QNGNK-OH | 105 | 170.73 ± 5.14 | 118.80 ± 11.41 |
| Ac-QNGNK-OH | 106 | 187.34 ± 9.14 | 89.21 ± 10.96 |
| H-QNGNR-OH | 107 | 74.41 ± 4.98 | 84.99 ± 4.08 |
| Ac-QNGNR-OH | 108 | 101.30 ± 6.00 | 88.67 ± 4.38 |

TABLE 8

MRJP5 derived synthetic peptides

| sample | SEQ ID NO: | unmodified | MGO-modified |
|---|---|---|---|
| H-TNR-OH | 109 | 102.61 ± 5.34 | 91.86 ± 3.50 |
| Ac-TNR-OH | 110 | 96.48 ± 2.03 | 91.72 ± 0.84 |
| H-MDK-OH | 111 | 104.25 ± 2.73 | 70.62 ± 12.34 |
| Ac-MDK-OH | 112 | 109.67 ± 3.13 | 99.38 ± 1.63 |
| H-MDR-OH | 113 | 101.73 ± 2.37 | 74.46 ± 0.97 |
| Ac-MDR-OH | 114 | 107.34 ± 1.46 | 88.56 ± 2.14 |
| H-TDK-OH | 115 | 103.18 ± 4.50 | 87.53 ± 3.26 |
| Ac-TDK-OH | 116 | 100.51 ± 10.69 | 92.75 ± 2.41 |
| H-IDR-OH | 117 | 98.02 ± 2.54 | 85.60 ± 5.32 |
| Ac-IDR-OH | 118 | 93.46 ± 12.24 | 81.75 ± 3.26 |
| H-VNR-OH | 119 | 97.75 ± 10.62 | 82.63 ± 7.88 |
| Ac-VNR-OH | 120 | 99.83 ± 3.40 | 68.49 ± 8.73 |
| H-MHR-OH | 121 | 96.77 ± 9.26 | 80.66 ± 6.19 |
| Ac-MHR-OH | 122 | 101.26 ± 4.59 | 90.13 ± 17.28 |
| H-MNR-OH | 123 | 112.08 ± 6.03 | 78.56 ± 5.37 |
| Ac-MNR-OH | 124 | 100.83 ± 2.26 | 86.94 ± 3.01 |
| H-LQK-OH | 125 | 102.47 ± 4.27 | 95.26 ± 5.54 |
| Ac-LQK-OH | 126 | 102.05 ± 10.32 | 90.15 ± 1.52 |

Figures 16A, 16B:
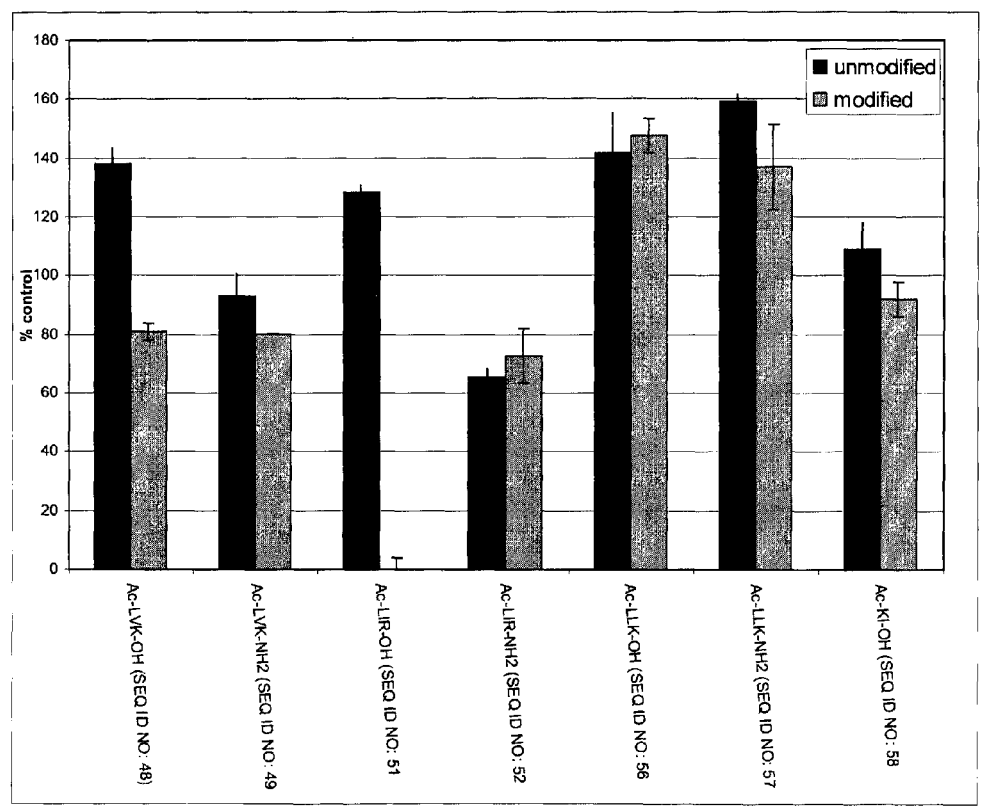
FIGS. 16A-B: Additional peptides tested for Cathepsin B inhibition.

Further synthetic peptides derived from MRJP1-5 were tested as described herein. The synthetic peptides and results are shown in FIGS. 16A and 16B, and Table 9, below.

TABLE 9

Additional synthetic peptides tested for inhibitory activity

| peptide | derived from MRJP | SEQ ID NO: | unmodified | MGO-modified |
|---|---|---|---|---|
| Ac-LVK-OH | MRJP3 (see Leu170) | 48 | 143.92 ± 3.15 | 80.84 ± 3.07 |
| Ac-LVK-NH2 | MRJP3 (see Leu170) | 49 | 92.71 ± 7.78 | 80.03 ± 0.10 |
| Ac-LIR-OH | MRJP2, 4 (see Leu408) | 51 | 128.28 ± 2.50 | 0.07 ± 3.96 |
| Ac-LIR-NH2 | MRJP2, 4 (see Leu408) | 52 | 65.39 ± 2.75 | 72.56 ± 9.33 |
| Ac-LLK-OH | MRJP1, 2, 4 (see Leu146; Leu104; Leu169) | 56 | 141.56 ± 13.90 | 147.60 ± 5.98 |
| Ac-LLK-NH2 | MRJP1, 2, 4 (see Leu146; Leu104; Leu169) | 57 | 159.34 ± 2.34 | 136.90 ± 14.42 |

TABLE 9-continued

Additional synthetic peptides tested for inhibitory activity

| peptide | derived from MRJP | SEQ ID NO: | unmodified | MGO-modified |
|---|---|---|---|---|
| Ac-KI-OH | MRJP1-5+ | 58 | 108.98 ± 9.03 | 92.08 ± 5.79 |

+ = MRJP1: Lys75, Lys358, Lys427; MRJP2: Lys121, Lys127, Lys356, Lys385; MRJP3: Lys132, Lys361, Lys390; MRJP4: Lys131, Lys356; MRJP5: Lys100, Lys130, Lys310, Lys518.

Another synthetic peptide is FAK (Phe-Ala-Lys; e.g., Ac-FAK-OH; SEQ ID NO: 60) which includes a sequence found in MRJP1, MRJP3, and MRJP4.

A table to summarize the amino acid sequences from this Example is provided as follows.

TABLE 10

Summary of amino acid sequences assessed for inhibitory activity

| sequence | SEQ ID NO: |
|---|---|
| PFKI | 61 |
| KISI | 62 |
| KISIHL | 63 |
| PFKISIHL | 64 |
| KN | 65 |
| NQKN | 66 |
| NQKNNN | 67 |
| NQKNNNQN | 68 |
| NQKNNNQNDN | 69 |
| HSSKLH | 70 |
| SKLH | 71 |
| SK | 72 |
| HSSK | 73 |
| SSKS | 74 |
| KS | 75 |
| SSKSNNRHNNND | 76 |
| SSKSNN | 77 |
| SSKSNNRH | 78 |
| SSKSNNRHNN | 79 |
| KH | 80 |
| QNKHNN | 81 |
| KHNN | 82 |
| QNKH | 83 |
| LVK | 84 |
| LIR | 86 |
| LLK | 89 |
| KI | 90 |
| FDR | 127 |
| HNIR | 128 |
| YINR | 129 |
| FTK | 130 |
| IFVTMLR | 131 |
| MQK | 132 |
| CDR | 133 |
| MTR | 134 |
| FAK | 135 |
| QNDNR | 136 |
| QNGNK | 137 |
| QNGNR | 138 |
| TNR | 139 |
| MDK | 140 |
| MDR | 142 |
| TDK | 143 |
| IDR | 144 |
| VNR | 145 |
| MHR | 47 |
| MNR | 141 |
| LQK | 55 |

The results show that both C-terminal and internal peptides can provide inhibition of Cathepsin B after modification of lysine with MGO. The peptide analogue LIR (SEQ ID NO: 51) has particularly potent activity.

The presence of endogenous protease activity in honey has been determined previously ((Larocca et al., 2012)), and we demonstrate that this protease leads to degradation of MRJP proteins in the presence of urea. The release of peptides from MRJP proteins is therefore expected during prolonged incubation of Manuka honey leading to release of MGO-modified peptides that have enhanced Cathepsin B inhibition.

Certain peptides show stimulatory activity in the absence of MGO treatment. This activation is in most cases lost after treatment with MGO. In some cases, longer peptides are more active. For specific peptides, the lysine is positioned at least 3 amino acid away from the C-terminal amino acid, and no more than 6 amino acids away from the C-terminal amino acid. For inhibition, a free C-terminus is typically present. This allows a favorable interaction with Cathepsin B and potentially increased inhibition.

For the assayed peptides, an acid functional end is more likely to produce increased activity as compared to an amidated end. This is consistent with internal protease digestion having the specificity similar to that of pancreatic trypsin, i.e., cleavage C-terminal to arginine and lysine residues, as long as the following amino acid is not proline. The preference for a C-terminal carboxylate group is understandable in context of the structure of Cathepsin B and its exopeptidase activity that acts on a C-terminal end.

Notably, the occlusive loop of Cathepsin B contains two histidine residues that are believed to coordinate to the C-terminus of the peptide. See, e.g., Musil, D., Zucic, D., Turk, D., Engh, R. A., Mayr, I., Huber, R., Popovic, T., Turk, V., Towatari, T., Katunuma, N., Bode, W. (1991) The refined 2.15 A X-ray crystal structure of human liver cathepsin B: the structural basis for its specificity. EMBO J. 10: 2321-2330. This positions the peptide bond between amino acid 2 and 3 up from the C-terminus of the peptide. In addition, the orientation of peptides with respect to Cathepsin B may be inverted 180° if the primary amine or epsilon amino group of lysine has reacted with MGO. As noted above, this can undergo a cannizzaro rearrangement to produce CEL. This may also occur on the side chain epsilon amino group of lysine.

Regarding the FAK peptide analogue (SEQ ID NO: 100), this showed limited inhibitory activity with the C-terminus containing paranitroanilide (pNA). It was postulated that this could block recognition of the peptide by Cathepsin B. To test this, the pNA group was removed under basic conditions in the presence of NaOH. The peptide was reassessed for activity before and after MGO-modification (data not shown). Inhibitory activity was still not observed, suggesting that the position of lysine within the peptide sequence can affect activity. From this, it is concluded that it may be beneficial to position the lysine such that it sits closer to the active site of Cathepsin B.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the scope and/or essential characteristics of the present invention.

Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the invention is intended to encompass, within its scope, the modifications, substitutions, and variations to processes, manufactures, compositions of matter, compounds, means, methods, and/or steps disclosed herein.

REFERENCES

K. Kohno, I. Okamoto, O. Sano, N. Arai, K. Iwaki, M. Ikeda, and M. Kurimoto (2004) Royal jelly inhibits the production of proinflammatory cytokines by activated macrophages, Biosci. Biotechnol. Biochem., 68(1):138-145.

Kimura Y, Miyagi C, Kimura M, Nitoda T, Kawai N, Sugimoto H. (2000Structural features of N-glycans linked to royal jelly glycoproteins: structures of high-mannose type, hybrid type, and biantennary type glycans. Biosci. Biotechnol. Biochem. 64(10):2109-20.

J. Simuth, K. Bilikova, E. Kovacova, Z. Kuzmova, and W. Schroder (2004) Immunochemical approach to detection of adulteration in honey: physiologically active Royal Jelly protein stimulating TNF-alpha release is a regular component of honey, Journal of Agriculture and Food Chemistry. 52(8):2154-8.

B. Lerrer, K. Zinger-Yosovich, B. Avrahami, and N. Gilboa-Garber (2007) Honey and royal jelly, like human milk, abrogate lectin-dependent infection-preceding *Pseudomonas aeruginosa* adhesion. ISME Journal. 1:149-155.

E. Mavric, S. Wittmann, G. Barth, and T. Henle (2008) Identification and quantification of methylglyoxal as the dominant antibacterial constituent of Manuka (*Leptospermum scoparium*) honeys from New Zealand. Mol. Nutr. Food Res. 52.

Auwerx J. (1991). The human leukemia cell line, THP-1: a multifaceted model for the study of monocyte-macrophage differentiation. Experientia. 47:22-31.

Wan, C. P., C. S. Park, et al. (1993). A rapid and simple microfluorometric phagocytosis assay. Journal of Immunological Methods 162(1):1-7.

Allen, K. L., P. C. Molan, et al. (1991). A survey of the antibacterial activity of some New Zealand honeys. Journal of Pharmacy and Pharmacology. 43(12):817-22.

White, J. (1975). Honey: a comprehensive survey. London, Heinemann.

Schmitt, A., J. Schmitt, et al. (2005). Characterization of advanced glycation end products for biochemical studies: side chain modifications and fluorescence characteristics. Analytical Biochemistry. 338:201-215.

Jonathan W. C. Brock, William E. Cotham, Suzanne R. Thorpe, John W Baynesl and Jennifer M. Ames. (2007). Detection and identification of arginine modifications on methylglyoxal-modified ribonuclease by mass spectrometric analysis. J. Mass Spectrom. 42:89-100.

Kim J, Kim N H, Sohn E, Kim C S, Kim J S. (2010). Methylglyoxal induces cellular damage by increasing argpyrimidine accumulation and oxidative DNA damage in human lens epithelial cells. Biochem Biophys Res Commun. 391(1):346-51. Epub 2009 Nov. 12.

Brömme D, Steinert A, Fittkau S, Kirschke H. (1987). Action of rat liver cathepsin B on bradykinin and on the oxidized insulin A-chain. FEBS Lett. July 27; 219(2):441-4.

Chapman H A Jr, Munger J S, Shi G P. (1994). The role of thiol proteases in tissue injury and remodeling. Am J Respir Crit Care Med. 1994 December; 150(6 Pt 2):5155-9.

June O'Neil, George Hoppe, Lawrence M. Sayre, and Henry F. Hoff (1997). Inactivation of cathepsin B by oxidised LDL involves complex formation induced by binding of putative reactive sites exposed at low pH to thiols on the enzyme. Free Radical Biology & Medicine. 23(2):215-225.

Ahmed N K, Martin L A, Watts L M, Palmer J, Thornburg L, Prior J, Esser R E. (1992) Peptidyl fluoromethyl ketones as inhibitors of cathepsin B. Implication for treatment of rheumatoid arthritis. Biochem Pharmacol. September 25; 44(6):1201-7.

Rossano R, Larocca M, Polito T, Perna A M, Padula M C, et al. (2012) What Are the Proteolytic Enzymes of Honey and What They Do Tell Us? A Fingerprint Analysis by 2-D Zymography of Unifloral Honeys. PLoS ONE 7(11): e49164. doi:10.1371/journal.pone1149164

What we claim is:

1. An isolated functional fragment of a major royal jelly protein (MRJP), which has anti-inflammatory capacity, which is not a naturally occurring functional fragment of a major royal jelly protein, and which includes up to 20 amino acids, wherein a lysine or arginine amino acid residue of the functional fragment has been chemically modified by methylglyoxal (MGO); and wherein:
   a. the functional fragment consists of the amino acid sequence:
   KISIHL (SEQ ID NO: 10); or
   b. the functional fragment comprises the peptide analogue:
   Ac-PFKISIHL-OH (SEQ ID NO: 19).

2. The isolated functional fragment of claim 1, which is chemically synthesized.

3. The isolated functional fragment of claim 1, which is recombinantly produced.

4. A composition comprising the isolated functional fragment of claim 1, or an analogue thereof.

5. A wound dressing comprising a functional fragment of a major royal jelly protein (MRJP); wherein the functional fragment has anti-inflammatory capacity; wherein the functional fragment has been isolated, enriched, chemically synthesized, or recombinantly produced; the functional fragment including up to 20 amino acids; wherein a lysine or arginine amino acid residue of the functional fragment has been chemically modified by methylglyoxal (MGO); and wherein:
   a. the functional fragment consists of the amino acid sequence:
   KISIHL (SEQ ID NO: 10); or
   b. the functional fragment comprises the peptide analogue:
   Ac-PFKISIHL-OH (SEQ ID NO: 19).

6. The wound dressing of claim 5, wherein the functional fragment is chemically synthesized.

7. The wound dressing of claim 5, wherein the functional fragment is recombinantly produced.

8. A method of inhibiting Cathepsin B activity in a cellular tissue, comprising the step of contacting the cellular tissue with a functional fragment of a major royal jelly protein (MRJP); wherein the functional fragment has been isolated, enriched, synthesized, or recombinantly produced; and which includes up to 20 amino acids wherein a lysine or arginine amino acid residue of the functional fragment has been chemically modified by methylglyoxal (MGO); and wherein
   a. the functional fragment consists of the amino acid sequence
   KISIHL (SEQ ID NO: 10); or
   b. the functional fragment comprises the peptide analogue
   Ac-PFKISIHL-OH (SEQ ID NO: 19).

* * * * *